United States Patent
Block et al.

(10) Patent No.: US 6,967,216 B2
(45) Date of Patent: Nov. 22, 2005

(54) AMINO SUBSTITUTED DIBENZOTHIOPHENE DERIVATIVES FOR THE TREATMENT OF DISORDERS MEDIATED BY NP Y5 RECEPTOR

(75) Inventors: Michael Howard Block, Macclesfield (GB); Craig Samuel Donald, Macclesfield (GB); David Robert Brittain, Macclesfield (GB); Kevin Michael Foote, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/275,529

(22) PCT Filed: May 1, 2001

(86) PCT No.: PCT/GB01/01899

§ 371 (c)(1),
(2), (4) Date: Nov. 5, 2002

(87) PCT Pub. No.: WO01/85714

PCT Pub. Date: Nov. 15, 2001

(65) Prior Publication Data

US 2003/0225097 A1 Dec. 4, 2003

(30) Foreign Application Priority Data

May 5, 2000   (GB) .............................................. 0010757

(51) Int. Cl.$^7$ ........................ A61K 31/38; A61K 31/44; A61K 31/40; C07D 333/74; C07D 211/70
(52) U.S. Cl. .................... 514/443; 514/281.1; 514/422; 549/43; 546/337; 548/525
(58) Field of Search .............................. 514/443, 281.1, 514/422; 549/43; 546/337; 548/525

(56) References Cited

U.S. PATENT DOCUMENTS

| | | | |
|---|---|---|---|
| 4,111,850 A | | 9/1978 | Kwalwasser |
| 4,703,107 A | | 10/1987 | Monsigny et al. |
| 4,965,284 A | * | 10/1990 | Nair et al. |
| 4,997,844 A | | 3/1991 | Bernstein et al. |
| 5,234,942 A | | 8/1993 | Bernstein et al. |
| 5,254,135 A | | 10/1993 | Lang et al. |
| 6,037,362 A | | 3/2000 | Miyoshi et al. |

FOREIGN PATENT DOCUMENTS

| | | |
|---|---|---|
| DE | 3436281 A1 | 4/1985 |
| EP | 179619 A1 | 10/1985 |
| EP | 342433 A2 | 11/1989 |
| EP | 381422 A1 | 8/1990 |
| EP | 179619 B1 | 9/1990 |
| EP | 783503 B1 | 4/1996 |
| EP | 882707 A1 | 7/1997 |
| EP | 829753 A1 | 3/1998 |
| EP | 997458 A1 | 1/1999 |
| EP | 945438 A1 | 9/1999 |
| JP | 1174077 | 7/1989 |
| JP | 11130817 | 5/1999 |
| JP | 11349572 | 12/1999 |
| WO | 92/05170 | 4/1992 |
| WO | 93/07902 | 4/1993 |
| WO | 93/07903 | 4/1993 |
| WO | 93/16694 | 9/1993 |
| WO | 93/18026 | 9/1993 |
| WO | 95/06046 | 3/1995 |
| WO | 96/16542 | 6/1996 |
| WO | 97/19682 | 6/1997 |
| WO | 97/20821 | 6/1997 |
| WO | 98/01417 | 1/1998 |
| WO | 98/35957 | 8/1998 |
| WO | 98/35944 | 9/1998 |

(Continued)

OTHER PUBLICATIONS

Letois, B., et al. Etude de la cytotoxicite in vitro de derives du carbazole III. 3–Amino et 3–nitro–1, 4–dimethyl–9H–carbazoles diversement substitutes en position 6. European Journal of Medicinal Chemistry 25, 775–84 (1990).

Block, M., et al. Discovery and Optimization of a Series of Carbazole Ureas as DPY5 Antagonists for the Treatment of Obesity. Journal of Medicinal Chemistry 45, No. 16, 3509–23 (2002).

(Continued)

*Primary Examiner*—Deborah C. Lambkin
(74) *Attorney, Agent, or Firm*—Ropes & Gray LLP

(57) ABSTRACT

Compounds of formula (I):

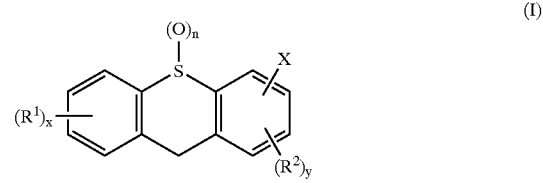

wherein:
X is a group of formula (A) or (B):

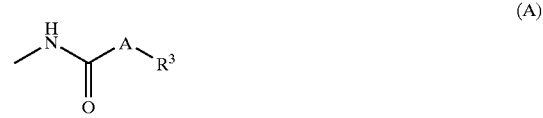

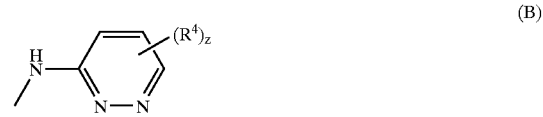

and $R^1$, $R^2$, $R^3$, $R^4$, n, x, y and z are as defined within are described.

Processes for their preparation and their use in the treatment of disorders mediated by the neuropeptide Y5 receptor in a warm-blooded animal, such as a human being are also described.

19 Claims, No Drawings

FOREIGN PATENT DOCUMENTS

| WO | 98/46590 | 10/1998 |
|---|---|---|
| WO | 99/03846 | 1/1999 |
| WO | 99/28297 | 6/1999 |
| WO | 99/29660 | 6/1999 |
| WO | 99/32111 | 7/1999 |
| WO | 99/32463 | 7/1999 |
| WO | 99/48868 | 9/1999 |
| WO | 99/48888 | 9/1999 |
| WO | WO 99/51598 | 10/1999 |
| WO | 99/51600 | 10/1999 |
| WO | 99/55667 | 11/1999 |
| WO | 99/64394 | 12/1999 |
| WO | 00/08015 | 2/2000 |
| WO | 00/20376 | 4/2000 |
| WO | 00/23425 | 4/2000 |
| WO | 00/63171 | 10/2000 |
| WO | 00/69849 | 11/2000 |
| WO | 01/07409 A1 | 2/2001 |
| WO | 01/85730 A1 | 11/2001 |
| WO | 01/90120 A2 | 11/2001 |
| WO | 02/051806 | 7/2002 |

OTHER PUBLICATIONS

Derwent Abstract XP002193934 (cited for 100249).

Papamicael, C., et al. Some Applications of the Regioselective Lithiation of a–Carbolines. Heterocycles 47, No. 2 (1998).

Stephenson, L., et al. Synthesis of some Substituted a–Carbolines. J. Chem. Soc. (C) 10, 1355–64 (1970).

Grammaticakis, M., et al. Academie Des Sciences 251, 23, 2728–2731 (1960).

Heterocyclic Compounds, 18701–18702 (1961).

Cerri, R., et al. Nuovi derivati di 7–Ammino–2,3–Polimetilenindoli ad Attivita Antiinfiammatoria. Il Farmaco Ed. Sc. 43, 91–101 (1987).

Cerri, R., et al. Attivita Analgesica di Derivati di 7–Ammino–2,3–Polimetilenindoli E Loro Congeneri. Il Farmaco 43, 113–123 (1988).

Eagle, E., et al. Toxicity, Antipyretic and Analgesic Studies on 39 Compounds Including Aspirin, Phenacetin and 27 Derivatives of Carbazole and Tetrahydrocarbazole. Carbazoles and Tetrahydrocarbazoles, 450–457 (1950).

Zinnes, H., et al. 1,2–Benzothiazines. 6. 3–Carbamoyl–4–hydrozy–2H–1,2–benzothiazine 1,1–Dioxides as Antiinflammatory Agents 16, vol. 1, 44–48 (1973).

Hamois–Pontoni, M., et al. Hydrosoluble Fluorogenic Substrates for Plasmin. Analytical Biochemistry 193, 248–255 (1991).

Simionescu, C.I., et al. New Carbazole–Containing Monomers and Polymers. Journal of Polymer Science 17, 2287–2297 (1979).

Tabka, T., et al. Etude de la cytotoxicite in vitro de derives du carbazole I. Nitro et amino–9H–carbazoles. Eur. J. Med. Chem. 23, 119–124 (1988).

Harfenist, M., et al. Selective Inhibitors of Monoamine Oxidase 2. Arylamide SAR. J. Med. Chem., 37, 2085–2089 (1994).

Harfenist, M. Prevention of Ames Test Mutagenicity by Chemical Modification in a Series of Monoamine Oxidase Inhibitors. J. Med. Chem. 23, 825–827 (1980).

Kudo, H., et al. Synthesis of Monoamino and Monohydroxydibenzothiophenes. J. Heterocyclic Chem. 22, 215–219 (1985).

Jiang, Z., et al. Photocyclizations of Arylthiofluoroaromatic Compounds: Synthesis of Benzothiophenes. Heterocycles 37, No. 3, 1443–1446 (1994).

Ohnmacht, C., et al. N–Arly–3,3,3–trifluoro–2–hydroxy–2–methylpropanamides: Katp Potassium Channel Openers. Modifications on the Western Region. J. Med. Chem. 39, 4592–4601 (1996).

Johnson, J., et al. Synthesis and Antimalarial Effects of [1] Benzothieno [3,2–f] quinazoline–1,3–diamine (1). J. Heterocyclic Chem. 14, 1209–1215 (1977).

Tye, H., et al. Design, Synthesis and preliminary studies on a novel class of chiral receptor for the recognition of amino acid derivatives. J. Chem. Soc., Perkin Trans. 1, 457–465 (1998).

Wade, J., et al. Antiallergic Activity of Tetracyclic Derivatives of Quinoline–2–carboxylic Acid. 2. Some Benzothienoquinolinecarboxylic Acids. Journal of Medicinal Chemistry 21, No. 9, 941–949 (1978).

Chakrabarty, M., et al. An Expedient Synthesis of 5,11–Dimethylindolo [3,2–b]–Carbazole, a Potent Ligand for the Receptor for TCDD. Synthetic Communications 26(16), 3015–3023 (1996).

Besson, T., et al. Synthesis and Fluorescent Propeties of New Heterobifunctional Fluorescent Probes. Heterocycles 34, No. 2, 273–291 (1992).

Lancelot, J., et al. Etude des Reactions de Nitration de L'Acetamido–3 Ethyl–9 Carazole. J. Heterocyclic Chem. 18, 1281–1285 (1981).

J. Soc. Org. Synthet Chem. Japan 12, 29–34 (1954).

Brunton, R.J., et al. Experiments on the Preparation of Indolocarbazoles. Part IX. The Preparation of 9–Methylindolo (2':3'–1:2) carbazole. J. Chem. Soc., 4783–4785 (1956).

Kinsley, D.A., et al. The Synthesis and Structure of Some Pyrroloindoles. Journal of the Chemical Society, 1–7 (1958).

Perche, J.C., et al. Carcinogenic Nitrogen Compounds. Part LXXIV. Skraup and Combes–Beyer Reactions with 3–Aminocarbazoles; a New Route to Pyrido–[3,2'–b]carbazoles. J. Chem. Soc. 2, 260–262 (1972).

Kyziol. J., et al. N–Methyl Derivatives of 3–Aminocarbazole. Pol. J. Chem. 57, 7–8–9, 839–847 (1983).

Kyziol, J., et al. Bimolecular Reduction of 3–Nitro–9–Ethylcarbazole. Pol J. Chem. 55, 4, 937–940 (1981).

Cordella, A. Ricerche su alcuni coloranti furoil–azoici a sviluppo. Ricerca Sci. 26, 3352–3356 (1956).

Tye, H., et al. The Synthesis of a Synthetic Receptor via Directed Lithiations of Dibenzofuran and Bibenzothiophene. Synlett 7, 770–772 (1995).

Jayalakshmi, S., et al. Proton and Carbon NMR Spectra of 2–Substituted Dibenzothiophenes. Magnetic Resonance in Chemistry 27, 684–686 (1989).

Ponec, R., et al. The Effect of Substitution on Oxidation of Sulphides. Collect Czech. Chem. Commun. 39(8), 2088–2098 (1974).

Sawicki, E., et al. N–Trifluoroacetyl Derivatives of Carcinogenic Amines. J. Amer. Chem. Soc. 75, 2266–2267 (1953).

Brown, R., et al. Some Derivatives of Dibenzothiophene. J. Amer. Chem. Soc. 70, 1748–1749 (1948).

El–Naggar, A.M., et al. Synthesis of Some New 2– and 3–Substituted Aminoacyl–Aminodibenzothiophene Derivatives. Glas. Hem. Drus. Beograd. 49(4), 151–155 (1984).

Gilman, H., et al. Some Dialkylaminoalkylamino Dervatives of Dibenzothiophene. J. Am. Chem. Soc. 68, 1514–1515 (1946).

Papamicael, C., et al. Study of the Lithiation of 3–Substituted a–Carbolines A New Route to 3,4–Disubstituted Derivatives. Tett. Lett. 35(24) 4099–4102 (1994).

Papamicael, C., et al., "Study of the Lithiation of 3–Substituted a–Carbolines A New Route to 3,4–Disubstituted Derivatives," Tetrahedron. Letters, 35(24), 4099–4102 (1994).

* cited by examiner

AMINO SUBSTITUTED DIBENZOTHIOPHENE DERIVATIVES FOR THE TREATMENT OF DISORDERS MEDIATED BY NP Y5 RECEPTOR

This application is a national stage filing under 35 U.S.C. 371 of PCT application PCT/GB01/01899, filed May 1, 2001, which claims priority from United Kingdom Application No.0010757.3, filed May 5, 2000, the specifications of each of which are incorporated by reference herein. PCT Application PCT/B01/0101899 was published under PCT Article 21(2) in English.

This invention relates to compounds which antagonise the interaction between neuropeptide Y (NPY) and the neuropeptide Y5 (NPY-5) receptor sub-type. This invention also relates to processes for the manufacture of NPY-5 receptor antagonists or agonists, pharmaceutically acceptable salts thereof, and to novel pharmaceutical compositions of NPY-5 receptor antagonists or agonists.

NPY is a 36 amino acid polypeptide which is a member of the pancreatic polypeptide family of regulatory peptides with widespread distribution throughout the mammalian system. NPY is the most abundant neuropeptide in the central and peripheral nervous systems and has been shown to have powerful and complex effects on feeding, anxiety, circadian rhythms, reproduction, pituitary-adrenocortical axis function, memory retention, seizures, therino-regulation, and cardiovascular and gastrointestinal functions. NPY interacts with a heterogeneous population of at least six receptor subtypes, $Y_1$–$Y_6$ which activate adenylate cyclase via a G-protein. For reviews of NPY see: CRC Critical Reviews in Neurobiology. (1988) 4, 97–135; Regulatory Peptides (1996) 62, 1–11.

One of the most striking actions of NPY is induction of feeding in a variety of vertebrate species. Direct injection of NPY into the hypothalamus of satiated rats can increase food intake up to 10-fold over a 4 hour period and NPY is the only known peptide which can cause animals to eat until they are obese. Recent studies on NPY have focussed on the identification of the NPY receptor responsible for the regulation of feeding. The NPY-5 receptor has been identified as the receptor most closely matching a proposed appetite receptor. The functional role of this receptor was addressed by receptor blockade studies. Intra-ccrcbro-ventricular injection of NPY-5 receptor antisense oligodeoxynucleotides prevented the increase in hypothalamic NPY levels during food deprivation and inhibited fasting-induced food intake in rats [Schaffhauser et al (1997) Diabetes 46, 1792–1798]. Thus the NPY-5 receptor is a potential pharmacological target in the modulation of feeding disorders such as obesity. For reviews on the association between NPY and feeding see: Zimanyi et al (1998) Current Pharn Des 4, 349–66; Heinrichs et al (1998) Vitamins and Hormones 54, 51–66.

Obesity is a large and ever expanding problem in affluent societies, which has reached epidemic proportions. According to the US Institute of Medicine, 59% of Americans are clinically obese or at least 20% above their ideal body weight. Obesity is associated with susceptibility to a number of other conditions e.g. non-insulin-dependent diabetes, hypertension, dyslipidaemia and coronary heart disease. These conditions lead to reduction in life expectancy and decreased quality of life. The overall financial burden of obesity is difficult to quantify but it has been estimated that in the US it may account for 6–8% of total healthcare expenditure.

Thus there is need for pharmaceutical agents which have efficacy in the treatment of eating disorders such as obesity, anorexia and bulimia. Modulation of NPY activity through antagonism at the NPY-5 receptor offers one potential target for pharmacological intervention in these conditions.

Accordingly, the present invention provides a compound of formula (1):

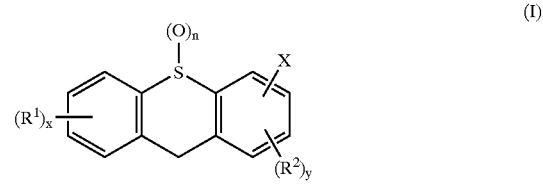

wherein:
X is a group of formula (A) or (B):

$R^1$ is cyano, halo, trifluoromelhyl, trifluoromethoxy, $C_{1-4}$Aalkyl, $C_{1-4}$alkoxy, N-($C_{1-4}$alkyl)amino or N,N-($C_{1-4}$alkyl)$_2$amino;

$R^2$ is halo, cyano, hydroxy, trifluoromethyl, trifluoromethoxy, $C_{1-4}$alkyl or $C_{1-4}$alkoxy;

A is —$NR^3$—, —O— or a direct bond; wherein $R^a$ is hydrogen, $C_{1-10}$alkyl, $C_{2-10}$alkenyl, $C_{2-10}$alkynyl; wherein $R^a$ may be optionally substituted by one or more $R^5$;

$R^3$ is hydrogen, $C_{1-10}$alkyl, $C_{2-10}$alkenyl or $C_{2-10}$alkynyl wherein $R^3$ may be optionally substituted by one or more $R^6$; or $R^3$ is carbocyclyl or heterocyclyl wherein $R^3$ may be optionally substituted on carbon by one or more $R^7$; and wherein if said heterocyclyl contains an —NH—moiety that nitrogen may be optionally substituted by $R^8$;

$R^4$ is halo, nitro, cyano, hydroxy, trifluoromethyl, trifluoromethoxy, amino, carboxy, carbamoyl, mercapto, sulphamoyl, $C_{1-4}$alkoxycarbonyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, N-(carbocyclyl)carbamoyl, N,N-(carbocyclyl)$_2$carbamoyl, N-(heterocyclyl)carbamoyl, N,N-(heterocyclyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)2sulphamoyl, $C_{1-4}$alkylsulphonylamino or (nitrogen-linked heterocyclic ring)carbonyl;

$R^5$ and $R^6$ are independently selected from halo, hydroxy, cyano, carbamoyl, ureido, amino, nitro, carboxy, carbarnoyl, mercapto, sulphamoyl, aminosulphamoyl, $C_{1-6}$alkoxy, $C_{1-6}$alkanoyl, $C_{1-6}$alkanoyloxy, $C_{1-6}$alkanoylamino, $C_{2-6}$alkenyloxycarbonyl, $C_{1-6}$alkoxycarbonyl, hetcrocyclyl, heterocyclyloxy, heterocyclylamino, heterocyclyl-N-($C_{1-6}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-6}$alkyl)amino, carbocyclylsulphonyl, carbocyclylcarbonyl, carbocyclylcarbonylamino, carbocyclyloxycarbonyl, N-($C_{1-6}$alkyl)amino, N,N-($C_{1-6}$alkyl)$_2$amino, $C_{1-6}$alkoxycarbonylamino, N-($C_{1-6}$alkyl)carbarnoyl, N,N-

($C_{1-6}$alkyl)$_2$carbamoyl, $C_{1-6}$alkylS(O)$_a$ wherein a is 0–2, N-($C_{1-6}$alkyl)sulphamoylamino, N,N-($C_{1-6}$alkyl)$_2$ sulphamoylamino, $C_{1-6}$alkylsulphonylamino, ($C_{1-6}$alkyl) sulphonyl-N-($C_{1-6}$alkyl)amino, N-($C_{1-6}$alkyl)sulphamoyl and N,N-($C_{1-6}$alkyl)$_2$sulphamoyl; wherein $R^5$ and $R^6$ may be optionally substituted on carbon by one or more $R^9$; and wherein if said heterocyclyl contains an —NH—moiety that nitrogen may be independently optionally substituted by $R^{10}$;

$R^7$ and $R^9$ are independently selected from halo, hydroxy, cyano, carbamoyl, ureido, trifluoromethyl, trifluoromethoxy, amino, nitro, carboxy, carbamoyl, mercapto, sulphamoyl, aminosulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{1-4}$alkoxycarbonylamino, $C_{2-4}$alkenyloxycarbonyl, $C_{1-4}$alkanoyl, $C_{1-4}$alkanoylamino, $C_{1-4}$alkanoyloxy, N-($C_{1-4}$alkyl)amino, N,N-($C_{1-4}$alkyl)$_2$ amino, N-($C_{1-4}$ alkyl)carbamoyl, N,N-($C_{1-4}$alkyl)$_2$ carbamoyl, $C_{1-4}$alkylS(O)$_a$ wherein a is 0–2, N-($C_{1-4}$alkyl) sulphamoylamino, N,N-($C_{1-4}$alkyl)$_2$sulphamoylamino, ($C_{1-4}$ alkyl)sulphonylamino, ($C_{1-4}$alkyl)sulphonyl-N-($C_{1-4}$ alkyl)amino, N-($C_{1-4}$alkyl)sulphamoyl, N,N-($C_{1-4}$alkyl)$_2$ sulphamoyl, heterocyclyl, heterocyclyloxy, heterocyclylamino; heterocyclyl-N-($C_{1-4}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-4}$alkyl)amino, carboocyclylsulphonyl, carbocyclylcarbonyl, carbocyclylcarbonylamino, and carbocyclyloxycarbonyl; wherein $R^7$ and $R^9$ maybe independently optionally substituted on carbon by one or more $R^{11}$;

$R^8$ and $R^{10}$ are independently selected from $C_{1-4}$alkyl, $C_{1-4}$alkanoyl, sulpharnoyl, $C_{1-4}$alkylsulphonyl, $C_{1-4}$ alkoxycarbonyl, carbamoyl, N-($C_{1-4}$alkyl)carbamoyl, N,N-($C_{1-4}$alkyl)$_2$carhamoyl, N-($C_{1-4}$alkyl)sulphamoyl, N,N-($C_{1-4}$alkyl)$_2$sulphamoyl, heterocyclyl, hetcrocyclylcarbonyl, heterocyclyloxycarbonyl, heterocyclylsulphonyl, carbocyclyl, carbocyclylcarbonyl, carbocyclyloxycarbonyl and carbocyclylsulphonyl; wherein $R^8$ and $R^{10}$ may be independently optionally substituted on carbon by one or more $R^{12}$;

$R^{11}$ and $R^{12}$ are independently selected from halo, hydroxy, cyano, carbamoyl, ureido, amino, nitro, carboxy, carbamoyl, mercapto, sulphamoyl, methyl, ethyl, vinyl, allyl, methoxy, ethoxy, vinyloxy, allyloxy, methoxycarhonyl, formyl, acetyl, fornamido, acelylamino, acetoxy, methylamino, dimcthylamino, N-methylcarbamoyl, N,N-dimethylcarbamoyl, methylthio, methylsulphinyl, mesyl, N-methylsulphamoyl, N,N-dimethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

x is 0–4; wherein the values of $R^1$ may be the same or different;

y is 0–3; wherein the values of $R^2$ may be the same or different;

z is 0–3; wherein the values of $R^4$ may be the same or different; and n is 0–2;

or a pharmaceutically acceptable salt, prodrug or solvate thereof;

with the provisos when X is a group of formula (A):

1) when $R^3$ is a nitrogen linked heterocyclyl, A is a direct bond;
2) when x and y are 0 and n is 2, the group $R^3$—A—C(O)—NH— is not 2-formamido, 2-acetamido, 3-acetamido, 2-propionamido, 3-[2-(fur-2-ylcarbonylmethyl)acetamido], 2-(2-ptlialimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-bcnzylacetamido), 3-(2-pthalimidoacetamido), 3-(3-pthalimidopropionamido), 3-(2-pthalimido-2-isopropylacetamido), 3-(2-pthalimdo-2-isobutylacetamido), 3-(2-pthalimido-2-benzylacetamido), 3-(2-amninoacetamido), 3-(3-aminopropionamido), 3-(2-amino-2-isopropylacetamido), 3-(2-amino-2-isobutylacetamido), 3-(2-amino-2-benzylacetamido) or 2-(3,3,3-trifluoro-2-hydroxy-2-methylpropionamido);
3) when x and y are 0 and n is 1, the group $R^3$—A—C(O)—NH—is not 3-acetamido, 3-(2-pthalimidoacetamido), 3-(3-pthalimiidopropionamido), 3-(2-pthalimido-2-isopropylacetamido), 3-(2-pthalimido-2-isobutylacetamido), 3-(2-pthalimido-2-benzylacetarnido), 3-(2-aminoacetamido), 3-(3-aminopropionamido), 3-(2-amino-2-isopropylacetamido), 3-(2-amino-2-isobutylacetamido) or 3-(2-amino-2-benzylacetamido);
4) when x and y are 0 and n is 0, the group $R^3$—A—C(O)—NH— is not 2-benzamido, 2-acetamido, 2-benzyloxycarbonylamino, 2-(2-pthalimidoacetamido), 2-(3-pthalimidopropionamido), 20 2-(2-pthalimido-2-isopropylacetamido), 2-(2-pthalimido-2-isobutylacetamido), 2-(2-pthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(trifluoroacetamido), 3-benzyloxycarbonylamino or 4-t-butyloxycarbonylamino;
5) when $(R^1)_x$ is 7-fluoro, y is 0 and n is 2, the group $R^3$—A—C(O)—NH— is not 3-acctamido;
6) when x is 0, $(R^2)_y$ is 1-cyano and n is 0, the group $R^3$—A—C(O)—NH— is not 2-acetamido;
7) when x is 0, $(R^2)_y$ is 3-bromo and n is 0, the group $R^3$—A—C(O)—NH— is not 2-acetamido or 2-benzamido;
8) when x is 0, $(R^2)_y$ is 1-bromo and n is 0, the group $R^3$—A—C(O)—NH— is not 2-acetamido or 2-benzarnido; and
9) when x is 0, $(R^2)_y$ is 1-chloro or 4-chloro and n is 0, the group $R^3$—A—C(O)—NH— is not 2-acetamido.

The numbering system for the dibenzothiophene ring used in the present specification is as follows:

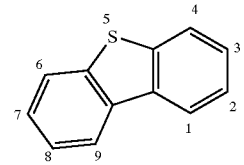

For the avoidance of doubt, where any $C_{1-6}$alkyl is optionally substituted, this also includes the possibility of optional substitution on other groups that contain a $C_{1-6}$alkyl group, for example a $C_{1-6}$alkoxy, $C_{1-6}$alkanoyl, $C_{1-6}$alkanoyloxy, $C_6$alkanoylamino, $C_{1-6}$alkoxycarbonyl, N-($C_{1-6}$alkyl)amino, N,N-di-($C_{1-6}$alkyl)amino, $C_{1-6}$ alkoxycarbonylamino, N-($C_{1-6}$alkyl)carbarnoyl, N,N-di-($C_{1-6}$alkyl)carbamoyl or a $C_{1-6}$alkylS(O)a wherein a is 0–2 group. Similarly, where any heterocyclyl or carbocyclyl may be optionally substituted this also includes the possibility of optional substitution on other groups that contain a heterocyclyl or carbocyclyl group, for example heterocyclyloxycarbonyl and carbocyclylcarbonyl.

In this specification the term "alkyl" includes both straight and branched chain alkyl groups but references to individual alkyl groups such as "propyl" are specific for the straight chain version only. For example, "$C_{1-10}$alkyl", "$C_{1-6}$alkyl" and "$C_{1-4}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" includes phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"heterocyclyl" is a saturated, partially saturated or unsaturated, mono or bicyclic ring containing 3–12 atoms of which at least one atom is chosen from nitrogen, sulphur or oxygen, which may, unless otherwise specified, be carbon or nitrogen linked, wherein a —$CH_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —$CH_2$— group can optionally be replaced by a —C(O)— or a ring sulphur atom may be optionally oxidised to form the S-oxides. Examples and suitable values of the term "heterocyclyl" are thiazolidinyl, pyrrolidinyl, pyrrolinyl, 1,1-dioxotetrahydrothienyl, 2-pyrrolidone, 2-oxazolidinone, 4-thiazolidone, niorpholino, tetrahydropyranyl, piperidyl, piperazinyl, thiomorpholino, 1,1-dioxothiomorpholino, homopiperazinyl, thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl, 4-pyridone, quinolyl, 1,3-benzodioxolyl and 1-isoquinolone. Preferably the term "heterocyclyl" refers to 1,1-dioxotetrahydrothienyl, 2-pyrrolidone, 2-oxazolidinone, morpholino, tetrahydropyranyl, piperidyl, piperazinyl, 1,1-dioxothiomorpholino, imidazolyl, triazolyl and pyridyl. More preferably the term "heterocyclyl" refers to tetrahydropyranyl, morpholino, 2-oxopyrrolidinyl, piperidinyl, pyrrolidinyl, azetidinyl, tetrahydrofuryl, 1,4-dioxa-8-azaspiro[4.5]decanyl, 1,1-dioxotetrahydrothienyl, 1,2,3,4,-tetrahydro-9H-pyrido[3,4-b]indole, decahydroquinolin-1-yl, 1,2,5,6-tetrahydropyridyl, piperazinyl, pyridyl, 1,2,4-triazolyl, thienyl, 2-oxooxazolidinyl, imidazolyl, 1,1-dioxothiomorpholino, 2-oxo-1,2-dihydropyridyl, benzimidazolyl, pyrazolyl, succinimido, 2,4-dioxothiazolidinyl, furyl, pyridazinyl, 1,4-dihydrooxazin-2-one, 2-oxo-2,3-dihydrobenzimidazolyl, 2,3-dihydro-2-oxobenzimidazolyl, thieno[2,3-d]pyrimidinyl or pyrimidinyl.

A "nitrogen-linked heterocyclic ring" is a saturated, partially saturated or unsaturated, mono or bicyclic ring containing 3–12 atoms of which at least one atom is nitrogen, which is linked via a nitrogen atom, wherein a —$CH_2$— group can optionally be replaced by a —C(O)— or a ring sulphur atom may be optionally oxidised to form the S-oxides. Examples and suitable values of a "nitrogen-linked heterocyclic ring" are morpholino, pyrrolidin-1-yl, imidazol-1-yl, 1,1-dioxothiomorpholino and 2-oxopyrrolidin-1-yl.

A "carbocyclyl" is a saturated, partially saturated or unsaturated, mono or bicyclic carbon ring that contains 3–12 atoms. Preferably "carbocyclyl" is a monocyclic ring containing 5 or 6 atoms or a bicyclic ring containing 9 or 10 atoms. Suitable values for "carbocyclyl" include cyclopropyl, cyclobutyl, cyclopentyl, cycloliexyl, phenyl, naphthyl, tetralinyl or indanyl. Particularly "carbocyclyl" is cyclopropyl or phenyl. More particularly "carbocyclyl" refers to cyclopropyl, cyclopentyl, cyclohexyl, bicyclo[2,2,]heptyl or phenyl.

An example of "$C_{1-6}$alkanoyloxy" and "$C_{1-4}$alkanoyloxy" is acetoxy. Examples of "$C_{1-6}$alkoxycarbonyl" and "$C_{1-4}$alkoxycarbonyl" include methoxycarbonyl, etlioxycarbonyl, n- and t-butoxycarbonyl. Examples of "$C_{1-6}$ alkoxycarbonylamino" and "$C_{1-4}$alkoxycarbonylamino" include methoxycarbonylamino, ethoxycarbonylamino, n- and t-butoxycarbonylamino. Examples of "$C_{1-6}$alkoxy" and "$C_{1-4}$ alkoxy" include methoxy, ethoxy and propoxy. Examples of "$C_{1-6}$alkanoylamino" and "$C_{1-4}$ alkanoylamino" include formamido, acetamido and propionylamino. Examples of "$C_{1-6}$alkylS(O)$_a$ wherein a is 0 to 2" and "$C_{1-4}$alkylS(O)$_a$ wherein a is 0 to 2" include methylthio, ethylthio, methylsulfinyl, ethylsulphinyl, mesyl and ethylsulphonyl. Examples of "$C_{1-4}$alkylsulphonyl" include mesyl and ethylsulphonyl. Examples of "$C_{1-6}$alkanoyl" and "$C_{1-4}$ alkanoyl" include propionyl and acetyl. Examples of "N-($C_{1-6}$alkyl)amino" and "N-($C_{1-4}$akyl)amino" include methylamino and ethylamino. Examples of "N,N-($C_{1-6}$alkyl)$_2$ amino" and "N,N-($C_{1-4}$alkyl)$_2$amino" include di-N-methylamino, di-(N-ethyl)amino and N-ethyl-N-methylamino. Examples of "$C_{2-10}$alkenyl" and "$C_{2-4}$ alkenyl" are vinyl, allyl and 1-propenyl. Examples of "$C_{2-10}$oalkynyl" and "$C_{2-4}$alkynyl" are ethynyl, 1-propynyl and 2-propynyl. Examples of "$C_{2-6}$alkenyloxycarbonyl" and "$C_{2-4}$alkenyloxycarbonyl" are vinyloxycarbonyl, allyloxycarbonyl and 1-propenyloxycarbonyl. Examples of "N-($C_{1-6}$ alkyl)sulphamoyl" and "N-($C_{1-4}$alkyl)sulphamoyl" are N-(methyl)sulphamoyl and N-(ethyl)sulphamoyl. Examples of "N-($C_{1-6}$alkyl)$_2$sulphamoyl" and "N-($C_{1-4}$alkyl)$_2$ sulphamoyl" are N,N-(dimethyl)sulphamoyl and N-(methyl)-N-(ethyl)sulphamoyl. Examples of "N-($C_{1-6}$alkyl)carbamoyl" and "N-($C_{1-4}$alkyl)carbamoyl" are methylaminocarbonyl and ethylaminocarbonyl. Examples of "N,N-($C_{1-6}$alkyl)$_2$ carbamoyl" and "N,N-($C_{1-4}$alkyl)$_2$carbamoyl" are dimethylaminocarbonyl and methylethylaminocarbonyl. Examples of "heterocyclyloxy" are pyridyloxy and thiazolyloxy. Examples of "heterocyclylcarbonyl" are pyrimidylcarbonyl and morpholinocarbonyl. Examples of "heterocyclyloxycarbonyl" are pyrrolidinyloxycarbonyl and pyranyloxycarbonyl. Examples of "carbocyclyloxy" are phenoxy and cyclopropyloxy. Examples of "carbocyclylcarbonyl" are benzoyl and cyclohexylcarbonyl. Examples of "carbocyclyloxycarbonyl" are phenoxycarbonyl and indanyloxycarbonyl. Examples of "N-(carbocyclyl)carbamoyl" are N-phenylcarbamoyl and N-cyclopropylcarbamoyl. Examples of "N,N-(carbocyclyl)$_2$carbamoyl" are N,N-diphenylcarbamoyl and N-cyclohexyl-N-cyclopropylcarbarnoyl. Examples of "N-(heterocyclyl)carbamoyl" are N-pyridylcarbamoyl and N-furylcarbamoyl. Examples of "N,N-(heterocyclyl)$_2$carbamoyl" are N,N-dipyridylcarbamoyl and N-pyrimidinyl-N-pyranylcarbanioyl. Examples of "$C_{1-6}$alkylsulphonylamino" and "$C_{1-4}$alkylsulphonylamino" are mesylamino and ispropylsulphonlyamino. Examples of "($C_{1-6}$alkyl)sulphonyl-N-

($C_{1-6}$alkyl)amino" and ($C_{1-4}$alkyl)sulphonyl-N-($C_{1-4}$alkyl) amino are mesyl-N-methylamino and ethylsulphonyl-N-isopropylamino. Examples of "(nitrogen-linked heterocyclic ring)carbonyl" are morpholinocarbonyl and piperazin-1-ylcarbonyl. Examples of "heterocyclylamino" are pyridylamino and furylamino. Examples of "heterocyclyl-N-($C_{1-6}$alkyl)amino" and "heterocyclyl-N-($C_{1-4}$alkyl)amino" are pyrimidinyl-N-methylamino and thienyl-N-isopropylamino. Examples of "heterocyclylsulphonyl" are pyridylsulphonyl and morpholinosulphonyl. Examples of "heterocyclylcarbonylamino" are morpholinocarbonylamino and thienylcarbonylamino. Examples of "carbocyclylamino" are cyclopropylamino and anilino. Examples of "carbocyclyl-N-($C_{1-6}$alkyl)amino" are cyclopropyl-N-methylamino and N-methylanilino. Examples of "carbocyclylsulphonyl" are phenylsulpionyl and cyclohexylsulphonyl. Examples of "carbocyclylcarbonylamino" are benzoylarnino and cyclopenylcarbonylamino. Examples of "N-($C_{1-6}$alkyl) sulphamoylamino" and "N-($C_{1-4}$alkyl)sulphamoylamino" are N-(methyl)sulphamoylamino and N-(ethyl) sulphamoylamino. Examples of "N-($C_{1-6}$alkyl)$_2$ sulphamoylamino" and "N-($C_{1-4}$alkyl)$_2$sulphamoylamino" are N,N-(dimethyl)sulphamoylamino and N-(methyl)-N-(ethyl) sulphamoylamino.

A suitable pharmaceutically-acceptable salt of a compound of formula (I) is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, the example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a prodrug which is broken down in the human or animal body to give a compound of the formula (I). Examples of prodrugs include in vivo hydrolysable esters of a compound of the formula (I).

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984)

An in vivo hydrolysable ester of a compound of the formula (I) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarhonyloxyethyl; 1,3-dioxolen-2-onylmethyl esters, for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-dialkylaninoethyl)-N-alkylcarbamoyl (to give carbamates), dialkylaminoacetyl and carboxyacetyl. Examples of substituents on benzoyl include morpholino and piperazino linked from a ring nitrogen atom via a metbylene group to the 3- or 4- position of the benzoyl ring.

It is to be understood that, insofar as certain of the compounds of formula I defined above may exist in optically active or racemic forms by virtue of one or more asymmetric carbon atoms, the invention includes in its definition any such optically active or racemic form which possesses the property of being an agonist or antagonist at the neuropeptide Y5 receptor. The synthesis of optically active forms may be carried out by standard techniques of organic chemistry well known in the art, for example by synthesis from optically active starting materials or by resolution of a racemic form. Similarly, binding to the neuropeptide Y5 receptor may be evaluated using the standard laboratory techniques remelted to hereinafter.

The invention also relates to any and all tautomeric forms of the compounds of the formula (I) that possess neuropeptide Y5 receptor agonist or antagonist activity.

It will also be understood that certain compounds of the present invention may exist in solvated, for example hydrated, as well as unsolvated forms. It is to be understood that the present invention encompasses all such solvated forms which possess the property of interacting with the neuropeptidc Y5 receptor.

In another aspect of the present invention there is provided a compound of formula

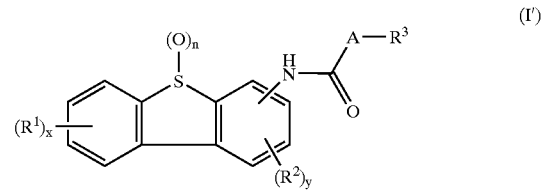

wherein:
$R^1$ is cyano, halo, trifluoromethyl, trifluoromethoxy, $C_{1-4}$alkyl, $C_{1-4}$alkoxy, N-($C_{1-4}$alkyl)amino or N,N-($C_{1-4}$alkyl)$_2$amino;
$R^2$ is halo, cyano, hydroxy, trifluoromethyl, trifluoromethoxy, $C_{1-4}$alkyl or $C_{1-4}$alkoxy;
A is —$NR^a$—, —O— or a direct bond; wherein $R^a$ is hydrogen, $C_{1-10}$alkyl, $C_{2-10}$alkcnyl, $C_{2-10}$alkynyl; wherein said $C_{1-10}$alkyl, $C_{2-10}$alkenyl, $C_{2-10}$alkynyl may be optionally substituted by one or more $R^4$;
$R^3$ is hydrogen, $C_{1-10}$alkyl, $C_{2-10}$alkenyl or $C_{2-10}$alkynyl wherein said $C_{1-10}$alkyl, $C_{2-10}$alkenyl, $C_{2-10}$alkynyl may be optionally substituted by one or more $R^5$; or $R^3$ is carbocyclyl or heterocyclyl wherein said carbocyclyl or heterocyclyl may be optionally substituted on carbon by one or more $R^6$; and wherein if said heterocyclyl contains an —NH— moiety that nitrogen may be optionally substituted by $R^7$;

$R^4$ and $R^5$ are independently selected from halo, hydroxy, cyano, carbamoyl, ureido, amino, nitro, carboxy, carbamoyl, mercapto, sulphamoyl, $C_{1-6}$alkoxy, $C_{1-6 6}$alkanoyl, $C_{1-6}$alkanoyloxy, $C_{1-6}$alkanoylamino, $C_{2-6}$alkenyloxycarbonyl, $C_{1-6}$alkoxycarbonyl, heterocyclyl, heterocyclyloxy, heterocyclylcarbonyl, heterocyclyloxycarbonyl, carbocyclyl, carbocyclyloxy, carbocyclylcarbonyl, carbocyclyloxycarbonyl, N-($C_{1-6}$alkyl)amino, N,N-($C_{1-6}$alkyl)$_2$amino, $C_{1-6}$alkoxycarbonylamino, N-($C_{1-6}$alkyl)carbamoyl, N,N-($C_6$alkyl)$_2$carbamoyl, $C_{1-6}$alkylS(O)$_a$ wherein a is 0–2, N-($C_{1-6}$alkyl)sulphamoyl and N,N-($C_{1-6}$alkyl)$_2$sulphamoyl; wherein any $C_{1-6}$alkyl, heterocyclyl or carbocyclyl may be optionally substituted on carbon by one or more $R^6$; and wherein if said heterocyclyl contains an —NH— moiety that nitrogen may be optionally substituted by $R^7$;

$R^6$ is selected from halo, hydroxy, cyano, carbamoyl, ureido, trifluorometihyl, trifluoromethoxy, amino, nitro, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{2-4}$alkenyloxycarbonyl, $C_{1-4}$alkanoyl, $C_{1-4}$alkanoylamino, $C_{12-4}$alkanoyloxy, N-($C_{1-4}$alkyl)amino, N,N-($C_{1-4}$alkyl)$_2$amino, N-($C_{1-4}$alkyl)carbamoyl, N,N-($C_{1-4}$alkyl)$_2$carbamoyl, $C_{1-4}$alkylS(O)$_a$ wherein a is 0–2, N-($C_{1-4}$alkyl)sulphamoyl, N,N-($C_{1-4}$akyl)2sulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl; wherein any $C_{1-4}$alkyl, carbocyclyl and heterocyclyl may be optionally substituted on carbon by one or more $R^8$;

$R^7$ is selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)$_2$carbamoyl, henzyl, benzoyl, phenylsulphonyl and phenyl;

$R^8$ is selected from halo, hydroxy, cyano, carbamoyl, ureido, amino, nitro, carboxy, carbamoyl, mcrcapto, sulphamoyl, methoxy, methoxycarbonyl, formyl, acetyl, formamido, acetylamino, acetoxy, methylamino, dimethylamino, N-methylcarbamoyl, N,N-dimethylcarbamoyl, methylthio, metiylsulphinyl, mesyl, N-methylsulphamoyl, N,N-dimethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

x is 0–4; wherein the values of $R^1$ may be the same or different;

y is 0–3; wherein the values of $R^2$ may be the same or different; and n is 0–2;

or a pharmaceutically acceptable salt, prodrug or solvate thereof; with the provisos:

1) when $R^3$ is a nitrogen linked heterocyclyl, A is a direct bond;
2) when x and y are 0 and n is 2, the group $R^3$—A—C(O)—NH— is not 2-formamido, 2-acetamido, 3-acetamido, 2-propionamido, 3-[2-(fur-2-ylcarbonylmethyl)acetamido], 2-(2-pthalimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(2-pthalimidoacetamido), 3-(3-pthalimidopropionamido), 3-(2-pthalimido-2-isopropylacetamido), 3-(2-pthalimido-2-isobutylacetamido), 3-(2-pthalimido-2-benzylacetamido), 3-(2-aminoacetamido), 3-(3-aminopropionamido), 3-(2-amino-2-isopropylacetamido), 3-(2-amino-2-benzylacetamido) or 2-(3,3,3-trifluoro-2-hydroxy-2-methylpropionamido);
3) when x and y are 0 and n is 1, the group $R^3$—A—C(O)—NH— is not 3-acetamido, 3-(2-pthalimidoacetamido), 3-(3-pthalimidopropionamido), 3-(2-pthalimiido-2-isopropylacetamido), 3-(2-pthalimido-2-isobutylacetamido), 3-(2-pthalimido-2-benzylacetamido), 3-(2-aminoacetamido), 3-(3-aminopropionamido), 3-(2-amino-2-isopropylacetamido), 3-(2-amino-2-isobutylacetamido) or 3-(2-amino-2-benzylacetamido);
4) when x and y are 0 and n is 0, the group $R^3$—A—C(O)—NH— is not 2-benzamido, 2-acetamido, 2-benzyloxycarbonyl amino, 2-(2-pthalimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(trifluoroacetamido), 3-benzyloxycarbonylamino or 4-t-butyloxycarbonylamino;
5) when $(R^1)_x$ is 7-fluoro, y is 0 and n is 2, the group $R^3$—A—C(O)—NH— is not 3-acetamido;
6) when x is 0, $(R^2)_y$ is 1-cyano and n is 0, the group $R^3$—A—C(O)—NH— is not 2-acetamido;
7) when x is 0, $(R^2)_y$ is 3-bromo and n is 0, the group $R^3$—A—C(O)—NH— is not 2-acetamido or 2-benzamido;
8) when x is 0, $(R^2)_y$ is 1-bromo and n is 0, the group $R^3$—A—C(O)—NH— is not 2-acetamido or 2-benzamido;
9) when x is 0, $(R^2)_y$ is 1-chloro or 4-chloro and n is 0, the group $R^3$—A—C(O)—NH— is not 2-acetamido.

Preferred values of $R^1$, $R^2$, $R^3$, $R^4$, X, A, x, y, z and n are as follows. Such values may be used where appropriate with any of the definitions, claims or embodiments defined hereinbefore or hereinafter. For the avoidance of doubt $R^1$, $R^2$, $R^3$, $R^4$, X, A, x, y, z and n as used below correspond to those used in formula (I). It is to be understood that for compounds of formula (I'), (IA) and (IB) $R^4$ and z are irrelevant, $R^5$ as used in this section corresponds to $R^4$; $R^6$ as used in this section corresponds to-$R^5$; $R^7$ as used in this section corresponds to $R^6$; R8 as used in this section corresponds to $R^7$; and $R^{11}$ as used in this section corresponds to $R^8$.

In one aspect of the invention, preferably x is 0–3; wherein the values of $R^1$ may be the same or different.

In a further aspect of the invention, preferably x is 0–2; wherein the values of $R^1$ may be the same or different.

In an additional aspect of the invention, preferably x is 0–1.

Preferably x is 0.

In one aspect of the invention, preferably y is 0–2; wherein the values of $R^2$ may be the same or different.

In an additional aspect of the invention, preferably y is 0–1.

Preferably y is 0.

In one aspect of the invention, preferably X is a group of formula (A) (as depicted above).

In another aspect of the invention, preferably X is a group of formula (B) (as depicted above).

Preferably X is in the 2-position of the dibenzothiophene ring.

Preferably $R^1$ is halo or $C_{1-4}$alkyl.

More preferably $R^1$ is fluoro or methyl.

Preferably $R^2$ is halo, cyano or $C_{1-4}$alkyl.

More preferably $R^2$ is bromo, cyano or methyl.

Particularly $R^2$ is 3-bromo, 1-cyano, 1-methyl or 3-methyl.

In one aspect of the invention, preferably A is —$NR^a$—.

In another aspect of the invention, preferably A is —O—

In a further aspect of the invention, preferably A is a direct bond.

Preferably A is —$NR^a$— or a direct bond.

Preferably when A is —$NR^a$—; $R^a$ is hydrogen or $C_{1-10}$alkyl optionally substituted by one or more $R^5$.

More preferably when A is —NR—; $R^a$ is hydrogen or unsubstituted $C_{1-10}$alkyl.

Particularly when A is —$NR^a$; $R^a$ is hydrogen or unsubstituted $C_{1-4}$alkyl.

More particularly when A is —$NR^a$; $R^a$ is methyl.

In one aspect of the invention, more particularly when A is —$NR^a$—, $R^a$ is hydrogen.

In another aspect of the invention, more particularly when A is —$NR^a$; $R^a$ is $C_{1-4}$alkyl.

Preferably A is —$NR^a$—, —O— or a direct bond, wherein $R^a$ is hydrogen, $C_{1-10}$alkyl or $C_{2-10}$alkenyl; wherein $R^a$ maybe optionally substituted by one or more $R^5$; wherein $R^3$ is $C_{1-10}$alkyl or $C_{2-10}$alkenyl wherein $R^3$ may be optionally substituted by one or more $R^6$; or $R^3$ is carbocyclyl or heterocyclyl wherein $R^3$ may be optionally substituted on carbon by one or more $R^7$; and wherein if said heterocyclyl contains an —NH— moiety that nitrogen may be optionally substituted by $R^8$;

$R^5$ and $R^6$ are independently selected from hydroxy, cyano, amino, $C_{1-6}$alkoxy, heterocyclyl, heterocyclyloxy, carbocyclyl, carbocyclyloxy, carbocyclyl-N-($C_{1-6}$alkyl) amino, N,N-($C_{1-6}$alkyl)$_2$amino, $C_{1-6}$alkoxycarbonylamino, $C_{1-6}$alkylS(O)$_a$ wherein a is 0–2, N,N-($C_{1-6}$alkyl)$_2$ sulphamoylamino and $C_{1-6}$alkylsulphonylamino; wherein $R^5$ and $R^6$ may be independently optionally substituted on carbon by one or more $R^9$;

$R^7$ and $R^9$ are independently selected from halo, hydroxy, nitro, carboxy, carbamoyl, $C_{1-4}$alkyl, $C_{1-4}$alkoxy, $C_{1-4}$alkoxycarbonyl, $C_{1-4}$alkanoyl, $C_{1-4}$alkanoylamino, N,N-($C_{1-4}$alkyl)$_2$amino, N,N-($C_{1-4}$alkyl)$_2$carbamoyl, heterocyclyl, heterocyclylcarbonyl, carbocyclyl and carbocyclylcarbonylamino; wherein $R^7$ and $R^9$ may be independently optionally substituted on carbon by one or more $R^{11}$;

$R^8$ is selected from $C_{1-4}$alkyl, $C_{1-4}$alkylsulphonyl, N,N-($C_{1-4}$alkyl)$_2$sulpharnoyl, heterocyclyl and carbocyclyl; wherein $R^8$ may be optionally substituted on carbon by one or more $R^{12}$;

$R^{11}$ and $R^{12}$ are independently selected from halo, hydroxy, cyano, carbamoyl, methyl, methoxy, allyloxy, heterocyclyl and carbocyclyl.

More preferably A is —$NR^a$—, —O— or a direct bond; wherein $R^a$ is hydrogen, methyl, ethyl, propyl, isopropyl or allyl; wherein said methyl, ethyl, propyl, isopropyl or allyl may be optionally substituted by one or more $R^5$; wherein $R^3$ is methyl, ethyl, propyl, butyl, hexyl or allyl wherein $R^3$ may be optionally substituted by one or more $R^6$; or $R^3$ is selected from cyclopropyl, cyclopentyl, cyclohexyl, bicyclo[2,2,1] heptyl, phenyl, tetrahydropyranyl, morpholino, 2-oxopyrrolidiiyl, piperidinyl, pyrrolidinyl, azetidinyl, tetrahydrofuryl, 1,4-dioxa-8-azaspiro[4.5]decanyl, 1,1-dioxotetrahydrothienyl, 1,2,3,4,-tetrahydro-9H-pyrido[3,4-b]indole, decahydroquinolin-1-yl, 1,2,5,6-tetrahydropyridyl or piperazinyl; wherein $R^3$ maybe optionally substituted on carbon by one or more $R^7$; and wherein if any heterocyclyl contains an —NH— moiety that nitrogen may be optionally substituted by $R^8$;

$R^5$ is selected from cyano, methoxy, pyridyl;

$R^6$ is selected from hydroxy, cyano, amino, methoxy, pyridyl, 2-oxopyrrolidinyl, 1,2,4-tiazolyl, 1,1-dioxotetrahydrothienyl, thienyl, 2-oxooxazolidinyl, imidazolyl, 1,1-dioxothionioipholino, 2-oxo-1,2-dihydropyridyl, benzimidazolyl, pyrazolyl, succinimido, tetrahydrofuryl, 2,4-dioxothiazolidinyl, morpholino, furyl, pyridyloxy, pyridazinyloxy, cyclopentyl, cyclohexyl, plienyl, phenoxy, N-methylanilino, N,N-dimcthylamino, t-butoxycarhonylamino, mesyl, N,N-diinethylsulphanioylamino and isopropylsulphonylamino; wherein $R^6$ may be optionally substituted on carbon by one or more $R^9$;

$R^7$ is selected from fluoro, hydroxy, nitro, carboxy, carbamoyl, methyl, ethyl, propyl, methoxycarbonyl, ethoxycarbonyl, acetyl, acetamido, N,N-dimethylamino, N,N-dimethylcarbamoyl, N,N-diethylcarbamoyl, 1,4-dihydrooxazin-2-one, pyrazolyl, 2-oxo-2,3-dihydrobenzimidazolyl, pyridyl, 2,3-dihydro-2-oxobenzimidazolyl, morpholinocarbonyl, phenyl and cyclohexylcarbonylamino; wherein any $R^7$ may be optionally substituted on carbon by one or more $R^{11}$;

$R^9$ is selected from fluoro, chloro, hydroxy, methyl, methoxy, pyridyl and phenyl;

$R^8$ is selected from methyl, ethyl, propyl, pentyl, ethylsulphonyl, N,N-dimethylsulphamoyl, thieno[2,3-d]pyrimidinyl, pyrimidinyl, pyridyl and phenyl; wherein any $R^8$ may be optionally substituted on carbon by one or more $R^{12}$;

$R^{11}$ is selected from hydroxy, cyano, allyloxy, pyrrolidinyl, furyl and phenyl;

$R^{12}$ is selected from fluoro, cliloro, hydroxy, carbamoyl, methyl, methoxy, tetrahydrofuryl, morpholino and phenyl.

Preferably $R^3$ is $C_{1-10}$alkyl optionally substituted by one or more $R^6$; or $R^3$ is carbocyclyl or heterocyclyl wherein said carhocyclyl or heterocyclyl may be optionally substituted on carbon by one or more $R^7$; and wherein if said heterocyclyl contains an —NH— moiety that nitrogen may be optionally substituted by $R^8$.

More preferably $R^3$ is $C_{1-4}$alkyl optionally substituted by one or more $R^6$; or $R^3$ is carbocyclyl or heterocyclyl wherein said carbocyclyl or heterocyclyl may be optionally substituted on carbon by one or more $R^7$; and wherein if said heterocyclyl contains an —NH— moiety that nitrogen may be optionally substituted by $R^8$.

Particularly $R^3$ is methyl, ethyl, isopropyl or t-butyl; wherein said methyl, ethyl, isopropyl or t-butyl may be optionally-substituted by one or more $R^6$; or $R^3$ is cyclopropyl, phenyl, morpholino, piperazin-1-yl, tetrahydropyran-4-yl, piperid-l-yl, piperid-4-yl; wherein said cyclopropyl, phenyl, morpholino, piperazin-1-yl, tetrahydropyran-4-yl, piperid-1-yl or piperid-4-yl may be optionally substituted on carbon by one or more $R^7$; and wherein piperazin-1-yl and piperid-4-yl may be optionally substituted on nitrogen by $R^8$.

More particularly $R^3$ is methyl, ethyl, isopropyl or t-butyl; wherein said methyl, ethyl, isopropyl or t-butyl may be optionally substituted by one or more fluoro, hydroxy, cyano, amino, methoxy, pyridyl, morpholino, 2-pyrrolidinonyl, triazolyl, 1,1-dioxotetrahydrothienyl, 2-oxazolidinonyl, phenoxy, pyridyloxy, imidazolyl, 1,1-dioxothiomorpholino, N,N-dimethylamino, t-butyloxycarbonylaniino; or R³ is cyclopropyl, 4-nitrophenyl, morpholino,4-methylpiperazin-1-yl, tetrahydropyran-4-yl, 4-hydroxyniethylpiperid-1-yl or 1-methylpiperid-4-yl.

Particularly preferred R³ is methyl, cyanomethyl, 2-pyrrolidinon-1-ylmethyl, 1,1-dioxothiomorpholinomethyl, pyrid-3-yloxymethyl, 1,1-dioxotetrahydrothien-3-ylmelhyl, 2-oxazolidinon-3-ylmethyl, pyrid-4-ylmethyl, 1,2,4-triazol-1-ylmethyl, 1-phenoxyethyl, 2-imidazol-1-ylethyl, 2-N,N-dimethylaminoethyl, 2-1,2,4-triazol-1-ylethyl, 2-methoxyethyl, 2-pyrid-4-ylethyl, isopropyl, 1-pyrid-4-ylprop-2-yl, 2-aminoprop-2-yl, 2-hydroxy-3,3,3-trifluoroprop-2-yl, 1-morpholinoprop-2-yl, 2-(t-butoxycarbonylamino)prop-2-yl, t-butyl, cyclopropyl, 4-nitrophenyl, morpholino, 4-methylpiperazin-1-yl, tetrahydropyran-4-yl, 4-hydroxymethylpiperid-1-yl or 1-methylpiperid-4-yl.

More particularly preferred R³ is 1,1-dioxotetrahydrothien-3-ylmethyl, 1-phenoxyethyl, 2-pyrid-4-ylethyl, isopropyl, 1-pyrid-4-ylprop-2-yl, 1-morpholinoprop-2-yl, t-butyl, tetrahydropyran-4-yl or 1-methylpiperid-4-yl.

Preferably the group R³—A— is methyl, 2-oxo-pyrrolidin-1-ylmethyl, 1,2,4-triazo 1-1-yl methyl, 1,1-dioxotetrahydrothien-3-ylmethyl, 2-oxooxazolidin-3-ylmethyl, pyrid-3-yloxymethyl, 1,1-dioxothiomorpholinomethyl, cyanomethyl, 2-oxo-1,2-dihydropyrid-1-ylmethyl, 2-oxocyclopentylmethyl, sticcinimidomethyl, 3-benzyl-2-oxopyrrolidin-1-ylmethyl, 3-hydroxypyridazin-6-yloxymethyl, 2-pyrid-4-ylethyl, 2-methoxyethyl, 1-phenoxyethyl, 2-(1,2,4-triazol-1-yl)ethyl, 2-imidazol-1-ylethyl, succinimidoethyl, prop-2-yl, 3,3,3-trifluoro-2-hydroxyprop-2-yl, 1-morpholiioprop-2-yl, 1-pyrid-4-ylprop-2-yl, 2-aminoprop-2-yl, 2-(t-butoxycarbonylamino)prop-2-yl, 1-(1,2,4-triazol-1-yl)prop-2-yl, 2-pyrid-4-ylpropyl, t-butyl, 1,1,1-trifluorobut-3-yl, 1-hydroxyhex-2-yl, cyclopropyl, 3-hydroxybicyclo[2.2.1]hept-2-yl, 4-nitrophenyl, morpholino, 4-methylpiperazin-1-yl, tetrahydropyran-4-yl, 4-hydroxymethylpiperidin-1-yl, 1-methyl-2-oxopyrrolidin-4-yl, 2-(pyrrolidin-1-ylmethyl)pyrrolidinyl, 3-carbamoylpiperidin-1-yl, 3-hydroxyazetidin-1-yl, 2-(allyloxymethyl)morpholino, 4-(1,4-dihydrooxazin-2-one-3-yl)piperidin-1-yl, 4-(N,N-dimethylsulphamoyl)piperazin-1-yl, 4-hydroxyethylpiperidin-1-yl, 4-(tetrahydrofur-2-ylmethyl)piperazin-1-yl, 4-(3-methoxypropyl)piperazin-1-yl, 4-pyrid-4-ylpipcridin-1-yl, 4-pyrid-2-ylpiperazin-1-yl, 3-(N,N-dimethylamino)pyrrolidin-1-yl, 4-carboxypiperidin-1-yl, 1-methyl-2-oxo-5-phenyl-pyrrolidin-4-yl, 2-oxo-5,5-dimethyltetrahydrofur-4-yl, tetrahydrofur4-yl, 2,2-dimethyltetrahydropyran-4-yl, 1-benzyl-2-oxopyrrolidin-4-yl, 2-oxo-5-phenyltetrahydrofuryl, 2-(3-hydroxypropyl)piperidin-1-yl, 4-(2-carbamoylethyl)piperazin-1-yl, 3-oxo-4-(2-methoxyethyl)piperazin-1-yl, 4-(N,N-dimethylamino)-4-carbamoylpiperidin-1-yl, 4-(2-morpholinoethyl)piperazin-1-yl, 1,4-dioxa-8-azaspiro[4.5]decan-8-yl, 1,1-dioxotetrahydrothien-3-yl, 4-ethylsulphonylpiperazin-1-yl, 4-(thieno[2,3-d]pyrimidin-4-yl)piperazin-1-yl, 4-(2-hydroxyethyl)piperazin-1-yl, 4-carbamoylpiperidin-1-yl, 3-methyl-3-phenylpiperidin-1-yl, 2-benzyloxycarbonylpiperidin-1-yl, 4-(N,N-dimethylcarbamoyl)piperidin-1-yl, 3-(pyrid-4-yl)pyrrolidin-1-yl, 3-(pyrid-3-yl)pyrrolidin-1-yl, 4,4-difluoropiperidin-1-yl, 4-(2-methylpyrimidin-4-yl)piperazin-1-yl, 4-(2,3,5,6-tetrafluoropyrid-4-yl)piperazin-1-yl 4-(pyrimidin-4-yl)piperazin-1yl, 3-cyanomcthylpiperidin-1-yl, 4-cyclohexylcarbonylaminopiperidin-1-yl, 4-acetamidopiperidin-1-yl, 4(6-chloropyrimidin-4-yl)piperazin-1-yl, 4-(pent-3-yl)piperazin-1-yl, 1,2,5,6-tetrahydropyrid-1-yl, 1-methylpiperidin-1-yl, 2-methylpiperidin-1-yl, decahydroquinolin-1-yl, 3-ethoxycarbonyl-4-oxopiperidin-1-yl, 2-ethoxycarbonylpyrrolidin-1-yl, 4-acetylpiperidin-1-yl, 2-azabicyclo[2.2 1 ]hept-2-yl, 1,2,3,4,-tetrahydro-9H-pyrido[3,4-b]indol-2-yl, 4-(2,3-dihydro-2-oxobenzimidazol-1yl)piperidin-1-yl, 4-(2-methoxyphenyl)piperazin-1-yl, 4-methylpiperidin-1-yl, 4-(3-chlorophenyl)piperazin-1-yl, 4-(3-methoxyphenyl)piperazin-1-yl 4-(4-methoxyphenyl)piperazin-1-yl, 4-(4-chlorophenyl)pipcrazin-1-yl, 4-(2,3-dihydro-2-oxobenzimidazol1)-1,2,5,6-tetrahydropyrid1yl, 4-phenylpiperidin-1-yl, 4-(3-fur-2-ylpyrazol-5-yl)pieridin-1-yl, 2-pyrid-4-ylethylamino, 3-imidazol-1-ylpropylamino 4-hydroxycyclohexylamino, 2-(N,N-dimethylsulphamoylamino)ethylamino, 2-(isopropylsulphonylamino)ethylamino, 2-imidazol-5-ylethylamino, 2-mesylethylamino, 2-morpholinoethylamino, 1-methoxycarbonylcyclopropylamino, 1-benzylpyrrolidin-3-ylamino, 3-(N-methylanilino)propylamino, 2-(5-methyl-2,4-dioxothiazolidin-3-yl)ethylamino, 2-(t-butoxycarbonylamino)ethylamino, N,N-(N-methyl-N-pyrid-3-ylmethylaminopropyl)amino, 1-cyclohexylethylamino, N-methyl-N-(2-pyrid-4-ylethyl)amino, N-methyl-N-(2-pyrid-2-ylethyl)amino, N-methyl-N-(2-cyanoethyl)amino, N-methyl-N-(pyrid-3-yl methyl)amino, N-methyl-N-(2-N,N-dimethylaminoethyl)amino, N-methyl-N-(1-methylpiperidin4-yl)amino, N-methyl-N-(3-mesylpropyl)amino, N-methyl-N-(4-hydroxy-4-methyltetrahydropyran-3-yl)amino, N-(pyrid-3-ylmethyl)-N-(2-cyanocthyl)amino, N-methyl-N-(2-hydroxypropyl)amino, N-methyl-N-(2,2-dimethoxyethyl)amino, N-methyl-N-phenethylamino, N-methyl-N-(tetrahydrofur-2-ylmethyl)amino, N-methyl-N-(2-morpholinoethyl)amino, N-methyl-N-(6-methlylpyrid-2-ylmethyl)amino, N-methyl-N-(1methylpyrrolidinone-3-yl)amino, N-methyl-N-[2-(4-hydroxyphenyl)-2-hydroxyethyl]amino, N-methyl-N-(1-benzylpyrrolidin-3-yl)amino, N-methyl-N-[2-(1,2,4-triazol-1-yl)ethyl]amino, N-methyl-N-(fur-2-ylmethyl)amino, N-methyl-N-(benzimidazol-2-ylmethyl ethyl)amino, N-methyl-N-benzylamino, N-methyl-N-(2chlorobenzyl)amino, N-methyl-N-(3-chlorobenzyl)amino, N-methyl-V-(4-chlorobenzyl)amino, N-methyl-N-[2-(3,4-dimethoxypyrid-4-yl)ethyl]amino, N-methyl-N-(5-phenylpyrazol-3-ylmethyl)amino, N-methyl-N-(4-fluorobenzyl)amino, N-methyl-N-(2-methoxyphenylprop-2-yl)amino, N-ethyl-N-(pyrid-4-ylmethyl)amino, N-(2-methoxyethyl)-N-(pyrid-3-ylmethyl)amino, N-ethyl-N-(2-methxoyethyl)amino, N-(2-hydroxyethyl)-N-isopropylamino, N-(2-cyanoethyl)-N-(3-morpholinopropyl)amino, N-(2-cyanocthyl)-N-(thien-2-ylmethyl)amino, N-(2-cyanocthyl)-N-benzylamino, N-ethyl-N-(1-benzylpyrrolidin-3-yl)amino, N-ethyl-N-(1,1-dioxotetrahydrothicn-3-yl)amino, N-(2-pyrid-4-ylethyl)-N-cyclopropylamino, N-(2-hydroxy-2-pyrid-4-ylethyl)-N-isopropylamino, N-(4-hydroxycyclohexyl)-N-isopropylamino, N-allyl-N-(1,1-dioxotetrahydrothien-3-yl)amino, diallylamino, N-allyl-N-cyclopentylamino or N-benzyl-N-propylamino.

More preferably the group R³—A— is 1,1,1-trifluorobut-3-yl, 4-pyrid-4-ylpiperidin-1-yl, 4-pyrid-2-ylpiperidin-1-yl, 4-(2,3,5,6-tetrafluoropyrid-4-yl)piperazin1yl, N-methyl-N-(2-pyrid-4-ylethyl)amino or N-methyl-N-phenethylamino.

Preferably R5 and R⁶ are independently selected from halo, hydroxy, cyano, amino, $C_{1-6}$alkoxy, heterocyclyl, heterocyclyloxy, carbocyclyloxy, N,N-($C_{1-6}$alkyl)$_2$amino, $C_{1-6}$alkoxycarbonylamino.

More preferably $R^5$ and $R^6$ are independently selected from fluoro, hydroxy, cyano, amino, methoxy, pyridyl, morpholino, 2-pyrrolidinonyl, triazolyl, 1,1-dioxotetrahydrothienyl, 2-oxazolidinonyl, phenoxy, pyridyloxy, imidazolyl, 1,1-dioxothiomorpholino, N,N-dimethylamino, t-butyloxycarbonylamino.

Particularly $R^5$ and $R^6$ are independently selected from pyridyl, morpholino, 1,1-dioxotetrahydrothienyl or phenoxy.

Preferably $R^7$ is hydroxymethyl.

Preferably $R^8$ is selected from methyl.

Preferably $R^{11}$ is hydroxy.

In one aspect of the invention, preferably n is 0.

In another aspect of the invention, preferably n is 1.

In a further aspect of the invention preferably n is 2.

Preferably $R^4$ is $C_{1-4}$alkyl.

More preferably $R^4$ is methyl.

Particularly $R^4$ is 6-methyl.

In one aspect of the invention, preferably z is 0–2; wherein the values of $R^4$ may be the same or different.

In an additional aspect of the invention, preferably z is 0–1.

In another aspect of the invention, preferably z is 1.

In a further additional aspect of the invention, preferably z is 0.

In one aspect of the invention, preferably n is 2.

In an additional aspect of the invention, preferably n is 1.

In a further additional aspect of the invention, preferably n is 0.

Therefore in one aspect of the invention, there is provided a compound of formula (I) as depicted above wherein:

x is 0;
y is 0;
A is —$NR^a$—, —O— or a direct bond; wherein $R^a$ is hydrogen or $C_{1-4}$alkyl;
$R^3$ is $C_{1-4}$alkyl optionally substituted by one or more $R^6$; or $R^3$ is carbocyclyl or heterocyclyl wherein said carbocyclyl or heterocyclyl may be optionally substituted on carbon by one or more $R^7$; and wherein if said heterocyclyl contains an —NH— moiety that nitrogen may be optionally substituted by $R^8$;
$R^6$ is selected from halo, hydroxy, cyano, amino, $C_{1-6}$alkoxy, heterocyclyl, heterocyclyloxy, carbocyclyloxy, N,N-($C_{1-6}$alkyl)$_2$amino, $C_{1-6}$alkoxycarbonylamino; $R^7$ is hydroxymethyl;
$R^8$ is methyl; and
n is 0–2;
or a pharmaceutically acceptable salt, prodrug or solvate thereof;
with the provisos:
1) when $R^3$ is a nitrogen linked lieterocyclyl, A is a direct bond;
2) when n is 2, the group $R^3$—A—C(O)—NH— is not 2-acctamido, 3-acetamido, 2-propionamido, 2-(2-pthalimidoacetamido), 2-(3-pthalimidopropionamido), 2-(2-pthalimido-2-isopropylacetamido), 2-(2-aminoacetamido), 2-(3-aminopropionamido), 2-(2-amino-2-isopropylacetamido), 3-(2-pthalimidoacetamido), 3-(3-pthalimidopropionamido), 3-(2-pthalimido-2-isopropylacetamido), 3-(2-aminoacetamido), 3-(3-aminopropionamido), 3-(2-amino-2-isopropylacetamido) or 2-(3,3,3-trifluoro-2-hydroxy-2-methylpropionamido);
3) when n is 1, the group $R^3$—A—C(O)—NH— is not 3-acetamido, 3-(2-pthalimidoacetamido), 3-(3-pthalimidopropionamido), 3-(2-pthalimido-2-isopropylacetamido), 3-(2-aminoacetamido), 3-(3-aminopropionamido) or 3-(2-amino-2-isopropylacetamido);
4) when n is 0, the group $R^3$—A—C(O)—NH— is not 2-acctamido, 2-benzyloxycarbonylamino, 2-(2-pthalimidoacetamido), 2-(3-pthalimidopropionamido), 2-(2-pthalimido-2-isopropylacetamido), 2-(2-aminoacetamido), 2-(3-aminopropionamido), 2-(2-amino-2-isopropylacetamido), 3-(trifluoroacetamido), 3-benzyloxycarbonylamino or 4-t-butyloxycarbonylamino.

Therefore in a further aspect of the invention, there is provided a compound of formula (I) as depicted above wherein:

x is 0;
y is 0;
A is —$NR^a$—, —O— or a direct bond; wherein $R^a$ is hydrogen or methyl;
$R^3$ is methyl, cyanomethyl, 2-pyrrolidinon-1-ylmethyl, 1,1-dioxothiomorpholinomethyl, pyrid-3-yloxymethyl, 1,1-dioxotetrahydrothien-3-ylmethyl, 2-oxazolidinon-3-ylmethyl, pyrid-4-ylmethyl, 1,2,4-triazol-1-ylmethyl, 1-phenoxyethyl, 2-imidazol-1-ylethyl, 2-N,N-dimethylaminoethyl, 2-1,2,4-triazol-1-ylethyl, 2-methoxyethyl, 2-pyrid-4-ylethyl, isopropyl, 1-pyrid-4-ylprop-2-yl, 2-aminoprop-2-yl, 2-hydroxy-3,3,3-trifluoroprop-2-yl, 1-morpholinoprop-2-yl, 2-(t-butoxycarbonylamino)prop-2-yl, t-butyl, cyclopropyl, 4-nitrophenyl, morpholino, 4-methylpiperazin-1-yl, tetrahydropyran-4-yl, 4-hydroxymcthylpipcrid-1-yl or 1-methylpiperid-4-yl; and
n is 0–2;
or a pharmaceutically acceptable salt, prodrug or solvate thereof;
with the provisos:
1) when $R^3$ is morpholino, 4-methylpiperazin1or 4-hydroxymethylpiperid-1-yl, A is a direct bond;
2) when n is 2, the grotip $R^3$—A—C(O)—NH— is not 2-acetamido, 3-acetamido, or 2-(3,3,3-trifluoro-2-hydroxy-2-methylpropionamido);
3) when n is 1, the group $R^3$—A—C(O)—NH— is not 3-acetamido;
4) when n is 0, the group $R^3$—A—C(O)—NH— is not 2-acetamido.

Therefore in an additional aspect of the invention, there is provided a compound of formula (I) as depicted above wherein:

x is 0;
y is 0;
A is —$NR^a$— or a direct bond; wherein $R^a$ is methyl;
$R^3$ is 1,1-dioxotetrahydrothien-3-ylmethyl, 1-phenoxyethyl, 2-pyrid-4-ylethyl, isopropyl, 1-pyrid-4-ylprop-2-yl, 1-morpholinoprop-2-yl, t-butyl, tetrahydropyran-4-yl or 1-methylpiperid-4-yl; and
n is 0–2;
or a pharmaceutically acceptable salt, prodrug or solvate thereof.

Therefore in another aspect of the invention there is provided a compound of formula (I) (as depicted above) wherein:

X is a group of formula (A) (as depicted above) or a group of formula (B) (as depicted above);
R is halo, cyano or $C_{1-4}$alkyl;
A is —$NR^a$—, —O— or a direct bond; wherein $R^a$ is hydrogen, $C_{1-10}$alkyl or $C_{2-10}$alkenyl; wherein $R^a$ may be optionally substituted by one or more $R^5$;

R³ is C₁₋₁₀alkyl or C₂₋₁₀alkenyl wherein R³ maybe optionally substituted by one or more R⁶; or R³ is carbocyclyl or heterocyclyl wherein R³ may be optionally substituted on carbon by one or more R⁷; and wherein if said heterocyclyl contains an —NH— moiety that nitrogen may be optionally substituted by R⁸;

R⁵ and R⁶ are independently selected from hydroxy, cyano, amino, $C_{1-6}$alkoxy, heterocyclyl, heterocyclyloxy, carbocyclyl, carbocyclyloxy, carbocyclyl-N-($C_{1-6}$alkyl) amino, N,N-($C_{1-6}$alkyl)$_2$amino, $C_{1-6}$alkoxycarbonylamino, $C_{1-6}$alkylS(O)a wherein a is 0–2, N,N-($C_{1-6}$alkyl)$_2$ sulphamoylamino and $C_{1-6}$alkylsulphonylamino; wherein R⁵ and R⁶ may be independently optionally substituted on carbon by one or more R⁹;

R⁷ and R⁹ are independently selected from halo, hydroxy, nitro, carboxy, carbamoyl, $C_{1-4}$alkyl, $C_{1-4}$alkoxy, $C_{1-4}$alkoxycarbonyl, $C_{1-4}$alkanoyl, $C_{1-4}$alkanoylamino, N,N-($C_{1-4}$alkyl)$_2$amino, N,N-($C_{1-4}$alkyl)$_2$carbamoyl, heterocyclyl, heterocyclylcarbonyl, carbocyclyl and carbocyclylcarbonylamino; wherein R⁷ and R⁹ may be independently optionally substituted on carbon by one or more R¹¹;

R⁸ is selected from $C_{1-4}$alkyl, $C_4$alkylsulphonyl, N,N-($C_{1-4}$ alkyl)$_2$sulpharnoyl, heterocyclyl and carbocyclyl; wherein R⁸ may be optionally substituted on carbon by one or more R¹²;

R¹¹ and R¹² are independently selected from halo, hydroxy, cyano, carbamoyl, methyl, ethoxy, allyloxy, heterocyclyl and carbocyclyl;

R⁴ is $C_{1-4}$alkyl;

x is 0;

y is 0–1;

z is 1; and n is 0–2;

or a pharmaceutically acceptable salt, prodrug or solvate thereof, with the provisos when X is a group of formula (A):

1) when R³ is a nitrogen linked heterocyclyl, A is a direct bond;
2) when y is 0 and n is 2, the group R³—A—C(O)—NH— is not 2-acetamido, 3-acetamido, 2-propionamido, 2-(2-pthalimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetamido)2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(2-pthalimidoacetamido), 3-(3-pthalimidopropionamido), 3-(2-pthaliamnido-2-isopropylacetamido), 3-(2-pthaliamnido-2-isobutylacetamido), 3-(2-pthalimido-2-benzylacetarnido), 3-(2-aminoacetamido), 3-(3-aminopropionamido), 3-(2-amino-2-isopropylacetamido) or 3-(2-amino-2-benzylacetamido);
3) when y is 0 and n is 1, the group R³—A—C(O)—NH— is not 3-acetamido, 3-(2-pthalimidoacetaniido), 3-(3-pthalimidopropionamido), 3-(2-pthalimido-2-isopropylacetamido), 3-(2-pthaliamnido-2-isobutylacetamido), 3-(2-pthalimido-2-benzylacetamido), 3-(2-aminoacetamido), 3-(3-aminopropionamido), 3-(2-amino-2-isopropylacetamido), 3-(2-amino-2-isobutylacetamido) or 3-(2-amino-2-benzylacetamido);
4) when y is 0 and n is 0, the group R³—A—C(O)—NH— is not 2-benzamido, 2-acetamido, 2-benzyloxycarbonylamino, 2-(2-pthalimidpropionamido), 2-(3-pthalimidopropionamido), 2-(2-pthalimido-2-isopropylacetamido), 2-(2-pthalimido-2-isobutylacetamido), 2-(2-pthalimido2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-benzyloxycarbonylamino or 4-t-butyloxycarbonylamino;
5) when (R²)$_y$ is 1-cyano and n is 0, the group R³—A—C(O)—NH— is not 2-acetamido; 6) when (R²)$_y$ is 3-bromo and n is 0, the group R³—A—C(O)—NH— is not 2-acetamido or 2-benzamido;
7) when (R²)$_y$ is 1-bromo and n is 0, the group R³—A—C(O)—NH— is not 2-acetamido or 2-benzamido; and
8) when (R²)$_y$ is 1-chloro or 4-chloro and n is 0, the group R³—A—C(O)—NH— is not 2-acetamido.

Therefore in a further aspect of the invention there is provided a compound of formula (I) (as depicted above) wherein:

X is a group of formula (A) (as depicted above) or a group of formula (B) (as depicted above) in the 2-position of the dibenzothiophene ring;

R² is bromo, cyano or methyl;

A is —NR$^a$—, —O— or a direct bond; wherein R$^a$ is hydrogen, methyl, ethyl, propyl, isopropyl or allyl; wherein said methyl, ethyl, propyl, isopropyl or allyl may be optionally substituted by one or more R⁵;

R³ is methyl, ethyl, propyl, butyl, hexyl or allyl wherein R³ may be optionally substituted by one or more R⁶; or R³ is selected from cyclopropyl, cyclopentyl, cyclohexyl, bicyclo[2,2,1]heptyl, phenyl, tetrahydropyranyl, morpholino, 2-oxopyrrolidinyl, piperidinyl, pyrrolidinyl, azetidinyl, tetrahydrofuryl, 1,4-dioxa-8-azaspiro[4.5] decanyl, 1,1-dioxotetrahydrothienyl, 1,2,3,4,-tetrahydro-9H-pyrido[3,4-b]indole, decahydroquinolin-1-yl, 1,2,5,6-tetrahydropyridyl or piperazinyl; wherein R³ may be optionally substituted on carbon by one or more R⁷; and wherein if any heterocyclyl contains an —NH— moiety that nitrogen may be optionally substituted by R⁸;

R⁵ is selected from cyano, methoxy, pyridyl;

R⁶ is selected from hydroxy, cyano, amino, methoxy, pyridyl, 2-oxopyrrolidinyl, 1,2,4-triazolyl, 1,1-dioxotetrahydrothienyl, thienyl, 2-oxooxazolidinyl, imidazolyl, 1,1-dioxothiomorpholino, 2-oxo-1,2-dihydropyridyl, benzimidazolyl, pyrazolyl, succinimido, tetrahydrofuryl, 2,4-dioxothiazolidinyl, morpholino, furyl, pyridyloxy, pyridazinyloxy, cyclopentyl, cyclohexyl, phenyl, phenoxy, N-methylanilino, N,N-dimethylamino, t-butoxycarbonylamino, mesyl, N,N-dimethylsulphamoylamino and isopropylsulphonylamino; wherein R⁶ may be optionally substituted on carbon by one or more R⁹;

R7 is selected from fluoro, hydroxy, nitro, carboxy, carbamoyl, methyl, ethyl, propyl, methoxycarbonyl, ethoxycarbonyl, acetyl, acetamido, N,N-dimethylamino, N,N-dimethylcarbamoyl, N,N-diethylcarbarnoyl, 1,4-dihydrooxazin-2-one, pyrazolyl, 2-oxo-2,3-dihydrobenzimidazolyl, pyridyl, 2,3-dihydro-2-oxobenzimidazolyl, morpholinocarbonyl, phenyl and cyclohexylcarbonylamino; wherein any R⁷ may be optionally substituted on carbon by one or more R¹¹;

R⁹ is selected from fluoro, chloro, hydroxy, methyl, methoxy, pyridyl and phenyl;

R⁸ is selected from methyl, ethyl, propyl, pentyl, ethylsulphonyl, N,N-dimethylsulphamoyl, thieno[2,3-d] pyrimidinyl, pyrimidinyl, pyridyl and phenyl; wherein any R⁸ may be optionally substituted on carbon by one or more R¹²;

$R^{11}$ is selected from hydroxy, cyano, allyloxy, pyrrolidinyl, furyl and phenyl;

$R^{12}$ is selected from fluoro, chloro, hydroxy, carbamoyl, methyl, methoxy, tetrahydrofuryl, morpholino and phenyl;

$R^4$ is methyl;

$R^4$ is $C_{1-4}$alkyl;

x is 0;

y is 0–1;

z is 1; and n is 0–2;

or a pharmaceutically acceptable salt, prodrug or solvate thereof;

with the provisos when X is a group of formula (A):

1) when $R^3$ is a nitrogen linked heterocyclyl, A is a direct bond;
2) when y is 0 and n is 2, the group $R^3$—A—C(O)—NH— is not 2-acetamido, 2-propionamido, 2-(2-aminoacetamido), 2-(3-aminopropionamido), 2-(2-amino-2-isopropylacetamido) or 2-(2-amino2-benzylacetamido);
3) when y is 0 and n is 0, the group $R^3$—A—C(O)—NH— is not 2-benzamido, 2-acetamido, 2-benzyloxycarbonylamino, 2-(2-aminoacetamido), 2-(3-arninopropionamido), 2-(2-amino-2-isopropylacetamido) or 2-(2-amino-2-benzylacetamido);
4) when $(R^2)_y$ is 1-cyano and n is 0, the group $R^3$—A—C(O)—NH— is not 2-acetamido;
5) when $(R^2)_y$ is 3-bromo and n is 0, the group $R^3$—A—C(O)—NH— is not 2-acetamido or 2-benzamido; and
6) when $(R^2)_y$ is 1-bromo and n is 0, the group $R^3$—A—C(O)—NH— is not 2-acetamido or 2-benzamido.

In another aspect of the invention, preferred compounds of the invention are any one of the Examples or a pharmaceutically acceptable salt, prodrug or solvate thereof.

More preferred compounds of the invention are Examples 7, 19, 26, 27, 29, 30, 34, 35, 36, 37, 44, 45 and 47 or a pharmaceutically acceptable salt, prodrug or solvate thereof.

Further preferred compounds of the invention are Examples 19, 44, 50, 83, 105, 107 or 124 or a pharmaceutically acceptable salt, prodrug or solvate thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein $R^1$, $R^2$, $R^3$, A and n are, unless otherwise specified, as defined in formula (I)) comprises of:

Process a): for compounds of formula (I) wherein A is a direct bond and X is a group of formula (A); reacting an amine of formula (II):

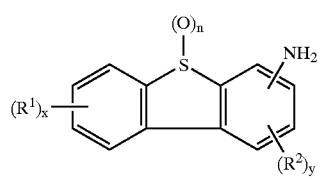

(II)

with an acid of formula (III):

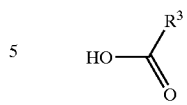

(III)

or an activated derivative thereof; or

Process b): for compounds of formula (I) wherein n >0; by oxidising a compound of formula (I) where n=0;

Process c): for compounds of formula (I) wherein A is —NR$^a$— and X is a group of formula (A); by reacting a compound of formula (IV):

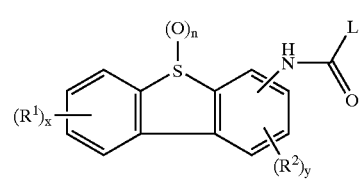

(IV)

wherein L is a displaceable group; with an amine of formula (V):

HNR$^a$R$^3$   (V)

Process d): for compounds of formula (I) wherein A is —NR$^a$— or —O— and X is a group of formula (A); reacting a compound of formula (II) with a compound of formula (VI):

(VI)

Process e): for compounds of formula (I) wherein A is —NH— and X is a group of formula (A); reacting a compound of formula (II) with an isocyanate of formula (VII):

O==N—R$^3$   (VII)

Process f: for compounds of formula (I) wherein X is a group of formula (B) reacting a compound of formula (II) with a compound of formula (VIII):

(VIII)

wherein L is a displaceable group;

and thereafter if necessary:

i) converting a compound of the formula (I) into another compound of the formula (I);
ii) removing any protecting groups;
iii) forming a pharmaceutically acceptable salt or in vivo hydrolysable ester.

L is a displaceable group. Suitable values for L are phenols for example p-nitrophenol or penta-fluorophenol.

Specific reaction conditions for the above reactions are as follows.

Process a) Amines of formula (II) and acids of formula (III) may be coupled together in the presence of a suitable coupling reagent. Standard peptide coupling reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

The amines of formula (II) and acids of formula (III) are commercially available or they are known compounds or they are prepared by processes known in the art.

Process b) Suitable oxidising agents include potassium permanganate, OXONE, sodium periodate, tert-butyl hydroperoxide (as solution in toluene), peracids (such as for example 3-chloroperoxybenzoic acid), hydrogen peroxide, TPAP (tetrapropylammonium perruthenate) or oxygen. The reaction may be conducted in a suitable solvent such as ether, dichloromethane, methanol, ethanol, water, acetic acid, or mixtures of two or more of these solvents. The reaction may conveniently be performed at a temperature in the range of −40 to 100° C.

Compounds of formula (I) where n=0 may be prepared by processes a) or c).

Process c) Compounds of formula (IV) and amines of formula (V) may be reacted together in the presence of a suitable base, for example triethylamine, pyridine, or 2,6-di-alkyl-pyridines such as 2,6-lutidine or 2,6-di-tert-butylpyridine, or excess (V), in a suitable solvent such as dichloromethane, EtOAc or tetrahydrofuran. The reaction may conveniently be performed at a temperature in the range of −40 to 50° C.

The compounds of formula (IV) may be prepared from amines of formula (II) by standard processes known in the art. Compounds of formula (V) are commercially available or they are known compounds or they are prepared by processes known in the art.

Process d) Compounds of formula (II) and compounds of formula (VI) may be reacted in the presence of a base, such as those described above, in a suitable solvent, such as dichloromethane, toluene or tetrahydrofuran. The reaction may conveniently be performed at a temperature in the range of −40 to 100° C.

Compounds of formula (VI) are commercially available or they are known compounds or they are prepared by processes known in the art.

Process e) Compounds of formula (II) and compounds of formula (VII) may be reacted in the presence of a suitable solvent, such as toluene, dichloromethane or tetrahydrofuran.

Compounds of formula (VII) are commercially available or they are known compounds or they are prepared by processes known in the art.

Process $f_i$: Compounds of formula (II) and compounds of formula (VIII) may be reacted together in the presence of a base, for example sodium t-butoxide, optionally in the presence of a catalyst for example tris(dibenzylidene-acetone)dipalladium(0) and S-2,2'-bis(diphenylphosphino)-1,1'-binapthyl (0.113 g, 0.18 mM) in a suitable solvent such as toluene.

Compounds of formula (VIII) are commercially available or they are known compounds or they are prepared by processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminum trichloride) under Friedel Crafts conditions; the introduction of an alkyl group using an alkyl halide and Lewis acid (such as aluminum trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl. The reader is referred to Advanced Organic Chemistry, $4^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimetliylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Biological Assays

The activity of compounds of the invention was measured in a neuropeptide Y5 receptor binding assay as follows. Compounds were also tested in binding assays for the neuropeptide $Y_1$ and neuropeptide $Y_2$ receptors. Activity against these 2 receptors is contraindicated for a neuropeptide Y5 antagonist.

a) Expression of Human Neuropeptide Y5 Receptor in High 5™ Insect Cells.

High 5™ insect cells were obtained from Invitrogen (catalogue N° B855-02) and stored in liquid nitrogen. Cells were revived from liquid nitrogen storage and grown at 28° C. in 100 ml ExCell 405 (JRH Biosciences) serum free medium in a 250 ml conical flask (Corning) agitated at 140 rpm in an Innova 4330 orbital shaker (New Brunswick Scientific). Cultures were routinely sub-cultured every 3–4 days.

High 5υ insect cells were transfected with the human NPY5 receptor as follows. PCR primers were designed against the huNPY5 receptor sequence, Genbank Accession Number U56079 [Gerald et. al. (1996) Nature 382, 168–171], but starting at base 56 through to base 1393, to express the protein 10 amino acid residues shorter at the amino terminal end [see Borowsky et. al. (1998) Regulatory Peptides 75–76, 45–53]. These primers were used to amplify the huNPY5 receptor from human placenta genomic DNA by PCR. This was then sub-cloned into pZERO2 (obtained from Invitrogen) for sequencing and re-cloned into pFASTBACI(obtained from GIBCO BRL Life Technologies) for expression. Human NPYr was isolated from pZERO2 on BanHI fragment and sub-cloned into pFastbacI on BamHI restriction site. The junctions were sequenced to ensure correct prior to expression.

A baculovirus containing the pFASTBACl was then generated using the Bac-to-Bac™ baculovirus expression system [Anderson et al (1996) FASEB Journal 10(6), 727–726] (obtained from GIBCO BRL Life Technologies) following the protocol supplied with this expression system by GIBCO BRL Life Technologies.

High 5™ insect cells were infected with the baculovirus to transfect the cells with the human neuropeptide Y5 receptor as follows: Batches were grown for membrane preparation by inoculating 5 L of ExCell 405™ medium in a 7 L Bioreactor (FT-Applikon) with $1.75 \times 10^9$ mid log High 5™ cells. After 2–3 days growth at 28° C. the mid log culture was infected with Baculovirus expressing the human NPY5 receptor at a multiplicity of infection (MOI) of 1.0. Cells (typically $1 \times 10^{10}$) were harvested 48 hours post infection by centrifugation (Heraeus Omnifuge 2.0RS 30 min, 296 g, 4° C.) and flash frozen in liquid nitrogen for storage at −80° C.

b) Membrane Preparation Procedure

The following buffer was prepared daily and stored at 4° C. 50 mM Tris HCl pH 7.4, 5 mM EDTA and 10% w.v. sucrose. A protease inhibitor cocktail (Boehringer Mannheim) was added to both buffers according to the manufacturers instruction. Cells were thawed rapidly in three times their packed cell volume of hypotonic buffer (3:1 mix of water and buffer) and lysed routinely on ice using five Vibra Cell Sonicator (Sonics and Materials Inc.) bursts of ten seconds for the High 5™ insect cells. The cell lysate (typically 10–15 ml) was carefully loaded onto a 10 ml 41% sucrose cushion which was topped off with lysis buffer and spun at 150,000 g for 1 hour at 4° C. in a Beckman Optima LE-80K Ultracentrifuge. The membrane fraction was carefully removed from the inter-phase and diluted at least four fold with lysis buffer. The membrane pellets were recovered by centrifugation at 150,000 g for 20 min at 4° C. in a Beckman Optima LE-80K Ultracentrifuge and re-suspended at $5 \times 10^7$ cell equivalents per ml. The re-suspended membranes were divided into working aliquots, routinely 1ml, flash frozen in liquid nitrogen and stored frozen at −80° C. until use.

Prior to use the 1 ml High 5™ membranes were thawed and resuspended in 8 ml binding buffer (see below). Membranes are used at approximately 7 µg/ml of protein per incubate.

c) Neuropeptide Y5 Receptor Binding Assay

The following reagents were used:

Binding buffer: 50 mM HEPES, 2.5 mM $CaCl_2$, 1 mM $MgCl_2$, 0.5% BSA, pH=7.4

Binding wash buffer: 50 mM HEPES, 2.5 mM $CaCl_2$, 1 mM $MgCl_2$, 0.5 M NaCl, 0.5% BSA, pH=7.4

Unifilter GFC filter plates: 50 µl of 0.5% polyethyleneimine was added to each well and left to equilibrate for four hours before use Incubation plates: 96 well polypropylene plates, siliconised prior to use Test Compounds: Compounds were dissolved in DMSO at a concentration of 1 mM. Final coneentration of DMSO in the assay did not exceed 1%.

Peptide PYY (pancreatic polypeptide Y)—10 µM stock solution in binding buffer.

IPYY—10 µCi/ml stock solution, diluted 1:10 dilution, into binding buffer.

Assays were performed in 96 well microtitre plates. 10 µl of diluted test compound was added to each well of a plate, followed by 80 µl of membranes and 10 µl of radiolabelled $^{125}$I PYY (0.01 µCi per well). Total and non-specific binding controls were included in each plate. The non-specific binding wells received 10 µl of Peptide PYY from the 10 µM stock solution, whilst the total binding wells received 10 µl of binding buffer. For each assay, a duplicate dose response of peptide PYY was included, top concentration 1 µM.

The plates were incubated for two hours at room temperature with mixing, and then filtered onto the pre-treated filter plates. The incubation plates were washed twice with 150 μl of cold binding wash buffer per well, then the filter plates were further washed with approximately 2.5 ml per well. The filter plates were dried overnight at room temperature, the bottoms were sealed, and 20 μl of Scintillant (Microscint 40, Canberra Packard) was added to each well. The tops of the plates were sealed and the plates were counted for 1 minute on a protocol set up for $^{125}$I on a 96 well plate liquid scintillation counter (Top Count, Canberra Packard).

Compounds were considered to be active if they inhibited the binding by more than 50% at a concentration of 10 μM. Dose responses were carried out on all compounds found to be active (8 point curves in duplicate).

Although the pharmacological properties of the compounds of the formula (I) vary with structural change as expected, in general compounds of the formula (I) possess an $IC_{50}$ in the above test in the range, for example, 0.0002 to 200 μM. For example, the compound of Example 16 has an $IC_{50}$ for the neuropeptide Y5 receptor of 94 nM.

In order to use a compound of the formula (1) or a pharmaceutically acceptable salt, prodrug or solvate thereof, for the therapeutic treatment (including prophylactic treatment) of mammals including humans, it is normally formulated in accordance with standard pharmaceutical practice as a pharmaceutical composition.

Therefore according to a further aspect of the invention there is provided a pharmaceutical composition which comprises a compound of the formula (I) or a pharmaceutically acceptable salt, prodrug or solvate thereof, as defined herein before in association with a pharmaceutically acceptable diluent or carrier.

According to another aspect of the invention there is provided a pharmaceutical composition comprising a compound of formula (I), or a pharmaceutically acceptable salt, prodrug or solvate thereof, in association with a pharmaceutically acceptable diluent or carrier for the treatment of disorders mediated by the neuropeptide Y5 receptor in a warm-blooded animal, such as a human being in need of such treatment.

To treat disorders mediated by the neuropeptide Y5 receptor neuropeptide Y5 receptor agonists or antagonists can be administered.

According to an additional aspect of the invention there is provided a pharmaceutical composition comprising a compound of formula (I), or a pharmaceutically acceptable salt, prodrug or solvate thereof, in association with a pharmaceutically acceptable diluent or carrier for the treatment of eating disorders in a warm-blooded animal, such as a human being.

According to an additional aspect of the invention there is provided a pharmaceutical composition comprising a compound of formula (I), or a pharmaceutically acceptable salt, prodrug or solvate thereof, in association with a pharmaceutically acceptable diluent or carrier for promoting weight loss in a warm-blooded animal, such as a human being.

Examples of disorders mediated by the neuropeptide Y5 receptor are eating disorders. Examples of eating disorders include obesity, bulimia or anorexia. Examples of eating disorders include obesity and related disorders, bulimia or anorexia. Examples of "related disorders" are diabetes dyslipidaemia, hypertension and sleep disturbances. Preferably "related disorders" refers to diabetes.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyetliylene sorbitol monoolcatc, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of al anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on. Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

The compounds of this invention may be used in combination with other drugs and therapies used in the treatment of disease states which would benefit from antagonism at the neuropeptide Y5 receptor. For example, the compounds of the formula (I) could be used in combination with drugs and therapies used in the treatment of eating disorders.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the formula (I) are primarily of value as therapeutic agents for use in a warm-blooded animal, such as a human being, they are also useful whenever it is required to antagonise binding at the neuropeptide Y5 receptor. Thus, they are useful as pharmacological standards for use in the development of new biological tests and in the search for new pharmacological agents.

According to an additional aspect of the invention there is provided a compound of formula (IA):

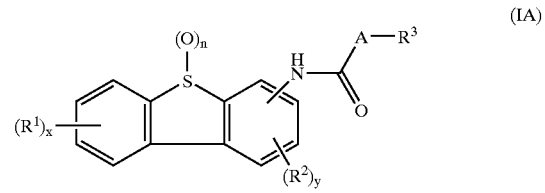

wherein:
$R^1$ is cyano, halo, trifluoromethyl, trifluoromethoxy, $C_{1-4}$alkyl, $C_{-4}$alkoxy, N-($C_{1-4}$alkyl)amino or N,N-($C_{1-4}$alkyl)$_2$amino;
$R^2$ is halo, cyano, hydroxy, trifluoromethyl, trifluoromethoxy, $C_{1-4}$alkyl or $C_{1-4}$alkoxy;
A is —$NR^a$—, —O— or a direct bond; wherein $R^a$ is hydrogen, $C_{1-4}$alkyl, $C_{2-10}$alkenyl, $C_{2-10}$alkynyl; wherein said C$_{2-10}$alkyl, C$_2$loalkenyl, C$_{2-10}$ alkynyl may be optionally substituted by one or more R$^4$;

R$^3$ is hydrogen, C$_{1-10}$alkyl, C$_{2-10}$alkenyl or C$_{2-10}$alkynyl wherein said C$_{1-10}$alkyl, C$_{2-10}$alkenyl, C$_{2-10}$alkynyl may be optionally substituted by one or more R$^5$; or R$^3$ is carbocyclyl or heterocyclyl wherein said carbocyclyl or heterocyclyl may be optionally substituted on carbon by one or more R$^6$; and wherein if said heterocyclyl contains an —NH— moiety that nitrogen may be optionally substituted by R$^7$;

R$^4$ and R$^5$ are independently selected from halo, hydroxy, cyano, carbamoyl, ureido, amino, nitro, carboxy, carbamoyl, mercapto, sulphamoyl, C$_{1-6}$alkoxy, C$_{1-6}$alkanoyl, C$_{1-6}$alkanoyloxy, C$_{1-6}$alkanoylamino, C$_{2-6}$alkenyloxycarbonyl, C$_{1-6}$alkoxycarbonyl, heterocyclyl, heterocyclyloxy, heterocyclylcarbonyl, heterocyclyloxycarbonyl, carbocyclyl, carbocyclyloxy, carbocyclylcarbonyl, carbocyclyloxycarbonyl, N-(C$_{1-6}$alkyl)amino, N,N-(C$_{1-6}$alkyl)$_2$amino, C$_{1-6}$alkoxycarbonylamino, N-(C$_{1-6}$alkyl)carbamoyl, N,N-(C$_{1-6}$alkyl)$_2$carbamoyl, C$_{1-6}$alkylS(O)$_a$ wherein a is 0–2, N-(C$_{1-6}$alkyl)sulphamoyl and N,N-(C$_{1-6}$alkyl)$_2$sulphamoyl; wherein any C$_{1-6}$alkyl, heterocyclyl or carbocyclyl may be optionally substituted on carbon by one or more R$^6$; and wherein if said heterocyclyl contains an —NH— moiety that nitrogen may be optionally substituted by R$^7$;

R$^6$ is selected from halo, hydroxy, cyano, carbamoyl, ureido, trifluoromethyl, trifluoromethoxy, amino, nitro, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkoxycarbonyl, C$_{2-4}$alkenyloxycarbonyl, C$_{1-4}$alkanoyl, C$_{1-4}$alkanoylamino, C$_{1-4}$alkanoyloxy, N-(C$_{1-4}$alkyl)amino, N,N-(C$_{1-4}$alkyl)$_2$amino, N-(C$_{1-4}$alkyl)carbamoyl, N,N-(C$_{1-4}$alkyl)$_2$carbamoyl, C$_{1-4}$alkylS(O)$_a$ wherein a is 0–2, N-(C$_{1-4}$alkyl)sulphamoyl, N,N-(C$_{1-4}$alkyl)$_2$sulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl; wherein any C$_{1-4}$alkyl, carbocyclyl and heterocyclyl may be optionally substituted on carbon by one or more R$^8$;

R$^7$ is selected from C$_{1-4}$alkyl, C$^{1-4}$alkanoyl, C$_{1-4}$alkylsulphonyl, C$_{1-4}$alkoxycarbonyl, carbamoyl, N-(C$_{1-4}$ alkyl)carbamoyl, N,N-(C$_{1-4}$alkyl)$_2$carbamoyl, benzyl, benzoyl, phenylsulphonyl and phenyl;

R$^8$ is selected from halo, hydroxy, cyano, carbamoyl, ureido, amino, nitro, carboxy, carbamoyl, mercapto, sulphamoyl, inethoxy, methoxycarbonyl, formyl, acetyl, formamido, acetylamino, acetoxy, methylamino, dimethylamino, N-metbylcarbamoyl, N,N-dimethylcarbamoyl, methylthio, methylsulphinyl, mesyl, N-methylsulphamoyl, N,N-dimethlylsulphamoyl, heterocyclyl, heterocyclyloxy, hctcrocyclylcarbonyl, heterocyclyloxycarbonyl, carbocyclyl, carbocyclyloxy, carbocyclylcarbonyl and carbocyclyloxycarbonyl;

x is 0–4; wherein the values of R$^1$ may be the same or different;

y is 0–3; wherein the values of R$^2$ may be the same or different; and n is 0–2;

or a pharmaceutically acceptable salt, prodrug or solvate thereof; with the provisos:

1) when R$^3$ is a nitrogen linked heterocyclyl, A is a direct bond;

2) when x and y are 0 and n is 2, the group R$^3$—A—C(O)—NH— is not 2-formamido, 2-acetamido, 2-propionamido, 2-(2-pthalimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(2-pthalimidoacetamido), 3-(3-pthalimidopropionamido), 3-(2-pthalimido-2-isopropylacetamido), 3-(2-pthalimido-2-isobutylacetamido), 3-(2-pthalimido-2-benzylacetamido), 3-(2-aminoacetamido), 3-(3-aminopropionamido), 3-(2-amino-2-isopropylacetamido), 3-(2-amino-2-benzylacetamido) or 2-(3,3,3-trifluoro-2-hydroxy-2-methylpropionamido);

3) when x and y are 0 and n is 1, the group R$^3$—A—C(O)—NH— is not 3-(2-pthalimidoacetamido), 3-(3-pthalimidopropionamido), 3-(2-pthalimido-2-isopropylacctamido), 3-(2-pthalimido-2-isobutylacetamido), 3-(2-pthalimido-2-benzylacetamido), 3-(2-aminoacetamido), 3-(3-aminopropionamido), 3-(2-amino-2-isopropylacetamido), 3-(2-amino-2-isobutylacetaniido) or 3-(2-amino-2-benzylacetamido);

4) when x and y are 0 and n is 0, the group R$^3$—A—C(O)—NH— is not 2-(2-pthalimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetamido), 2-(2-aminoacetamido), 2-(3-aminopropionamido), 2-(2-amino-2-isopropylacetamido), 2-(2-amino-2-isobutylacetamido) or 2-(2-amino-2-benzylacetarnido);

5) when (R$^1$)$_x$ is 7-fluoro, y is 0 and n is 2, the group R$^3$—A—C(O)—NH— is not 3-acetamido; or a pharmaceutically acceptable salt, prodrug or solvate thereof, for use as a medicament.

In particular additional aspect of the invention there is provided a compound of formula (IA) which is 2-acetamidodibenzothiophene or a pharmaceutically acceptable salt, prodrug or solvate thereof, for use as a medicament.

According to an additional aspect of the invention there is provided a compound of formula (IA'):

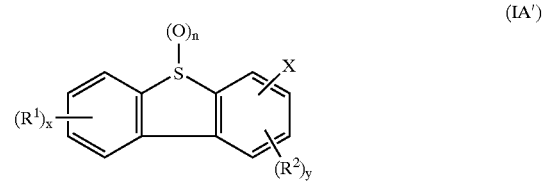

(IA')

wherein:

X is a group of formula (A) or (B):

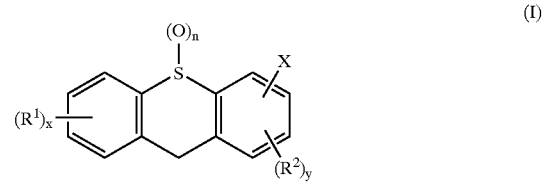

(I)

R$^1$ is cyano, halo, trifluoromethyl, trifluoromethoxy, C$_{1-4}$alkyl, Cl-$_4$alkoxy, N-(C$_{1-4}$alkyl)amino or N,N-(C$_{1-4}$alkyl)$_2$amino;

R$^2$ is halo, cyano, hydroxy, trifluoromethyl, trifluoromethoxy, C$_{1-4}$alkyl or C$_{1-4}$alkoxy;

A is —NR$^a$—, —O— or a direct bond; wherein R$^a$ is hydrogen, C$_{1-10}$alkyl, C$_{2-10}$alkenyl, C$_{2-10}$alkynyl; wherein R$^a$ may be optionally substituted by one or more R$^5$;

$R^3$ is hydrogen, $C_{1-10}$alkyl, $C_{2-10}$alkenyl or $C_{2-10}$alkynyl wherein $R^3$ may be optionally substituted by one or more $R^6$; or $R^3$ is carbocyclyl or heterocyclyl wherein $R^3$ may be optionally substituted on carbon by one or more $R^7$; and wherein if said heterocyclyl contains an —NH— moiety that nitrogen may be optionally substituted by $R^8$;

$R^4$ is halo, nitro, cyano, hydroxy, trifluoromethyl, trifluoromethoxy, amino, carboxy, carbamoyl, mercapto, sulphamoyl, $C_{1-4}$alkoxycarbonyl, $C_{1-4}$alkyl, $C_{2-10}$alkenyl, $C_{2-10}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, N-(carbocyclyl)carbamoyl, N,N-(carbocyclyl)$_2$carbamoyl, N-(heterocyclyl)carbamoyl, N,N-(heterocyclyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)$_2$sulphamoyl, $C_{1-4}$alkylsulphonylamino or (nitrogen-linked heterocyclic ring)carbonyl;

$R^5$ and $R^6$ are independently selected from halo, hydroxy, cyano, carbamoyl, ureido, amino, nitro, carboxy, carbarnoyl, mercapto, sulphamoyl, aminosulphamoyl, $C_{1-6}$alkoxy, $C_{1-6}$alkanoyl, $C_{1-6}$alkanoyloxy, $C_{1-6}$alkanoylamino, $C_{2-6}$alkenyloxycarbonyl, $C_{1-6}$alkoxycarbonl, heterocyclyl, heterocyclyloxy, heterocyclylamino, heterocyclyl-N-($C_{1-6}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-6}$alkyl)amino, carbocyclylsulphonyl, carbocyclylcarbonyl, carbocyclylcarbonylamino, carbocyclyloxycarbonyl, N-($C_{1-6}$alkyl)amino, N,N-($C_{1-6}$alkyl)$_2$amino, $C_{1-6}$alkoxycarbonylarnino, N-($C_{1-6}$alkyl)carbamoyl, N,N-($C_{1-6}$alkyl)$_2$carbamoyl, $C_{1-6}$alkylS(O)$_a$ wherein a is 0–2, N-(Cl6alkyl)sulphamoylamino N,N-($C_{1-6}$alkyl)$_2$sulphamoylamino, $C_{1-6}$alkylsulphonylamino, ($C_{1-6}$alkyl)sulphonyl-N-($C_{1-6}$alkyl)amino, N-($C_{1-6}$alkyl)sulphamoyl and N,N-($C_{1-6}$alkyl)$_2$sulphamoyl; wherein $R^5$ and $R^6$ may be optionally substituted on carbon by one or more $R^9$; and wherein if said heterocyclyl contains an —NH— moiety that nitrogen may be independently optionally substituted by $R^{10}$;

$R^7$ and $R^9$ are independently selected from halo, hydroxy, cyano, carbamoyl, ureido, trifluoromethyl, trifluoromethoxy, amino, nitro, carboxy, carbamoyl, mercapto, sulphamoyl, aminosulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{1-4}$alkoxycarbonylamino, $C_{2-4}$alkenyloxycarbonyl, $C_{1-4}$alkanoyl, $C_{1-4}$alkanoylamino, $C_{1-4}$alkanoyloxy, N-($C_{1-4}$alkyl)amino, N,N-($C_{1-4}$alkyl)$_2$amino, N-($C_{1-4}$alkyl)carbamoyl, N,N-($C_{1-4}$alkyl)$_2$carbamoyl, $C_{1-4}$alkylS(O)a wherein a is 0–2, N-($C_{1-4}$alkyl)sulphamoylamino, N,N-($C_{1-4}$alkyl)$_2$sulphamoylamino, ($C_{1-4}$ alkyl)sulphonylamino, ($C_{1-4}$alkyl)sulphonyl-N-($C_{1-4}$alkyl)amino, N-($C_{1-4}$alkyl)sulphamoyl, N,N-($C_{1-4}$alkyl)$_2$sulphamoyl, heterocyclyl, heterocyclyloxy, heterocyclylamino, heterocyclyl-N-($C_{1-4}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-4}$alkyl)amino, carboocyclylsulphonyl, carbocyclylcarbonyl, carbocyclylcarbonylamino, and carbocyclyloxycarbonyl; wherein $R^7$ and $R^9$ may be independently optionally substituted on carbon by one or more $R^{11}$;

$R^8$ and $R^{10}$ are independently selected from $C_{1-4}$alkyl, $C_{1-4}$alkanoyl, sulphamoyl, $C_{1-4}$alkylsulphonyl, $C_{1-4}$alkoxycarbonyl, carbamoyl, N-($C_{1-4}$alkyl)carbamoyl, N,N-($C_4$alkyl)$_2$carbamoyl, N-($C_{1-4}$alkyl)sulpharnoyl, N,N-($C_{1-4}$alkyl)$_2$sulphamoyl, heterocyclyl, heterocyclylcarbonyl, heterocyclyloxycarbonyl, heterocyclylsulphonyl, carbocyclyl, carbocyclylcarbonyl, carbocyclyloxycarbonyl and carbocyclylsulphonyl; wherein $R^8$ and $R^{10}$ may be independently optionally substituted on carbon by one or more $R^{12}$;

$R^{11}$ and $R^{12}$ are independently selected from halo, hydroxy, cyano, carbamoyl, ureido, amino, nitro, carboxy, carbamoyl, mercapto, sulphamoyl, methyl, ethyl, vinyl, allyl, methoxy, ethoxy, vinyloxy, allyloxy, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-d imethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

x is 0–4; wherein the values of $R^1$ may be the same or different;

y is 0–3; wherein the values of $R^2$ may be the same or different;

z is 0–3; wherein the values of $R^4$ may be the same or different; and n is 0–2;

or a pharmaceutically acceptable salt, prodrug or solvate thereof;

with the provisos when X is a group of formula (A):
1) when $R^3$ is a nitrogen linked heterocyclyl, A is a direct bond;
2) when x and y are 0 and n is 2, the group $R^3$—A—C(O)—NH— is not 2-formamido, 2-acctamido, 2-propionamido, 2-(2-pthalimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetarnido), 3-(2-pthalimidoacetamido), 3-(3-pthalimidopropionamido), 3-(2-pthalimido-2-isopropylacetamido), 3-(2-pthalimido-2-isobutylacetamido), 3-(2-pthalimido-2-benzylacetamido), 3-(2-aminoacetamido), 3-(3-aminopropionamido), 3-(2-amino-2-isopropylacetamido), 3-(2-amino-2-benzylacetamido) or 2-(3,3,3-trifluoro-2-hydroxy-2-methylpropionamido);
3) when x and y are 0 and n is 1, the group $R^3$—A—C(O)—NH— is not 3-(2-pthalimidoacetamido), 3-(3-pthalimidopropionamido), 3-(2-pthalimido-2-isopropylacetamido), 3-(2-pthalimido-2-isobutylacetamido), 3-(2-pthalimido-2-benzylacetamido), 3-(2-aminoacetamido), 3-(3-aminopropionamido), 3-(2-amino-2-isopropylacetaamnido), 3-(2-amino-2-isobutylacetamido) or 3-(2-amino-2-benzyl acetamido);
4) when x and y are 0 aid n is 0, the group $R^3$—A—C(O)—NH— is not 2-(2-pthalimidoacetamido), 2-(3-pthalimidopropionamido), 2-(2-pthalimido-2-isopropylacetamido), 2-(2-pthalimido-2-isobutylacetamido), 2-(2-pthalimido-2-benzylacetarnido), 2-(2-aminoacetamido), 2-(3-aminopropionamido), 2-(2-amino-2-isopropylacetamido), 2-(2-amino-2-isobutylacetamido) or 2-(2-amino-2-benzylacetarnido);
5) when $(R^1)_x$ is 7-fluoro, y is 0 and n is 2, the group $R^3$—A—C(O)—NH— is not 3-acetamido;

or a pharmaceutically acceptable salt, prodrug or solvate thereof, for use as a medicament.

According to a further feature of the invention there is provided a method of treating disorders mediated by the neuropeptide Y5 receptor in a warm-blooded animal, such as a human being, in need of such treatment which comprises administering to said animal a therapeutically effective amount of a compound of formula (IB):

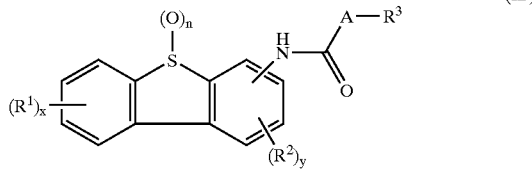

(IB)

wherein:

R¹ is cyano, halo, trifluoromethyl, trifluoromethoxy, $C_{1-4}$alkyl, $C_{1-4}$alkoxy, N-($C_{1-4}$alkyl)amino or N,N-($C_{1-4}$ alkyl)$_2$amino;

R² is halo, cyano, hydroxy, trifluoromethyl, trifluoromethoxy, $C_{1-4}$alkyl or $C_{1-4}$alkoxy;

A is —NR$^a$—, —O— or a direct bond; wherein R$^a$ is hydrogen, $C_{1-10}$alkyl, $C_{2-10}$alkenyl, $C_{2-10}$alkynyl; wherein said $C_{1-10}$alkyl, $C_{2-1}$alkenyl, $C_{2-10}$alkynyl may be optionally substituted by one or more R⁴;

R³ is hydrogen, $C_{1-10}$alkyl, $C_{2-10}$alkenyl or $C_{2-10}$alkynyl wherein said $C_{1-10}$alkyl, $C_{2-10}$alkenyl, $C_{2-10}$alkynyl may be optionally substituted by one or more R⁵; or R³ is carbocyclyl or heterocyclyl wherein said carbocyclyl or heterocyclyl may be optionally substituted on carbon by one or more R⁶; and wherein if said heterocyclyl contains an —NH— moiety that nitrogen may be optionally substituted by R⁷;

R⁴ and R⁵ are independently selected from halo, hydroxy, cyano, carbamoyl, ureido, amino, nitro, carboxy, carbamoyl, mercapto, sulphamoyl, $C_{1-6}$alkoxy, $C_{1-6}$alkanoyl, $C_{1-6}$alkanoyloxy, $C_{1-6}$alkanoylamino, $C_{2-6}$alkenyloxycarbonyl, $C_{1-6}$alkoxycarbonyl, heterocyclyl, heterocyclyloxy, heterocyclylcarbonyl, heterocyclyloxycarbonyl, carbocyclyl, carbocyclyloxy, carbocyclylcarbonyl, carbocyclyloxycarbonyl, N-($C_{1-6}$ alkyl)amino, N,N-($C_{1-6}$alkyl)$_2$amino, $C_{1-6}$alkoxycarbonylamino, N-($C_{1-6}$alkyl)carbamoyl, N,N-($C_{1-6}$alkyl)$_2$carbamoyl, $C_{1-6}$alkyS(O)$_a$ wherein a is 0–2, N-($C_{1-6}$alkyl)sulpharnoyl and N,N-($C_{1-6}$alkyl)$_2$sulphamoyl; wherein any $C_{1-6}$alkyl, heterocyclyl or carbocyclyl may be optionally substituted on carbon by one or more R⁶; and wherein if said heterocyclyl contains an —NH— moiety that nitrogen may be optionally substituted by R⁷;

R⁶ is selected from halo, hydroxy, cyano, carbamoyl, urcido, trifluoroinethyl, trifluoromethoxy, amino, nitro, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{2-4}$alkenyloxycarbonyl, $C_{1-4}$alkanoyl, $C_{1-4}$alkanoylamino, $C_{1-4}$alkanoyloxy, N-($C_{1-4}$alkyl)amino, N,N-($C_{1-4}$alkyl)$_2$ amino, N-($C_{1-4}$alkyl)carbamoyl, N,N-($C_{1-4}$alkyl)$_2$ carbamoyl, $C_{1-4}$alkylS(O)$_a$ wherein a is 0–2, N-($C_{1-4}$alkyl) sulphamoyl, N,N-($C_{1-4}$alkyl)$_2$sulphamoyl, heterocyclyl, heterocyclylox y, heterocyclylcarbonyl, hetcrocyclyloxycarbonyl, carbocyclyl, carbocyc lyloxy, carbocyclylcarbonyl and carbocyclyloxycarbonyl; wherein any $C_{1-4}$alkyl, carbocyclyl and heterocyclyl may be optionally substituted on carbon by one or more R$_8$;

R⁷ is selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$ alkyl)$_2$carbamoyl, benzyl, benzoyl, phenylsulphonyl and phenyl;

R⁸ is selected from halo, hydroxy, cyano, carbamoyl, ureido, amino, nitro, carboxy, carbamoyl, mercapto, sulphamoyl, methoxy, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, heterocyclyl, heterocyclyloxy, heterocyclylcarbonyl, heterocyclyloxycarbonyl, carbocyclyl, carbocyclyloxy, carhocyclylcarbonyl and carbocyclyloxycarbonyl;

x is 0–4; wherein the values of R¹ may be the same or different;

y is 0–3; wherein the values of R² may be the same or diffcrent; and n is 0–2;

or a pharmaceutically acceptable salt, prodrug or solvate thereof;

with the providing that when R³ is a nitrogen linked heterocyclyl, A is a direct bond;

or a pharmaceutically acceptable salt, prodrug or solvate thereof.

According to a particular feature of the invention there is provided a method for promoting weight loss in a warm-blooded animal, such as a human being, in need of such treatment which comprises administering to said animal a therapeutically effective amount of a compound of formula (IB) or a pharmaceutically acceptable salt, prodrug or solvate thereof.

According to a further feature of the invention there is provided a method of treating disorders mediated by the neuropeptide Y5 receptor in a warm-blooded animal, such as a human being, in need of such treatment which comprises administering to said animal a therapeutically effective amount of a compound of formula (IB'):

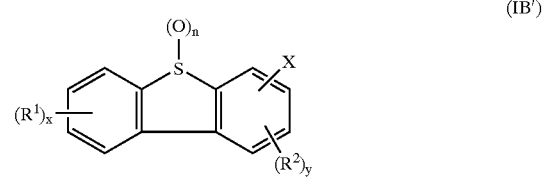

(IB')

wherein:

X is a group of formula (A) or (B):

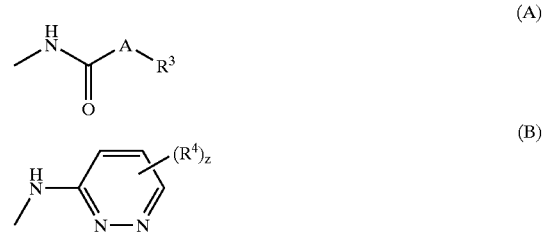

R¹ is cyano, halo, trifluoromethyl, trifluoromethoxy, $C_{1-4}$alkyl, $C_{1-4}$alkoxy, N-($C_{1-4}$alkyl)amino or N,N-($C_{1-4}$ alkyl)$_2$amino;

R² is halo, cyano, hydroxy, trifluoromethyl, trifluoromethoxy, $C_{1-4}$alkyl or $C_{1-4}$alkoxy;

A is —NR$^a$—, — or a direct bond; wherein R$^a$ is hydrogen, $C_{1-10}$alkyl, $C_{2-10}$alkenyl, $C_{2-10}$alkynyl; wherein R$^a$ may be optionally substituted by one or more R⁵;

R³ is hydrogen, $C_{1-10}$alkyl, $C_{2\ 10}$alkenyl or $C_{2-10}$alkynyl wherein R³ may be optionally substituted by one or more R⁶; or R³ is carbocyclyl or heterocyclyl wherein R³ may be optionally substituted on carbon by one or more R⁷; and wherein if said heterocyclyl contains an —NH— moiety that nitrogen may be optionally substituted by R⁸;

R⁴ is halo, nitro, cyano, hydroxy, trifluoromethyl, trifluoromethoxy, amino, carboxy, carbamoyl, mercapto, sulphamoyl, $C_{1-4}$alkoxycarbonyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbarnoyl, N-(carbocyclyl)carbamoyl, N,N-(carbocyclyl)$_2$carbamoyl, N-(heterocyclyl)carbamoyl, N,N-(heterocyclyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)$_2$sulphamoyl, $C_{1-4}$alkylsulphonylamino or (nitrogen-linked heterocyclic ring)carbonyl;

R⁵ and R⁶ are independently selected from halo, hydroxy, cyano, carbamoyl, ureido, amino, nitro, carboxy, carbamoyl, mercapto, sulphamoyl, aminosulphamoyl, $C_{1-6}$alkoxy, $C_{1-6}$alkanoyl, $C_{1-6}$alkanoyloxy, $C_{1-6}$alkanoylamino, $C_{2-6}$alkenyloxycarbonyl, $C_{1-6}$alkoxycarbonyl, heterocyclyl, heterocyclyloxy, heterocyclylamino, heterocyclyl-N-($C_{1-6}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-6}$alkyl)amino, carbocyclylsulphonyl, carbocyclylcarbonyl, carbocyclylcarbonylamino, carbocyclyloxycarbonyl, N-($C_{1-6}$alkyl)amino, N,N-($C_{1-6}$alkyl)$_2$amino, $C_{1-6}$alkoxycarbonylamino, N-($C_{1-6}$alkyl) carbamoyl, N,N-($C_6$alkyl)$_2$carbamoyl, $C_{1-6}$alkylS(O)$_a$ wherein a is 0–2, N-($C_{1-6}$alkyl)sulphamoylamino, N,N-($C_6$alkyl)$_2$sulphamoylamino, $C_{1-6}$alkylsulphonylamino, ($C_{1-6}$alkyl)sulphonyl-N-($C_{1-6}$alkyl)amino, N-($C_{1-6}$alkyl) sulphamoyl and N,N-($C_{1-6}$alkyl)$_2$sulphamoyl; wherein R⁵ and R⁶ may be optionally substituted on carbon by one or more R⁹; and wherein if said hetcrocyclyl contains an —NH— moiety that nitrogen may be independently optionally substituted by R¹⁰;

R⁷ and R⁹ are independently selected from halo, hydroxy, cyano, carbamoyl, ureido, trifluoromethyl, trifluoromethoxy, amino, nitro, carboxy, carbamoyl, mercapto, sulfamoyl, aminosulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{1-4}$alkoxycarbonylamino, $C_{2-4}$alkenyloxycarbonyl, $C_{1-4}$alkanoyl, $C_{1-4}$alkanoylamino, $C_{1-4}$alkanoyloxy, N-($C_{1-4}$alkyl)amino, N,N-($C_{1-4}$alkyl)$_2$ amino, N-($C_{1-4}$alkyl)carbarnoyl, N,N-($C_{1-4}$alkyl)$_2$ carbamoyl, $C_{1-4}$alkylS(O)$_a$ wherein a is 0–2, N-($C_{1-4}$alkyl)sulphamoylamino, N,N-($C_{1-4}$alkyl)$_2$sulpharnoylamino, ($C_{1-4}$ alkyl)sulphonylamino, ($C_{1-4}$alkyl)sulphonyl-N-($C_{1-4}$alkyl)amino, N-($C_{1-4}$alkyl)sulphamoyl, N,N-($C_{1-4}$alkyl)$_2$ sulphamoyl, heterocyclyl, heterocyclyloxy, heterocyclylamino, heterocyclyl-N-($C_{1-4}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-4}$alkyl)amino, carboocyclylsulphonyl, carbocyclylcarbonyl, carbocyclylcarbonylamino, and carbocycyloxycarbonyl; wherein R⁷ and R⁹ may be independently optionally substituted on carbon by one or more R¹¹;

R⁸ and R¹⁰ are independently selected from $C_{1-4}$alkyl, $C_{1-4}$alkanoyl, sulphamoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)$_2$carbamoyl, N-($C_{1-4}$alkyl)sulphamoyl, N,N-($C_{1-4}$alkyl)$_2$sulphamoyl, heterocyclyl, heterocyclylcarbonyl, heterocyclyloxycarbonyl, heterocyclylsulphonyl, carbocyclyl, carbocyclylcarbonyl, carbocycyloxycarbonyl and carbocyclylsulphonyl; wherein R⁸ and R¹⁰ may be independently optionally substituted on carbon by one or more R¹²;

R¹¹ and R¹² are independently selected from halo, hydroxy, cyano, carbamoyl, ureido, amino, nitro, carboxy, carbamoyl, mercapto, sulphamoyl, methyl, ethyl, vinyl, allyl, methoxy, ethoxy, vinyloxy, allyloxy, methoxycarbonyl, formyl, acetyl, formainido, acetylamino, acetoxy, methylamino, dimethylamino, N-methylcarbamoyl, N,N-dimethylcarbamoyl, methylthio, methylsulphinyl, mesyl, N-methylsulphamoyl, N.N-dimethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

x is 0–4; wherein the values of R¹ may be the same or different;

y is 0–3; wherein the values of R² may be the same or different;

z is 0–3; wherein the values of R⁴ may be the same or different; and with the providing that when R³ is a nitrogen linked heterocyclyl, A is a direct bond;

or a pharmaceutically acceptable salt, prodrug or solvate thereof

According to a particular feature of the invention there is provided a method of treating eating disorders in a warm-blooded animal, such as a human being, in need of such treatment which comprises administering to said animal a therapeutically effective amount of a compound of formula (IB') or a pharmaceutically acceptable salt, prodrug or solvate thereof.

According to a particular feature of the invention there is provided a method for promoting weight loss in a warm-blooded animal, such as a human being, in need of such treatment which comprises administering to said animal a therapeutically effective amount of a compound of formula (IB') or a pharmaceutically acceptable salt, prodrug or solvate thereof.

In particular further feature of the invention there is provided a method of treating disorders mediated by the neuropeptide Y5 receptor in a warm-blooded animal, such as a human being, in need of such treatment which comprises administering to said animal a therapeutically effective amount of a compound of formula (IB) which is 5,5-dioxo-2-[(2,2,2-trifluoro-1-hydroxy-1-methylethyl)carbonylamino]dibenzothiophene, 2-acetamidodibenzothiophene or 5,5-dioxo-2-acetamidodibenzothiophene or a pharmaceutically acceptable salt, prodrug or solvate thereof.

In particular further feature of the invention there is provided a method of treating eating disorders in a warm-blooded animal, such as a human being, in need of such treatment which comprises administering to said animal a therapeutically effective amount of a compound of formula (IB') which is 5,5-dioxo-2-[(2,2,2-trifluoro-1-hydroxy-1-methylethyl) carbonylamino]dibenzothiophene, 2-acetamidodibenzothiophene or 5,5-dioxo-2-acetamidodibenzothiophene or a pharmaceutically acceptable salt, prodrug or solvate thereof.

According to this further feature of the invention there is provided a method of treating eating disorders in a warm-blooded animal, such as a human being, in need of such treatment which comprises administering to said animal a therapeutically effective amount of a compound of formula (IB) or a pharmaceutically acceptable salt, prodrug or solvate thereof.

According to this further feature of the invention there is provided a method of treating eating disorders in a warm-blooded animal, such as a human being, in need of such treatment which comprises administering to said animal a therapeutically effective amount of a compound of formula (IB) which is 5,5-dioxo-2-[(2,2,2-trifluoro-1-hydroxy-1-methylethyl) carbonylamino]dibenzothiophene, 2-acetamidodibenzotliiophene or 5,5-dioxo-2-acetamidodibenzothiophene or a pharmaceutically acceptable salt, prodrug or solvate thereof.

According to an additional aspect of the invention there is provided the use of a compound of formula (IB) or a pharmaceutically acceptable salt, prodrug or solvate thereof in the manufacture of a medicament for the treatment of disorders mediated by the neuropeptide Y5 receptor in a warm-blooded animal, such as a human being.

According to an additional aspect of the invention there is provided the use of a compound of formula (IB') or a pharmaceutically acceptable salt, prodrug or solvate thereof in the manufacture of a medicament for the treatment of disorders mediated by the neuropeptide Y5 receptor in a warm-blooded animal, such as a human being According to an additional aspect of the invention there is provided the use of a compound of formula (IB) which is 5,5-dioxo-2-[(2,2,2-trifluoro-1-hydroxy-1-methylethyl) carbonylamino]dibenzothiophene, 2-acetamidodibenzothiophene or 5,5-dioxo-2-acetamidodibenzothiophene or a pharmaceutically acceptable salt, prodrug or solvate thereof in the manufacture of a medicament for the treatment of disorders mediated by the neuropeptide Y5 receptor in a warm-blooded animal, such as a human being.

According to an additional aspect of the invention there is provided the use of a compound of formula (IB') which is 5,5-dioxo-2-[(2,2,2-trifluoro-1-hydroxy-1-methylethyl) carbonylamino]dibenzothiophene, 2-acetamidodibenzothiophcnc or 5,5-dioxo-2-acetamidodibenzothiophene or a pharmaceutically acceptable salt, prodrug or solvate thereof in the manufacture of a medicament for the treatment of eating disorders in a warm-blooded animal, such as a human being.

According to an additional aspect of the invention there is provided the use of a compound of formula (IB) or a pharmaceutically acceptable salt, prodrug or solvate thereof in the manufacture of a medicament for the treatment of eating disorders in a warm-blooded animal, such as a human being.

According to an additional aspect of the invention there is provided the use of a compound of formula (IB') or a pharmaceutically acceptable salt, prodrug or solvate thereof in the manufacture of a medicament for the treatment of eating disorders in a warm-blooded animal, such as a human being.

According to an additional aspect of the invention there is provided the use of a compound of formula (IB) or a pharmaceutically acceptable salt, prodrug or solvate thereof in the manufacture of a medicament for promoting weight loss in a warm-blooded animal, such as a human being.

According to an additional aspect of the invention there is provided the use of a compound of formula (IB') or a pharmaceutically acceptable salt, prodrug or solvate thereof in the manufacture of a medicament for promoting weight loss in a warm-blooded animal, such as a human being.

According to an additional aspect of the invention there is provided the use of a compound of formula (IB) which is 5,5-dioxo-2-[(2,2,2-trifluoro-1-hydroxy-1-methylethyl) carbonylamino]dibenzothiophene, 2-acetamidodibenzothiophene or 5,5-dioxo-2-acetamidodibenzothiophene or a pharmaceutically acceptable salt, prodrug or solvate thereof in the manufacture of a medicament for the treatment of eating disorders in a warm-blooded animal, such as a human being.

According to an additional aspect of the invention there is provided the use of a compound of formula (IB') which is 5,5-dioxo-2-[(2,2,2-trifluoro-1-hydroxy-1-methylethyl) carbonylamino]dibenzothiophene, 2-acetamidodibcnzothiophene or 5,5-dioxo-2-acetamidodibenzothiophene or a pharmaceutically acceptable salt, prodrug or solvate thereof in the manufacture of a medicament for the treatment of eating disorders in a warm-blooded animal, such as a human being.

According to another aspect of the invention there is provided a pharmaceutical composition comprising a compound of formula (IB'), or a pharmaceutically acceptable salt, prodrug or solvate thereof, in association with a pharmaceutically acceptable diluent or carrier for the treatment of disorders mediated by the neuropeptide Y5 receptor in a warm-blooded animal, such as a human being.

According to another aspect of the invention there is provided a pharmaceutical composition comprising a compound of formula (IB'), or a pharmaceutically acceptable salt, prodrug or solvate thereof, in association with a pharmaceutically acceptable diluent or carrier for the treatment of eating disorders in a warm-blooded animal, such as a human being.

According to another aspect of the invention there is provided a pharmaceutical composition comprising a compound of formula (IB'), or a pharmaceutically acceptable salt, prodrug or solvate thereof, in association with a pharmaceutically acceptable diluent or carrier for promoting weight loss in a warm-blooded animal, such as a human being.

EXAMPLES

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;

(iii) chromatography means flash chromatography on silica gel (Merck Kciselgel ART 9385); thin layer chromatography (TLC) was carried out on silica gel plates; where a "Bond Elut" column is referred to, this means a column containing 20 g of silica, the silica being contained in a 70 ml disposable syringe and supported by a porous disc of 54Å pore size, obtained from International Sorbent Technology under the name "ISOLUTE"; "ISOLUTE" is a registered trade mark;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated; s, singlet; d, doublet; dd, double doublet; t, triplet; tt, triple triplet; q, quartet; tq, triple quartet; m, multiplet; br, broad;

(viii) chemical symbols have their usual meanings; SI units and symbols are used;
(ix) solvent ratios are given in volume:volume (v/v) terms; and
(x) mass spectra were run with an electron energy of 70 electron volts in the chemical ionization (CI) mode using a direct exposure probe; where indicated ionization was effected by electron impact (EI), fast atom bombardment (FAB) or electrospray (ES); values for m/z are given; generally, only ions which indicate the parent mass are reported and unless otherwise stated, the (MH)$^+$ is quoted;
(xi) unless stated otherwise compounds containing an asymmetrically substituted carbon and/or sulphur atom have not been resolved;
(xii) where a synthesis is described as being analogous to that described in a previous example the amounts used are the millimolar ratio equivalents to those used in the previous example;
(xvi) the following abbreviations have been used:
SM starting material;
EDAC 1-[3-(dimethylamino)propyl]-3-ethylcarbodiimide hydrochloride;
EtOAC ethyl acetate;
THE tetrahydrofuran;
DCM dichloromethane;
DMA dimethylacetamide;
ether diethyl ether;
DMF N,N-dimethylforthamide; and
DMSO dimethylsuilphoxide; and
xvii) where examples have chiral centres they are racemic mixtures unless otherwise indicated.

Example 1
2-(4-Nitrobenzoxycarbonylamino)dibenzothiophene

To a solution of p-nitrophenylchloroformate (5.57 g, 27.5 mmol) in EtOAc (60 ml) was added a solution of 2-aminodibenzthiophene (Bull. Soc. Chim. Fr. (1996), 133 (6), 597–610; 5.0 g, 25 mmol) in EtOAc (100 ml) over a period of 30 minutes with ice bath cooling. The mixture was stirred for 1 hour then poured onto water (500 ml) and extracted with EtOAc (4×250 ml). The combined organic layers were washed with water (2×100 ml) and brine (100 ml), dried and evaporated in vacuo to obtain the title compound (7.1 g). NMR: 10.66 (brs,1H), 8.5 (s,1H), 8.3 (d,2H), 8.2 (m,1H), 8.0 (m,2H), 7.6 (m, 1H), 7.5 (d, 2H), 7.5 (m,2H).

Example 2
2-t-Butylcarbonylamino)dibenzothiophene

2-Aminodibenzthiophene (Bull. Soc. Chim. Fr. (1996), 133 (6), 597–610; 2.0 g, 10 mmol) and triethylamine (1.11 g, 11 mmol) were dissolved in DCM (50 ml) and cooled in an ice bath. A solution of pivaloyl chloride (1.21 g, 10 mmol) in DCM (10 ml) was added slowly and the resultant solution was stirred at ambient temperature for 16 hours then evaporated in vacuo. The residue was triturated with methanol to leave the product as a colourless solid (1.85 g). NMR: 9.40 (s,1H), 8.59 (s,1H), 8.17 (m,1H), 7.98 (d,1H), 7.90 (d,1H), 7.73 (dd, 1 H), 7.46 (m,2H), 1.15 (s,9H); m/z 284.

Example 3
2-(1,2,4-Triazol-1-ylmethylcarbonylamino)dibenzothiophene

2-Aminodibenzthiophene (Bull. Soc. Chim. Fr. (1 996), 133 (6), 597–610; 500 mg, 2.5 mmol) was dissolved DMF (10 ml) and 2-(1,2,4-triazol-1-yl)acetic acid (318 mg, 2.5 mmol) was added in one portion followed by 1-hydroxybenztriazole hydrate (383 mg, 5.0 mmol) and EDAC (960 mg, 5.0 mmol). The resultant mixture was stirred for 16 hours at ambient temperature then poured on to water (100 ml). A fine white solid was collected which was washed extensively with water, methanol (25 ml) and ether (25 ml) to leave a colourless solid (650 mg). NMR: 10.62 (brs, 1H), 8.18 (m, 2H), 8.16 (m, 3H), 7.99 (m,3H), 7.62 (dd, 1H), 7.50 (m, 2H), 5.20 (s, 2H); m/z 309.

Examples 4–18

Following the procedure of Example 3 using 2-aminodibenzthiophene (Bull. Soc. Chim. Fr. (1996), 133 (6), 597–610) and the appropriate acid the following compounds were prepared.

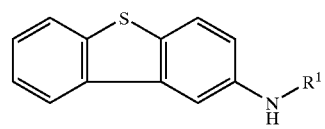

| Ex | R$^1$ | NMR | m/z |
|---|---|---|---|
| 4 | cyclopropyl-C(=O)- | 10.38 (brs, 1H), 8.6 (d, 1H), 8.15 (m, 1H), 8.0 (m, 1H), 7.9 (d, 1H), 7.6 (dd, 1H), 7.5 (m, 2H), 1.8 (m, 1H), 0.8 (m, 4H) | 268 |
| 5 | (2-oxopyrrolidin-1-yl)CH$_2$C(=O)- | 10.26 (brs, 1H), 8.59 (d, 1H), 8.17 (m, 1H), 8.00 (m, 1H), 7.94 (d, 1H), 7.61 (dd, 1H), 7.50 (m, 2H), 4.08 (s, 2H), 3.47 (t, 2H), 2.31 (t, 2H), 2.00 (m, 2H) | 325 |

-continued
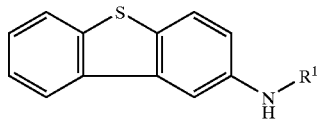
| Ex | R¹ | m/z |
|----|----|----|
| 6  |    | 284 |
| 7  |    | 360 |
| 8  |    | 327 |
| 9  |    | 312 |
| 10 |    | 348 |
| 11 |    | 347 |
| 12 |    | 323 |
| 13 |    | 335 |
| 14 |    | 320 (M − H)⁻ |
| 15 |    | 375 |

-continued

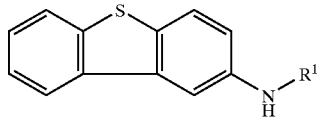

| | | |
|---|---|---|
| 16 | 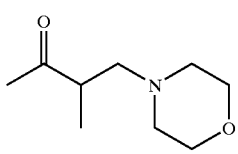 | 355 |
| 17 | 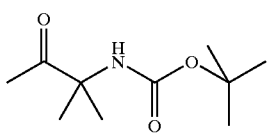 | 285 (des CO$_2$C(CH$_3$)$_3$) |
| 18 | 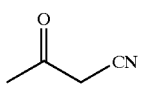 | 265 (M − H)⁻ |

Example 19

2-(N'-Pyrid-4-ylethyl-N'-methylureido)dibenzothiophene 2-(4-Nitrobenzoxycarbonylamino)dibenzothiophene (Example 1; 501 mg, 1.35 mmol) was suspended in EtOAc (10 ml) and 4-[2-(methylamino)ethyl]pyridine (408 mg, 3.0 mmol) added in one portion. The resulting mixture was stirred at ambient temperature for 16 hours then further EtOAc (50 ml) added. The solution was washed with 1 M sodium hydroxide (3×25 ml), water (2×25 ml) and brine (25 ml), dried and evaporated in vacuo. NMR 8.44 (m, 3H), 8.34 (d, 1H), 8.13 (m, 1H), 7.96 (m, 1H), 7.82 (d, 1H), 7.55 (dd, 1H), 7.47 (m, 2H), 7.28 (d, 2H), 3.61 (t, 2H), 2.96 (s, 3H), 2.86 (t, 2H); m/z 362.

Examples 20–22

Following the procedure of Example 19 using 2-(4-nitrobenzoxycarbonylamino) dibenzothiophene (Example 1) and the appropriate amine the following compounds were prepared.

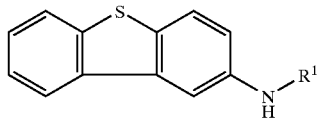

| Ex | R¹ | NMR | m/z |
|---|---|---|---|
| 20 | ![morpholine acetyl] | 8.72 (s, 1H), 8.40 (s, 1H), 8.14 (m, 1H), 7.96 (m, 1H), 7.84 (d, 1H), 7.58 (d, 1H), 7.46 (m, 2H), 3.63 (t, 4H), 3.45 (t, 4H) | 313 |
| 21 | ![N-ethyl-N-(pyridin-4-ylmethyl)acetyl] | 8.64 (s, 1H), 8.43 (d, 1H), 8.13 (d, 2H), 7.97 (m, 1H), 7.85 (d, 1H), 7.62 (dd, 1H), 7.47 (m, 2H), 7.28 (d, 2H), 4.63 (s, 2H), 3.45 (q, 2H), 1.12 (t, 3H) | 362 |
| 22 | ![4-hydroxymethylpiperidine acetyl] | 8.63 (s, 1H), 8.40 (d, 1H), 8.12 (m, 1H), 7.95 (m, 1H), 7.82 (d, 1H), 7.58 (dd, 1H), 7.46 (m, 2H), 4.44 (t, 1H), 4.17 (d, 2H), 3.28 (m, 2H), 2.80 (m, 2H), 1.68 (d, 2H), 1.58 (m, 1H), 1.10 (m, 2H) | 341 |

Example 23
5-oxo-2-(t-Butylcarbonylamino)dibenzothiophene m-Chloroperoxybenzoic acid (50% wt/wt, 770 mg, 2.0 mmol) was added to a solution of 2-(t-butylcarbonylamino)dibenzothiophene (Example 2; 566 mg, 2.0 mmol) in 1,2-dichloroethane and the resultant mixture warmed at 80% for 16 hours then cooled and DCM was added (50 ml). The mixture was washed with 2 M sodium hydroxide, water and brine, dried and evaporated in vacuo to a brown gum. This was purified by chromatography eluting with 0–2% methanol in DCM. The impure product thus obtained was purified by preparative HPLC (Dynamax C-18 60A column eluted with 40–95% acetonitrile in water plus 0.1% trifluoroacetic acid) to obtain the product (53.5 mg) NMR: 9.59 (s, 1H), 8.35 (d, 1H), 8.03 (d, 1H), 7.97 (d, 1H), 7.93 (d, 1H), 7.80 (dd, 1H), 7.70 (t, 1H), 7.56 (t, 1H), 1.16 (s, 9H); m/z 300.

Example 24
5,5-Dioxo-2-(4-nitrobenzoxycarbonylamino)dibenzothiophene; and

Example 25
5-Oxo-2-(4-nitrobenzoxycarbonylamino)dibenzothiophene 2-(4-Nitrobenzoxycarbonylamino)dibenzothiophene (Example 1; 364 mg, 1.0 mmol) was suspended in a mixture of glacial acetic acid (5.0 ml) and 30% hydrogen peroxide (565 mg, 5 mmol) and the mixture was warmed at 60° C. for 2 hours. The suspension of the title compound was filtered and air dried. TLC: (2:1; EtOAc:isohexane) Rf=0.30. 5-Oxo-2-(4-nitrobenzoxycarbonylamino)dibenzothiophene was also isolated as a by product in this reaction in a 1:5 ratio with the di-oxo compound. TLC: (2:1; EtOAc:isohexane) Rf=0.06.

Example 26
5.5-Dioxo-2-(isopropylcarbonylamino)dibenxzothiophene 5,5-Dioxo-2-aminodibenzothiophene (J Med Chem, (1994), 37 (13), 2085–9; 231 mg, 1.0 mmol) was suspended in a solution of DCM (10 ml) and triethylamine (111 mg, 1.1 mmol). iso-Butyrylchloride (106.5 mg, 1.0 mmol) was added dropwise and the resultant mixture was stirred for 16 hours at ambient temperature. The mixture was evaporated in vacuo and the residue was purified by chromatography (Bond Elut column) eluting with 0–2.5% methanol in DCM to give the product as a colourless solid (139 mg). NMR: 10.38 (brs, 1H), 8.37 (s, 1H), 7.85–8.00 (m, 3H), 7.80 (d, 1H), 7.74 (d, 1H), 7.63 (t, 1H), 2.66 (m, 1H), 1.13 (d, 6H); m/z 302.

Examples 27–28

Following the procedure of Example 26 using 5,5-dioxo-2-aminodibenzothiophene (J Med Chem, (1994), 37 (13), 2085–9) and the appropriate acid chloride the following compounds were prepared.

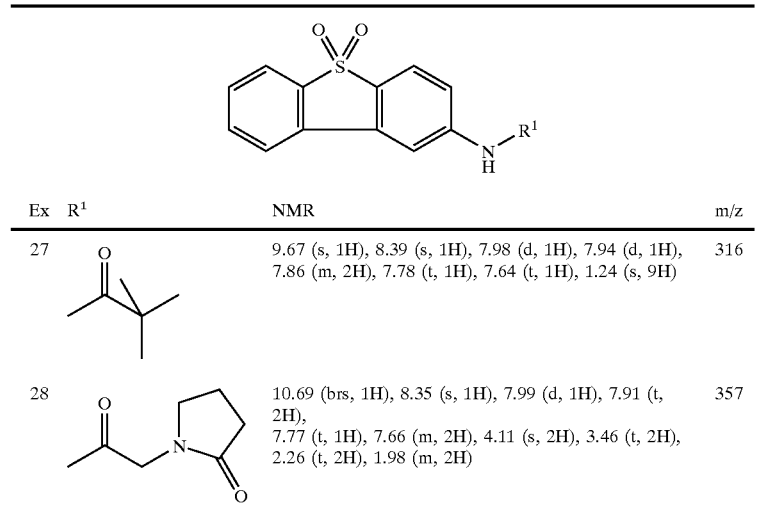

| Ex | R¹ | NMR | m/z |
|----|----|----|----|
| 27 | (pivaloyl) | 9.67 (s, 1H), 8.39 (s, 1H), 7.98 (d, 1H), 7.94 (d, 1H), 7.86 (m, 2H), 7.78 (t, 1H), 7.64 (t, 1H), 1.24 (s, 9H) | 316 |
| 28 | (2-oxopyrrolidin-1-ylmethylcarbonyl) | 10.69 (brs, 1H), 8.35 (s, 1H), 7.99 (d, 1H), 7.91 (t, 2H), 7.77 (t, 1H), 7.66 (m, 2H), 4.11 (s, 2H), 3.46 (t, 2H), 2.26 (t, 2H), 1.98 (m, 2H) | 357 |

Example 29
5,5-Dioxo-2-(pyrid-4-ylethylcarbonylamino)dibenzothiophene 5,5-Dioxo-2-aminodibenzothiophene (J Med Chem, (1994), 37 (13), 2085–9; 115 mg, 0.5 mmol) was dissolved in DMF (2.0 ml) and 3-(pyridin-4-yl)propionic acid (Method 1; 75 mg, 0.5 mmol) was added in one portion followed by EDAC (115 mg, 0.5 mmol) and the resultant mixture was stirred for 72 hours at ambient temperature: It was then poured onto water (50 ml) and extracted with DCM (2–50 ml), dried and evaporated in vacuo. The residue thus obtained was purified by chromatography (Bond Elut column) eluted with 0–5.0% methanol in DCM to give the product as a colourless solid (31.8 mg). NMR 10.52 (brs, 1H), 8.46 (d, 2H), 8.32 (d, 1H), 7.97 (d, 1H), 7.94 (d, 1H), 7.88 (d, 1H), 7.76 (d, 1H), 7.70 (t, 1H), 7.64 (t, 1H), 7.26 (d, 2H), 2.93 (t, 2H), 2.75 (t, 2H); m/z 365.

Example 30

Following the procedure of Example 29 using 5,5-dioxo-2-aminodibenzothiophene (J Med Chem, (1994), 37 (13), 2085–9) and the appropriate acid the following compound was prepared.

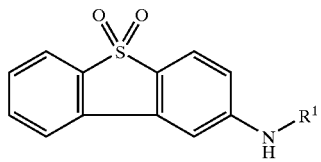

| Ex | R¹ | NMR DMSO-d₆ + d₄-acetic acid, 100° C. | m/z |
|---|---|---|---|
| 30 | (2-methyl-4-morpholinyl-butan-2-one group) | 8.26 (s, 1H), 7.88 (d, 1H), 7.80 (m, 1H), 7.72 (m, 3H), 7.61 (t, 1H), 3.78 (t, 4H), 3.37 (dd, 1H), 3.03 (m, 5H), 1.95 (dd, 1H), 1.26 (d, 3H) | 387 |

Example 31

5,5-Dioxo-2-(1,2,4-triazol-1-ylmethylcarbonylamino)dibenzothiophene 2-(1,2,4-Triazol-1-ylmethylcarbonylamino)dibenzothiophene (Example 3; 110 mg 0.34 mmol) was suspended in glacial acetic acid (3.0 ml) and 30% hydrogen peroxide was added (0.75 ml). The mixture was warmed to gentle reflux for 30 minutes to give a pale straw-coloured homogeneous solution which was poured onto water (50 ml) and extracted with DCM (2×25 ml), dried and evaporated in vacuo to leave a pale yellow solid (73 mg). NMR: 10.94 (brs, 1H), 8.55 (s, 1H), 8.32 (d, 1H), 7.98 (m, 2H), 7.95 (s, 1H), 7.93 (s, 1H), 7.76 (t, 1H), 7.70 (dd, 1H), 7.63 (t, 1H), 5.21 (s, 2H); m/z 341.

Examples 32–37

Following the procedure of Example 31 using the appropriate dibenzothiophenes the following compounds were prepared.

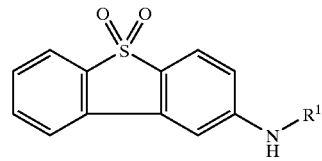

| Ex | R¹ | NMR | m/z | SM |
|---|---|---|---|---|
| 32 | cyclopropyl ketone | 10.74 (brs, 1H), 8.35 (d, m), 7.9 (m, 3H), 7.8 (t, 1H), 7.7 (dd, 1H), 7.6 (t, 1H), 1.85 (m, 1H), 0.9 (m, 4H) | 300 | Ex 4 |
| 33 | methoxy ketone | 10.49 (brs, 1H), 8.35 (d, 1H), 7.95 (d, 1H), 7.9 (d, 1H), 7.85 (d, 1H), 7.8 (t, 1H), 7.7 (dd, 1H), 7.65 (t, 1H), 3.65 (t, 2H), 3.3 (s, 3H), 2.6 (t, 2H) | 318 | Ex 6 |
| 34 | sulfolanyl ketone | 10.54 (brs, 1H), 8.35 (s, 1H), 7.9 (m, 3H), 7.8 (t, 1H), 7.7 (m, 2H), 3.4–3.0 (m, 3H), 2.9–2.7 (m, 2H), 2.65 (m, 2H), 2.3 (m, 1H), 1.9 (m, 1H) | 392 | Ex 7 |
| 35 | oxazolidinone ketone | 10.64 (brs, 1H), 8.35 (d, 1H), 8.0 (d, 1H), 7.95 (d, 1H), 7.9 (d, 1H), 7.8 (t, 1H), 7.7 (dd, 1H), 7.65 (t, 1H), 4.3 (t, 2H), 4.1 (s, 2H), 3.7 (t, 2H) | 359 | Ex 8 |
| 36 | tetrahydropyranyl ketone | 10.43 (brs, 1H), 8.4 (d, 1H), 8.0 (d, 1H), 7.95 (d, 1H), 7.9 (d, 1H), 7.8 (t, 1H), 7.7 (dd, 1H), 7.65 (t, 1H), 3.9 (m, 2H), 3.35 (m, 2H), 2.7 (m, 1H), 1.7 (m, 4H) | 344 | Ex 9 |

-continued

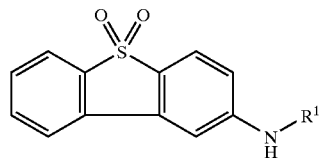

| Ex | R¹ | NMR | m/z | SM |
|---|---|---|---|---|
| 37 | (2-oxo-1-methyl-ethyl phenyl ether group) | 10.64 (brs, 1H), 8.4 (s, 1H), 7.9 (m, 3H), 7.8 (m, 2H), 7.65 (t, 1H), 7.3 (m, 2H), 6.95 (m, 3H), 4.9 (q, 1H), 1.6 (d, 3H) | 380 | Ex 10 |

Example 38

5,5-Dioxo-2-[(2-pyrid-4-yl-1-methylethyl)carbonylamino]dibenzothiophene

2-[(2-Pyrid-4-yl-1-methylethyl)carbonylamino]dibenzothiophene (Example 11; 0.39 g, 1.13 mmol) was dissolved in glacial acetic acid (10 ml) and concentrated sulphuric acid (0.5 ml) at 60° C. 30% aqueous hydrogen peroxide (1.3 ml) was added in one portion and the solution was stirred at 60° C. for two hours. The mixture was allowed to cool and then poured into water (50 ml). The mixture was made basic by the addition of solid NaHCO₃ and extracted with DCM (2×50 ml). The combined organic layers were washed with brine (50 ml), dried and evaporated in vacuo to leave a pale yellow solid. NMR: 8.45 (d, 2H), 8.3 (d, 1H), 8.0 (d, 1H), 7.95 (d, 1H), 7.9 (d, 1H), 7.8 (t, 1H), 7.7 (dd, 1H), 7.65 (t, 1H), 7.25 (d, 2H), 3.0 (m, 2H), 2.7 (m, 1H), 1.15 (d, 3H); m/z 379.

Examples 39–43

Following the procedure of Example 38 using the appropriate dibenzothiophenes the following compounds were prepared.

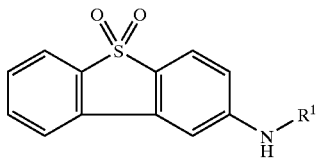

| Ex | R¹ | NMR | m/z | SM |
|---|---|---|---|---|
| 39 | (2-oxo-4-imidazol-1-yl-butyl) | 8.4 (d, 1H), 8.0 (d, 1H), 7.95 (d, 1H), 7.9 (d, 1H), 7.8 (m, 2H), 7.65 (m, 2H), 7.2 (s, 1H), 6.8 (s, 1H), 4.3 (t, 2H), 2.9 (t, 2H) | 354 | Ex 14 |
| 40 | (2-oxo-4-(1,2,4-triazol-1-yl)butyl) | 8.5 (s, 1H), 8.45 (d, 1H), 8.0 (d, 1H), 7.9 (m, 2H), 7.85 (d, 1H), 7.8 (m, 2H), 7.65 (t, 1H), 4.5 (t, 2H), 3.0 (t, 2H) | 355 | Ex 12 |
| 41 | (2-oxo-pyridin-3-yloxymethyl) | 11.24 (brs, 1H), 8.4 (d, 1H), 8.1 (s, 1H), 8.05 (d, 1H), 8.0 (d, 1H), 7.95 (m, 2H), 7.8–7.6 (m, 5H), 5.5 (s, 2H) | 367 | Ex 13 |
| 42 | (2-oxo-3-cyanopropyl) | 10.83 (brs, 1H), 8.3 (s, 1H), 8.0 (d, 1H), 7.95 (m, 2H), 7.8 (t, 1H), 7.7 (m, 2H), 4.0 (s, 2H) | 297 (M − H)⁻ | Ex 19 |

| Ex | R¹ | m/z | SM |
|---|---|---|---|
| 43 | 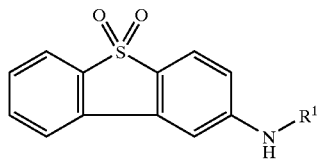 | 316 | Ex 17 |

Example 44
5,5-Dioxo-2-(N'-pyrid-4-ylethyl-N'-methylureido) dibenzothiophene; and

Example 45
5-Oxo-2-(N'-pyrid-4-ylethyl-N'-methylureido) dibenzothiophene 5,5-Dioxo-2-(4-nitrobenzoxycarbonylamino) dibenzothiophene contaminated with 5-oxo-2-(4-nitrobenzoxycarbonylamino)dibenzothiophene (Examples 24 and 25; 396 mg, 1.0 mmol) was suspended in EtOAc (10 ml) and 4-[2-(methylamino)ethyl]pyridine (272 mg, 2.0 mmol) was added in one portion. The resulting mixture was stirred at ambient temperature for 16 hours then further EtOAc (100 ml) was added and the solution was washed with 1 M sodium hydroxide (2×25 ml), water (2×25 ml) and brine (25 ml), dried and evaporated in vacuo. The resulting mixture was separated by preparative HPLC (Dynamax C-18 60A column eluted with 20–90% acetonitrile in water plus 0.1% trifluoroacetic acid). Two products were obtained:

5-Oxo-2-(N'-pyrid-4-ylethyl-N'-methylureido) dibenzothiophene (16.5 mg): NMR: 8.71 (s, 1H), 8.67 (d, 2H), 8.17 (s, 1H), 8.02 (d, 1H), 7.85 (m, 2H), 7.72 (d, 2H), 7.67 (t, 1H), 7.56 (m, 2H), 3.69 (t, 2H), 3.05 (t, 2H), 3.01 (s, 3H); m/z 378.

5,5-Dioxo-2-(N'-pyrid-4-ylethyl-N'-methylureido) dibenzothiophene (82.0 mg): NMR: 8.84 (s, 1H), 8.66 (d, 2H), 8.10 (s, 1H), 7.90 (d, 2H), 7.75 (m, 4H), 7.62 (t, 2H), 3.69 (t, 2H), 3.04 (t, 2H), 3.01 (s, 3H); m/z 394.

Examples 46–49

Following the procedure of Example 44 using 5,5-dioxo-2-(4-nitrobenzoxycarbonyl-amino)dibenzothiophene (Example 24) and the appropriate amine the following compounds were prepared (NB the corresponding sulphoxides were not isolated).

| Ex | R¹ | NMR | m/z |
|---|---|---|---|
| 46 | | 9.81 (brs, 1H), 8.13 (d, 1H), 7.96 (d, 1H), 7.89 (d, 1H), 7.76 (m, 2H), 7.63 (t, 1H), 7.56 (dd, 1H), 3.42 (t, 2H), 2.96 (s, 3H), 2.46 (1, 2H), (2.24, s, 6H) | 360 |
| 47 | | 8.80 (s, 1H), 8.20 (s, 1H), 7.92 (m, 2H), 7.77 (m, 2H), 7.64 (m, 2H), 4.02 (m, 1H), 2.05 (s, 3H), 2.02 (d, 2H), 2.15 (s, 3H), 1.95 (1, 2H), 2.14, (m, 2H), 1.51 (d, 2H) | 386 |
| 48 | | 9.1 (brs, 1H), 8.1 (s, 1H), 7.9 (t, 2H), 7.8 (d, 1H), 7.75 (t, 1H), 7.6 (m, 2H), 3.6 (m, 4H), 3.5 (m, 4H) | 345 |

-continued

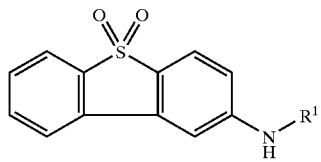

| Ex | R¹ | NMR | m/z |
|---|---|---|---|
| 49 | (N-methylpiperazine with acetyl group) | 9.1 (s, 1H), 8.2 (s, 1H), 7.9 (t, 2H), 7.8 (m, 2H), 7.6 (m, 2H), 3.5 (m, 4H), 2.3 (m, 4H), 2.2 (s, 3H) | 358 |

Example 50
5,5-Dioxo-2-(4,4,4-trifluoro-2-methylbutrylcarbonylamino)dibenzothiophene EDAC (0.307 g, 1.6 mmol) was added to a solution of 2-aminodibenzothiophene 0.299 g, 1.5 mmol), 1-hydroxybenzotriazole (0.216 g, 1.6 mmol) and 4,4,4-trifluoro-2-methylbutanoic acid (0.250 g, 1.6 mmol) in DMF (10 ml). The solution was stirred at room temperature overnight. The solvent was removed in vacuo and the residue was shaken in water. The crude product was collected by filtration and dried in air. The crude amide was dissolved in glacial acetic acid (10 ml) at 60° C. and hydrogen peroxide (30 wt. % solution in water, 2 ml) was added. The mixture was stirred at 60° C. for 2 hours and left to cool to room temperature overnight. The mixture was filtered and the residue was washed with water (10 ml), methanol (5 ml) and finally with ether (3×5 ml) to leave a pale yellow solid (0.147 g). NMR: 10.63 (s, 1H), 8.3 (d, 1H), 8.0 (d, 1H), 7.9 (m, 2H), 7.75 (m, 2H ), 7.7 (t, 1H), 2.9 (m, 1H), 2.7 (m, 1H), 2.4 (m, 1H), 1.3 (d, 3H); m/z 370.

Examples 51–65

Following the procedure of Example 50 using 2-aminodibenzothiophene and the appropriate acid the following compounds were prepared (NB the corresponding sulphides were not isolated).

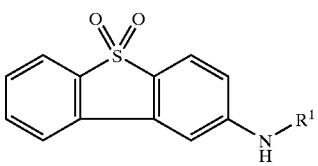

| Ex | R¹ | NMR | MS |
|---|---|---|---|
| 51 | (2-oxocyclopentyl acetyl) | 12.1 (s, 1H), 8.2 (s, 1H), 8.1 (m, 2H), 8.0 (d, 1H), 7.8 (t, 1H), 7.7 (m, 2H), 2.8 (m, 2H), 2.2 (m, 2H), 1.7 (m, 4H), 1.5 (m, 1H) | 354 (M − H)⁻ |
| 52 | (5,5-dimethyl-2-oxotetrahydrofuran-3-yl carbonyl) | 10.68 (s, 1H), 8.4 (s, 1H), 8.0 (d, 1H), 7.9 (m, 2H), 7.7 (m, 3H), 3.3 (m, 1H), 3.0 (dd, 1H), 2.8 (dd, 1H), 1.5 (s, 3H), 1.3 (s, 3H) | 370 (M − H)⁻ |
| 53 | (tetrahydrofuran-3-yl carbonyl) | 10.55 (s, 1H), 8.4 (s, 1H), 7.9 (m, 3H), 7.7 (m, 3H), 4.0 (t, 1H), 3.8 (m, 3H), 3.2 (m, 1H), 2.1 (m, 2H) | 328 (M − H)⁻ |

-continued

| Ex | R¹ | NMR | MS |
|---|---|---|---|
| 54 | (4-acetyl-2,2-dimethyltetrahydropyran) | 10.42 (s, 1H), 8.35 (s, 1H), 7.9 (m, 3H), 7.8 (t, 1H), 7.7 (dd, 1H), 7.65 (t, 1H), 3.6 (m, 2H), 2.8 (m, 1H), 1.7–1.4 (m, 4H), 1.2 (s, 3H), 1.15 (s, 3H) | 372 |
| 55[1] | (N-(2-oxopropyl)succinimide) | 10.81 (s, 1H), 8.3 (s, 1H), 8.0 (d, 1H), 7.9 (m, 2H), 7.8 (t, 1H), 7.65 (m, 2H), 4.3 (s, 2H), 2.75 (s, 4H) | 371 |
| 56 | (1-benzyl-4-acetylpyrrolidin-2-one) | 10.59 (s, 1H), 8.3 (s, 1H), 7.9 (m, 3H), 7.8 (t, 1H), 7.7 (m, 2H), 7.3 (m, 2H), 7.2 (m, 3H), 4.4 (s, 2H), 3.5 (m, 1H), 3.2 (m, 2H), 2.65 (m, 2H) | 433 |
| 57[2] | (3-acetyl-5-phenyldihydrofuran-2(3H)-one) | 10.7 (s, 1H), 8.35 (s, 1H), 8.0 (d, 1H), 7.9 (m, 2H), 7.8 (t, 1H), 7.7 (m, 2H), 7.4 (m, 5H), 5.7 (d, 1H), 3.1 (dd, 1H), 2.9 (dd, 1H) | 418 (M − H)⁻ |
| 58 | (N-(3-oxobutyl)succinimide) | 10.54 (s, 1H), 8.3 (s, 1H), 7.9 (m, 3H), 7.8 (t, 1H), 7.7 (m, 2H), 3.7 (t, 2H), 2.6 (m, 6H) | 385 |
| 59[3] | (acetyl-hydroxynorbornyl) | 10.15 (s, 1H), 8.4 (d, 1H), 7.9 (m, 2H), 7.85 (d, 1H), 7.75 (t, 1H), 7.65 (m, 2H), 4.8 (d, 1H), 4.0 (m, 1H), 2.55 (d, 1H), 2.4 (bs, 1H), 2.0 (m, 2H), 1.4 (m, 2H), 1.1 (m, 3H) | 370 |
| 60[4] | (3-benzyl-1-(2-oxopropyl)pyrrolidin-2-one) | 10.64 (s, 1H), 8.3 (d, 1H), 8.0 (d, 1H), 7.9 (m, 2H), 7.8 (t, 1H), 7.7 (m, 2H), 7.25 (m, 5H), 4.2 (d, 1H), 4.1 (d, 1H), 3.3 (m, 2H), 3.1 (dd, 1H), 2.7 (m, 1H), 2.6 (m, 1H), 2.0 (m, 1H), 1.7 (m, 1H) | 447 |

-continued

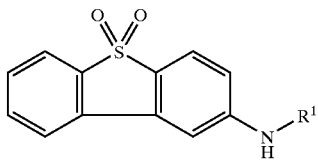

| Ex | R¹ | NMR | MS |
|---|---|---|---|
| 61[5] | (2-oxopropoxy-pyridazin-OH group) | NMR (400 MHz) 12.2 (s, 1H), 10.7 (s, 1H), 8.35 (d, 1H), 8.05 (d, 1H), 7.95 (m, 2H), 7.8 (td, 1H), 7.75 (dd, 1H), 7.7 (td, 1H), 7.35 (d, 1H), 6.95 (d, 1H), 4.9 (s, 2H) | 384 |

[1] Acid: Al-Azhar J. Pharm. Sci., 1998, 21, 133–141
[2] Acid: Arch. Immunol. Ther. Exp., 1968, 16 (1), 155–172
[4] Acid: J. Am. Chem. Soc., 1974, 96 (20), 6492–6498
[4] Acid: Method 4
[5] Acid: Am. Khim. Zh., 1971, 24 (4), 350–353

| Ex | R¹ | MS | Acid Preparation Reference |
|---|---|---|---|
| 62 | (1-(2-oxopropyl)pyridin-2(1H)-one) | 367 | Rev. Roum. Chim., 1988, 33 (7), 729–739 |
| 63 | (2-methyl-3-oxo-1-(1H-1,2,4-triazol-1-yl)propyl) | 369 | Method 6 |
| 64 | (4-acetyl-1-methylpyrrolidin-2-one) | 357 | J. Org. Chem., 1980, 45(5), 810–814 |
| 65 | (3-acetyl-1-methyl-2-phenylpyrrolidin-5-one) | 433 | J. Org. Chem., 1969, 34(10), 3187–3189 |

Example 66

5,5-Dioxo-2-(3-methyl-3-pyridin-4-ylpropionamido)dibenzothiophene

EDAC (0.500 g, 2.6 mmol) was added to a solution of 2-aminodibenzothiophene (0.470 g, 2.4 mmol), 1-hydroxybenzotriazole (0.351 g, 2.6 mmol) and 3-methyl-3-pyridin-4-ylpropanoic acid (Method 7; 0.429 g, 2.6 mmol) in DMF (10 ml). The solution was then stirred at room temperature overnight. The solvent was removed in vacuo and the residue was then shaken in water (50 ml) and DCM (50 ml). The organic layer was separated, washed with brine (50 ml), dried and then evaporated in vacuo to leave a light brown solid. The crude amide was dissolved in a mixture of glacial acetic acid (15 ml) and concentrated sulphuric acid (0.5 ml) at 60° C. and hydrogen peroxide (30 wt. % solution in water, 3 ml) was added. The mixture was stirred at 60° C. for 2 hours and left to cool to room temperature overnight. The mixture was poured into water (50 ml) and made basic by the addition of potassium carbonate. The mixture was extracted into DCM (50 ml), the organic layer was separated and washed with brine (50 ml), dried and evaporated in vacuo to leave a light brown solid. The crude product was triturated with methanol (10 ml) to leave a pale yellow solid (0.496 g). NMR: 10.47 (s, 1H), 8.3 (d, 1H), 7.9 (m, 3H), 7.75 (t, 1H), 7.65 (m, 2H), 3.3 (m, 1H), 2.7 (m, 2H), 1.3 (d, 3H); m/z 379.

Example 67
1-Cyano-5,5-dioxo-2-pivaloylaminodibenzothiophene

A mixture of 1-cyano-2-pivaloylaminodibenzothiophene (Example 68; 0.034 g, 0.11 mmol) glacial acetic acid (2 ml) and 30% hydrogen peroxide (0.2 ml) was heated at 80° C. for 4 hours. The mixture was cooled and poured into water. The precipitate was filtered and washed extensively with water to give the title compound. NMR 9.95 (s, 1H), 8.57 (d, 1H), 8.32 (d, 1H), 8.11 (d, 1H), 7.95 (t, 1H), 7.82 (t, 1H), 7.75 (d, 1H), 1.28 (s, 9H); m/z 341.

Example 68
1-Cyano-2-pivaloylaminodibenzothiophene

A mixture of 2-amino-1-cyanodibenzothiophene (J. Heterocyclyl. Chem., 1977, 14(7), 1209–1214; 0.043 g, 0.19 mmol), triethylamine (0.04 g, 0.4 mmol) and pivaloyl chloride (0.05 g, 0.4 mmol) in DCM (2 ml) was stirred at ambient temperature for 24 hours. The resultant mixture was extracted with water and the organic phase reduced to a residue which was triturated with ether/iso-hexane to give the title compound. NMR: 9.78 (s, 1H), 8.81 (m, 1H), 8.38 (d, 1H), 8.16 (m, 1H), 7.58 (m, 2H), 7.48 (d, 1H), 1.18 (s, 9H); m/z 307 (M–H)⁻.

Example 69
3-Methyl-5,5-dioxo-2-pivaloylaminodibenzothiophene

3-Bromo-5,5-dioxo-2-pivaloylaminodibenzothiophene (Example 70; 0.1 g, 0.254 mmol) was suspended in dry THF (2 ml) under argon, cooled to −70° C. and 1.7 M tert-butyllithium in pentane (0.49 ml, 0.838 mmol) was added dropwise over 5 minutes. The mixture was allowed to warm to −30° C. and the suspension slowly dissolved as the solution darkened. The mixture was then re-cooled to −70° C. and iodomethane (0.17 ml, 0.279 mmol) added and stirred for 30 minutes. Saturated ammonium acetate (5 ml) and DCM (25 ml) were added and the organic phase washed with water and dried. The mixture was evaporated in vacuo and the residue purified by preparative HPLC (Dynamax C-18 60A column eluted with 30–90% acetonitrile in water plus 0.1% trifluoroacetic acid) to give the product as a colourless solid. NMR: 9.16 (s, 1H), 8.13 (d, 1H), 7.99 (s, 1H), 7.92 (d, 1H), 7.86 (s, 1H), 7.76 (t, 1H), 7.61 (t, 1H), 2.28 (s, 3H), 1.26 (s, 9H); m/z 330.

Example 70
3-Bromo-5,5-dioxo-2-pivaloylaminodibenzothiophene

2-Amino-3-bromo-5,5-dioxidodibenzothiophene (DE 2638081; 0.309 g, 1.0 mmol) was suspended in a solution of DCM (5 ml) and triethylamine (0.111 g, 1.1 mmol). Pivaloyl chloride (0.132 g, 1.1 mmol) was added dropwise and the resultant mixture stirred for 5 days at ambient temperature. The mixture was reduced to dryness and the residue was triturated with methanol. NMR: 9.25 (s, 1H), 8.42 (s, 1H), 8.31 (s, 1H), 8.11 (d, 1H), 7.98 (d, 1H), 7.80 (t, 1H), 7.68 (t, 1H), 1.28 (s, 9H); m/z 394/396.

Example 71
1-Methyl-5,5-dioxo-2-(tetrahydrofur-3-ylcarbonylamino)dibenzothiophene 1-Methyl-2-(tetrahydrofur-3-ylcarbonylamino)dibenzothiophene (Example 72; 436 mg, 1.4 mmol) was stirred in glacial acetic acid (10 ml) and hydrogen peroxide (30% w/v, 2 ml) at 120° C. for 30 mins. The reaction mixture was cooled and the precipitate was filtered and washed with water to leave the product as a yellow crystalline solid. NMR: 9.96 (brs, 1H), 8.23 (d, 1H), 8.00 (d, 1H), 7.80 (m, 2H), 7.64 (m, 2H), 3.96 (m, 1H), 3.76 (m, 3H), 3.27 (m, 1H), 2.55 (s, 3H), 2.15 (q, 2H); m/z 344.

Example 72
1-Methyl-2-(tetrahydrofur-3-ylcarbonylamino)dibenzothiophene

2-Amino-1-methyldibenzothiophene (Method 10; 0.337 g, 1.58 mmol), 4-(dimethylamino)pyridine (0.213 g, 1.74 mmol), EDAC (0.334 g, 1.74 mmol) and tetrahydro-3-furoic acid (0.167 ml, 1.74 mmol) were stirred in DCM (20 ml) at reflux under an argon atmosphere for 64 h. The product was purified by flash chromatography eluting with DCM-5% methanol/DCM. Evaporation of the appropriate fractions gave the product as a white solid. NMR: 9.77 (brs, 1H), 8.44 (m, 1H), 8.04 (m, 1H), 7.82 (d, 1H), 7.52 (m, 2H), 7.36 (d, 1H), 4.00 (m, 1H), 3.76 (m, 3H), 3.27 (m, 1H), 2.68 (s, 3H), 2.15 (q, 2H); m/z 313.

Example 73
5,5-Dioxo-2-(6-methylpyridazin-3-ylamino)dibenzothiophene

Hydrogen peroxide (100 vols, 1 ml) was added to 2-(6-methylpyridazin-3-ylamino)dibenzothiophene (Example 74; 300 mgs, 1.03 mmol) in acetic acid (3 ml) and conc. sulphuric acid (0.1 ml) and the mixture was heated to 60° C. for 40 minutes. On cooling to room temperature the mixture was diluted with DCM:MeOH (1:19) washed with aqueous potassium carbonate, dried over sodium sulphate and concentrated. Chromatography (eluent gradient of DCM to DCM:MeOH(1:1)) gave the product as an off white solid (0.131 g). NMR: 9.87 (brs, 1H), 8.48 (brs, 1H), 8.00–7.70 (m, 5H), 7.65 (t, 1H), 7.45 (d, 1H), 7.20 (d, 1H), 2.52 (s, 3H); m/z 324.28.

Example 73
2-(6-Methylpyridazin-3-ylamino)dibenzothiophene

A mixture of 2-aminodibenzothiophene (0.90 g, 4.52 mM), 3-chloro-6-methyl-pyridazine (0.58 g, 4.52 mM), sodium t-butoxide (0.61 g, 6.33 mM), tris(dibenzylideneacetone)dipalladium(0) (0.083 g, 0.09 mM) and S-2,2'-bis(diphenylphosphino)-1,1'-binapthyl (0.113 g, 0.18 mM) in toluene (23 ml) was heated to 80° C. for 18 hours under an inert atmosphere. On cooling to room temperature the mixture was diluted with DCM, washed with aqueous potassium carbonate, dried over sodium sulphate and concentrated. Chromatography (eluent gradient of DCM to EtOAc then MeOH:EtOAc (1:9)) gave the product as an off white solid (0.456 g). NMR: 9.38 (brs, 1H), 8.81 (brs, 1H), 8.18 (m, 1H), 8.01 (m, 1H), 7.94 (d, 1H), 7.75 (dd, 1H), 7.50 (m, 1H), 7.36 (d, 1H), 7.14 (d, 1H), 2.50 (s, 3H); m/z 292.29.

Example 74
5,5-Dioxo-2-(N'-pyrid-4-ylmethyl-N'-ethylureido)dibenzothiophene 5,5-Dioxo-2-(4-nitrobenzoxycarbonylamino)dibenzothiophene (Example 24; 0.396 g, 1 mmol) was dissolved in EtOAc (10 ml) and treated with 4-(ethylaminomethyl)pyridine (0.150 g, 1.1 mmol), triethylamine (0.202 g, 2 mmol) and 4-(dimethylamino)pyridine (0.006 mg, 0.05 mmol). The reaction was stirred for 18 hours and the suspended solids collected, washed with 1 M aq. NaOH solution, water and then ether to leave the product as a colourless solid. NMR: 9.00 (s, 1H), 8.54 (m, 2H), 8.27 (s, 1H), 7.93 (m, 2H), 7.81 (m, 1H), 7.75 (m, 2H), 7.65 (m, 1H), 7.28 (m, 2H), 4.63 (s, 2H), 3.43 (q, 2H), 1.12 (t, 3H); m/z 394.42

Examples 75–192

Following the procedure of Example 74 using 5,5-Dioxo-2-(4-nitrobenzoxy-carbonylamino)dibenzothiophene (Example 24) and the appropriate amine the following compounds were prepared.

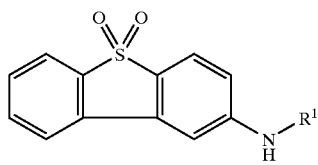

| Ex | R¹ | N. M. R. | MS |
|---|---|---|---|
| 75 | (1-acetylpiperidin-4-yl)methanol group | 9.04 (s, 1H), 8.21 (d, 1H), 7.93 (t, 2H), 7.79 (d, 1H), 7.75 (d, 1H), 7.64 (m, 2H), 4.15 (d, 2H), 3.26 (m, 2H), 2.82 (t, 2H), 1.70 (d, 2H), 1.60 (m, 1H), 1.08 (m, 2H) | 373 |
| 76 | N-methyl-N-(pyridin-3-ylmethyl)acetamide group | 9.03 (s, 1H), 8.54 (d, 1H), 8.48 (dd, 1H), 8.25 (s, 1H), 7.96 (d, 1H), 7.92 (d, 1H), 7.83 (d, 1H), 7.72 (m, 3H), 7.62 (t, 1H), 7.37 (dd, 1H), 4.61 (s, 2H), 3.02 (s, 3H) | 380 |
| 77 | N-(2-(pyridin-4-yl)ethyl)acetamide group | 9.12 (s, 1H), 8.48 (d, 2H), 8.15 (s, 1H), 7.97 (d, 1H), 7.90 (d, 1H), 7.7-7.9 (m, 2H), 7.66 (m, 1H), 7.52 (m, 1H), 7.28 (d, 2H), 6.48 (t, 1H), 3.44 (m, 2H), 2.81 (t, 2H) | 380 |
| 78 | N-(3-(1H-imidazol-1-yl)propyl)acetamide group | 9.13 (s, 1H), 8.16 (s, 1H), 7.99 (d, 1H), 7.90 (d, 1H), 7.77 (m, 2H), 7.53 (m, 2H), 7.53 (d, 1H), 7.19 (s, 1H), 6.90 (s, 1H), 6.52 (t, 1H), 4.00 (t, 2H), 3.10 (m, 2H), 1.89 (t, 2H) | 383 |
| 79 | 1-acetyl-2-(pyrrolidin-1-ylmethyl)pyrrolidine group | 8.10 (s, 1H), 7.90 (m, 3H), 7.81 (m, 1H), 7.78 (m, 1H), 7.74 (m, 1H), 7.46 (d, 1H), 4.0 (m, 1H), 3.57 (m, 1H), 3.29 (m, 1H), 2.75 (m, 3H), 2.60 (m, 2H), 2.50 (m, 1H), 2.02 (m, 1H), 1.65 (m, 7H) | 412 |
| 80 | 1-acetylpiperidine-3-carboxamide group | 9.10 (s, 1H), 8.20 (s, 1H), 7.93 (m, 2H), 7.80 (m, 2H), 7.64 (m, 2H), 7.33 (s, 1H), 6.88 (s, 1H), 4.10 (m, 1H), 4.05 (m, 1H), 2.93 (m, 1H), 2.84 (m, 1H), 2.30 (m, 1H), 1.92 (m, 1H), 1.68 (m, 2H), 1.52 (m, 1H), 1.42 (m, 1H) | 386 |
| 81 | trans N-(4-hydroxycyclohexyl)acetamide group | 8.93 (s, 1H), 8.15 (s, 1H), 7.98 (d, 1H), 7.90 (d, 1H), 7.75 (m, 1H), 7.64 (m, 1H), 6.31 (d, 1H), 4.50 (d, 1H), 3.42 (m, 1H), 1.83 (m, 4H), 1.23 (m, 4H) | 373 |
| 82 | 1-acetyl-4-(2-hydroxyethyl)piperidine group | 9.0 (s, 1H), 8.2 (d, 1H), 7.9 (t, 2H), 7.8 (m, 2H), 7.6 (m, 2H), 4.3 (t, 1H), 4.1 (m, 1H), 3.45 (q, 2H), 1.7 (m, 3H), 1.4 (q, 2H), 1.1 (m, 2H) | 387 |

-continued
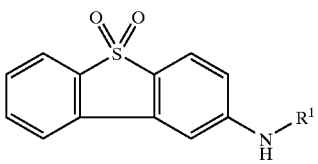
| Ex | R¹ | N. M. R. | MS |
|---|---|---|---|
| 83 | 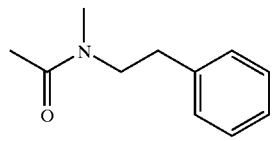 | 8.79 (s, 1H), 8.19 (s, 1H), 7.93 (m, 2H), 7.78 (m, 2H), 7.65 (m, 2H), 7.27 (m, 4H), 7.18 (m, 1H), 3.79 (t, 2H), 2.98 (s, 3H), 2.84 (t, 2H) | 393 |
| 84 | 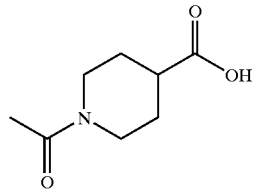 | 9.10 (s, 1H), 8.11 (d, 1H), 7.92 (m, 2H), 7.78 (m, 2H), 7.65 (m, 2H), 4.07 (m, 2H), 2.98 (m, 2H), 2.42 (m, 1H), 1.89 (m, 2H), 1.50 (m, 2H) | 387 |
| 85 | 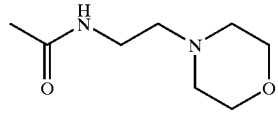 | 9.18 (s, 1H), 8.14 (d, 1H), 7.96 (m, 1H), 7.90 (m, 1H), 7.76 (m, 2H), 7.64 (t, 1H), 7.52 (dd, 1H), 6.35 (t, 1H), 3.57 (t, 2H), 3.24 (m, 2H), 2.40 (m, 6H) | 388 |
| 86[1] | 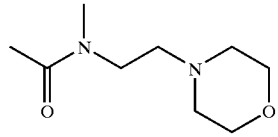 | 9.20 (s, 1H), 8.20 (d, 1H), 7.92 (m, 2H), 7.79 (m, 2H), 7.65 (m, 2H), 3.53 (m, 4H), 3.47 (t, 2H), 3.00 (s, 3H), 2.44 (m, 4H) | 402 |
| 87[2] | 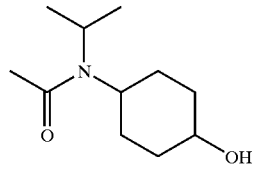 | 8.62 (s, 1H), 8.13 (s, 1H), 7.93 (m, 2H), 7.77 (m, 2H), 7.62 (m, 2H), 4.52 (d, 1H), 3.82 (m, 1H), 3.39 (m, 2H), 2.00 (m, 2H), 1.84 (m, 2H), 1.55 (m, 2H), 1.33 (m, 1H), 1.28 (d, 6H) | 415 |
| 88[3] | 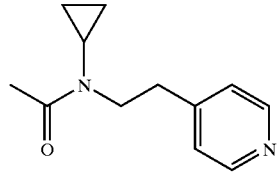 | 8.75 (s, 1H), 8.47 (d, 2H), 8.24 (s, 1H), 7.93 (m, 2H), 7.80 (m, 1H), 7.70 (m, 2H), 7.66 (m, 1H), 7.28 (d, 2H), 3.62 (t, 2H), 2.90 (t, 2H), 2.65 (m, 1H), 0.91 (m, 2H), 0.72 (m, 2H) | 420 |
| 89 | 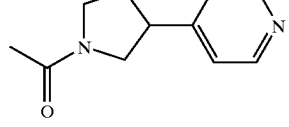 | 8.79 (s, 1H), 8.51 (d, 2H), 8.27 (s, 1H), 7.92 (d, 2H), 7.78 (m, 3H), 7.63 (t, 1H), 7.35 (d, 2H), 3.94 (t, 1H), 3.67 (t, 1H), 3.44 (m, 3H), 2.32 (m, 1H), 2.01 (m, 1H) | 406 |
| 90 | 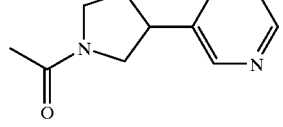 | 8.79 (s, 1H), 8.57 (s, 1H), 8.44 (d, 1H), 8.28 (s, 1H), 7.91 (d, 2H), 7.78 (m, 4H), 7.61 (t, 1H), 7.35 (m, 1H), 3.96 (t, 1H), 3.69 (t, 1H), 3.46 (m, 3H), 2.32 (m, 1H), 2.02 (m, 1H) | 406 |

-continued
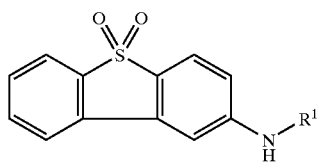
| Ex | R¹ | N. M. R. | MS |
|---|---|---|---|
| 91[4] |  | 9.3 (s, 1H), 8.2 (d, 1H), 7.95 (m, 2H), 7.85 (d, 1H), 7.75(t, 1H), 7.65 (m, 2H), 3.65 (m, 4H), 2.0 (m, 4H) | 379 |
[1]Amine: Tetrahedron, 1992, 48(11), 1999–2012
[2]Amine: Tetrahedron Lett., 1995, 36(10), 1709–1712
[3]Amine: Method 12
[4]Amine: Chem. Pharm. Bull., 1993, 41(11), 1971–1986
| Ex | R¹ | MS | Amine Preparation Reference |
|---|---|---|---|
| 92 | | 331 | WO 0109138 |
| 93 | | 341 | Commercially Available |
| 94 | | 409 | Method 13 |
| 95 | trans | 403 | Method 17 |
| 96 | | 425 | US 4798892 |
| 97 | | 419 | Commercially Available |

-continued

| Ex | R¹ | MS | Amine Preparation Reference |
|---|---|---|---|
| 98 | | 347 | J. Org. Chem., 1990, 55(24), 5935–5936. |
| 99 | | 415 | WO 9418182 |
| 100 | | 451 | Heterocycles, 2000, 53(4), 797–804. |
| 101 | | 394 | Commercially Available |
| 102 | | 464 | Commercially Available |
| 103 | | 428 | DE 3440195 |
| 104 | | 416 | Commercially Available |
| 105 | | 420 | Bull. Soc. Chim. Fr., 1996, 133(4), 369–379. |

-continued

| Ex | R¹ | MS | Amine Preparation Reference |
|---|---|---|---|
| 106 | | 442 | Commercially Available |
| 107 | | 421 | Commercially Available |
| 108 | | 377 | Commercially Available |
| 109 | | 347 | Commercially Available |
| 110 | | 369 | Commercially Available |
| 111 | | 381 | Commercially Available |
| 112 | | 373 | Commercially Available |
| 113 | | 387 | Commercially Available |
| 114 | | 415 | Collect. Czech. Chem. Commun., 1986, 51(11), 2598–2616 |

-continued
| Ex | R¹ | MS | Amine Preparation Reference |
|---|---|---|---|
| 115 | 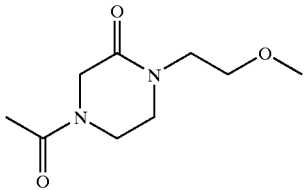 | 416 | WO 9727188 |
| 116 | 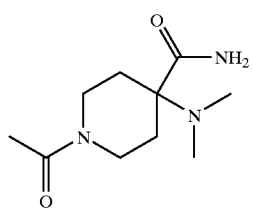 | 429 | JP 03188030 |
| 117 | 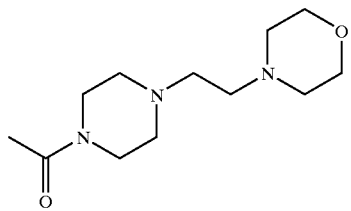 | 429 | Commercially Available |
| 118 | 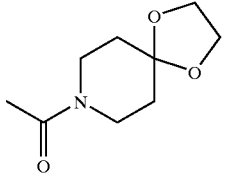 | 401 | Commercially Available |
| 119 | 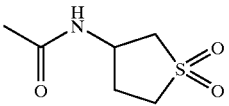 | 393 | Commercially Available |
| 120 | 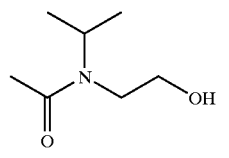 | 361 | Commercially Available |
| 121 | 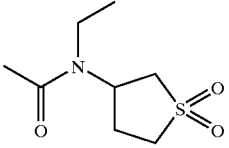 | 421 | Commercially Available |
| 122 | 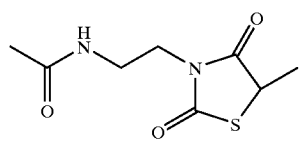 | 432 | Indian J. Chem., 1972, 10(7), 766–777. |

-continued

| Ex | R¹ | MS | Amine Preparation Reference |
|---|---|---|---|
| 123 | 2-methylpyrimidin-4-yl piperazine with N-acetyl | 436 | DE 3905364 |
| 124 | tetrafluoropyridin-4-yl piperazine with N-acetyl | 493 | Method 19 |
| 125 | pyrimidin-4-yl piperazine with N-acetyl | 422 | WO 9811128 |
| 126 | 1-acetyl-3-(cyanomethyl)piperidine | 382 | Method 21 |
| 127 | tert-butyl (2-acetamidoethyl)carbamate | 416 | Commercially Available |
| 128 | 1-acetyl-4-(2-oxo-1,3-oxazinan-3-yl)piperidine | 442 | WO 0039114 |
| 129 | N-(2-acetamidoethyl)propane-2-sulfonamide | 424 | DE 2362568 |

-continued

| Ex | R¹ | MS | Amine Preparation Reference |
|---|---|---|---|
| 130 | | 373 | J. Org. Chem., 1987, 52(1), 15–18. |
| 131 | | 455 | Commercially Available |
| 132 | | 386 | Commercially Available |
| 133 | | 388 | Tetrahedron Lett., 1995, 36(8), 1267–1270. |
| 134 | (R)-enantiomer | 372 | J. Med. Chem., 1985, 28(11), 1558–1564. |
| 135 | | 425 | Commercially Available |
| 136 | | 463 | Commercially Available |
| 137 | | 372 | Commercially Available |
| 138 | | 434 | Commercially Available |

-continued

| Ex | R¹ | MS | Amine Preparation Reference |
|---|---|---|---|
| 139 | | 433 | J. Med. Chem. (1998), 41(26), 5320–5333 |
| 140 | | 422 | Commercially Available |
| 141 | | 424 | Commercially Available |
| 142 | | 418 | Commercially Available |
| 143 | | 394 | Acta Chim. Hung. (1989), 126(4), 441–54. |
| 144 | | 462 | Commercially Available |
| 145 (R)-enantiomer | | 448 | Commercially Available |
| 146 | | 436 | DE 2625468 |

-continued
| Ex | R¹ | MS | Amine Preparation Reference |
|---|---|---|---|
| 147 | 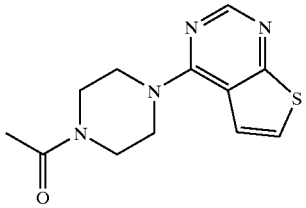 | 478 | Commercially Available |
| 148 | 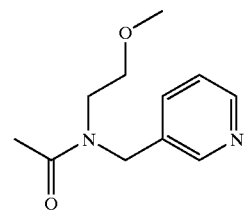 | 424 | WO 9109857 |
| 149 | 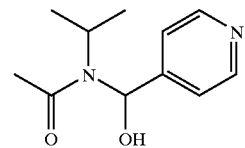 | 438 | J. Med. Chem., 1972, 15(12), 1321–1324. |
| 150 | 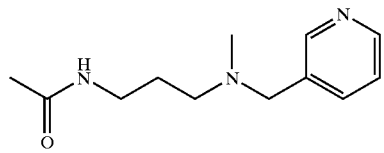 | 437 | EP 421762 |
| 151 | 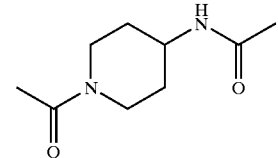 | 400 | US 5914405 |
| 152 | 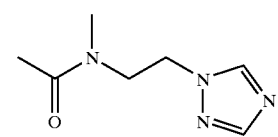 | 384 | Method 23 |
| 153 | 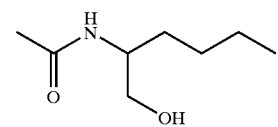 | 375 | Chem. Phys. Lipids, 1992, 61(2), 199–208. |
| 154 | 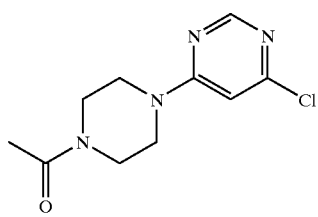 | 456 | WO 9806705 |

-continued
| Ex | R¹ | MS | Amine Preparation Reference |
|---|---|---|---|
| 155 | 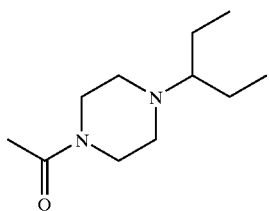 | 414 | Commercially Available |
| 156 | 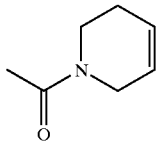 | 341 | Commercially Available |
| 157 | 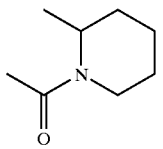 | 357 | Commercially Available |
| 158 | 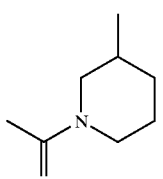 | 357 | Commercially Available |
| 159 | 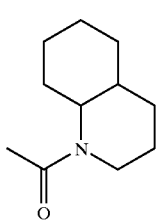 | 397 | Commercially Available |
| 160 | 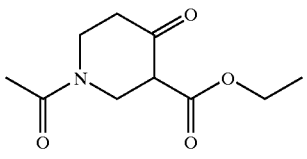 | 429 | Commercially Available |
| 161 | 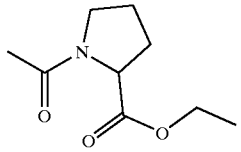 | 401 | Khim. -Farm. Zh., 1984, 18(12), 1445–1448. |
| 162 | 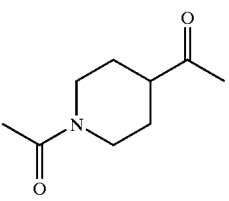 | 385 | Commercially Available |

-continued
| Ex | R¹ | MS | Amine Preparation Reference |
|---|---|---|---|
| 163 | 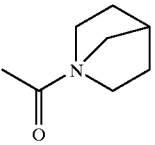 | 355 | Heterocycles, 1982, 19(11), 2155–2182. |
| 164 | 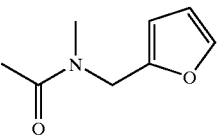 | 369 | Commercially Available |
| 165 | 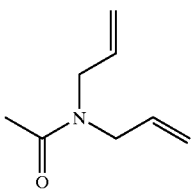 | 355 | Commercially Available |
| 166 | 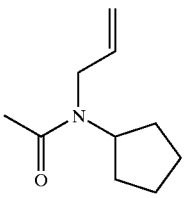 | 383 | Commercially Available |
| 167 | 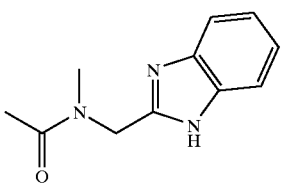 | 419 | J. Med. Chem., 1991, 34(11), 3212–3228. |
| 168 | 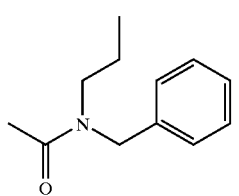 | 407 | Commercially Available |
| 169 | 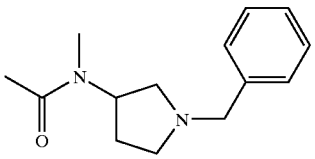 | 407 | Commercially Available |
| 170 | 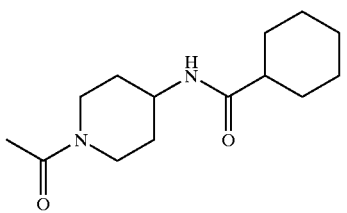 | 468 | Commercially Available |

-continued
| Ex | R¹ | MS | Amine Preparation Reference |
|---|---|---|---|
| 171 | 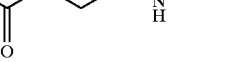 | 430 | Commercially Available |
| 172 | 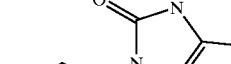 | 475 | Commercially Available |
| 173 | 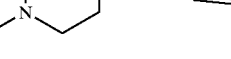 | 450 | Commercially Available |
| 174 | 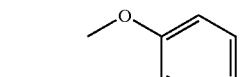 | 357 | Commercially Available |
| 175 | 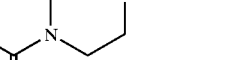 | 379 | Commercially Available |
| 176 | 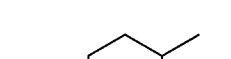 | 413 | Commercially Available |
| 177 | 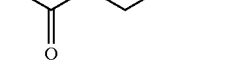 | 413 | Commercially Available |
| 178 | 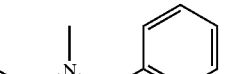 | 452 (M − H)⁻ | Commercially Available |

-continued

| Ex | R¹ | MS | Amine Preparation Reference |
|---|---|---|---|
| 179 | 3-methoxyphenyl-acetylpiperazine | 448 (M − H)⁻ | Commercially Available |
| 180 | 4-methoxyphenyl-acetylpiperazine | 448 (M − H)⁻ | Commercially Available |
| 181 | 4-chlorophenyl-acetylpiperazine | 452 (M − H)⁻ | Commercially Available |
| 182 | 1-acetyl-4-(2-oxo-2,3-dihydro-1H-benzimidazol-1-yl)-1,2,3,6-tetrahydropyridine | 473 | Commercially Available |
| 183 | N-methyl-N-(3-chlorobenzyl)acetamide | 413 | Commercially Available |
| 184 | N-(1-cyclohexylethyl)acetamide | 385 | Commercially Available |
| 185 | N-methyl-N-[2-(3,4-dimethoxyphenyl)ethyl]acetamide | 453 | Commercially Available |

-continued

| Ex | R¹ | MS | Amine Preparation Reference |
|---|---|---|---|
| 186 | (allyl-N-acetyl-3-aminotetrahydrothiophene 1,1-dioxide) | 433 | Commercially Available |
| 187 | (4-phenylpiperidine N-acetyl) | 419 | Commercially Available |
| 188 | (N-methyl-N-acetyl-(5-phenyl-1H-pyrazol-3-yl)methylamine) | 445 | Commercially Available |
| 189 | (N-methyl-N-acetyl-4-fluorobenzylamine) | 397 | J. Chem. Soc., Perkin Trans. 1, 1998, 16, 2527–2532. |
| 190 | (N-methyl-N-acetyl-1-(2-methoxyphenyl)propan-2-amine) | 437 | Commercially Available |
| 191 | (1-acetyl-4-(5-(furan-2-yl)-1H-pyrazol-3-yl)piperidine) | 475 | Khim. -Farm. Zh., 1987, 21(7), 808–811. |

Example 192

5,5-Dioxo-2-[4-(morpholinocarbonyl)piperidinocarbonylamino]dibenzothiophene 5,5-Dioxo-2-(4-carboxypiperidinocarbonylamino)dibenzothiophene (Example 84; 75 mg, 0.19 mmol), DMF (2.5 ml), morpholine (16.5 mg, 0.19 mmol), EDAC (44 mg, 0.23 mmol), 1-hydroxybenzotriazole hydrate (25.65 mg, 0.19 mmol) were stirred together for 18 hours. The solvent was removed under vacuum and the residue partitioned between H₂O/EtOAc. The organic layers were washed with water, saturated aqueous NaHCO₃ then brine, and then dried, filtered and evaporated to an amorphous solid. NMR: 9.08 (s, 1H)) 8.21 (d, 1H), 7.93 (m, 2H), 7.79 (m, 2H), 7.65 (m, 2H), 4.14 (m, 2H), 3.52 (m, 6H), 3.45 (m, 2H), 2.92 (m, 3H), 1.68 (m, 2H), 1.53 (m, 2H); m/z 456.73.

Example 193

5,5-Dioxo-2-[4-(N,N-dimethylcarbamoyl)piperidinocarbonylamino]dibenzothiophene

The title compound was prepared by the procedure of Example 192 using dimethylamine (1 equivalent) in place of morpholine. NMR: 9.08 (s, 1H), 9.19 (d, 1H), 7.93 (m, 2H), 7.77 (m, 2H), 7.65 (m, 2H), 4.15 (m, 2H), 3.07 (s, 3H), 2.94 (m, 3H), 1.68 (m, 2H), 1.52 (m, 2H); m/z 414.71.

Reference Examples

The following compounds are provided as a further feature of the invention.

Reference Example 1

5,5-Dioxo-2-[(2,2,2-trifluoro-1-hydroxy-1-methylethyl)carbonylamino]dibenzothiophene J Med Chem, (1997), 40 (6), 1048.

Reference Example 2
2-Acetamidodibenzothiophene

The title compound was prepared following the procedure of Example 2 using 2-aminodibenzthiophene (Bull. Soc. Chim. Fr. (1996), 133(6), 597–610) and acetyl chloride. NMR: 10.13 (brs, 1H), 8.6 (d, 1H), 8.15 (m, 1H), 8.0 (m, 1H), 7.9 (d, 1H), 7.6 (dd, 1H), 7.5 (m, 2H), 2.1 (s, 3H); m/z 242.

Reference Example 3
5,5-Dioxo-2-acetamidodibenzothiophene

The title compound was prepared following the procedure of Example 31 using 2-acetamidodibenzothiophene (Reference Example 2) as the starting material. NMR: 10.48 (brs, 1H), 8.3 (d, 1H), 7.9 (m, 3H), 7.8 (t, 1H), 7.7 (dd, 1H), 7.6 (t, 1H), 2.1 (s, 3H); m/z 274.

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1
3-(Pyridin-4-yl)propanoic acid

To a solution of ethyl 3-pyridin-4-ylpropanoate (Method 2; 103.1 g, 576 mmol) in water (400 ml) and ethanol (20 ml) at room temperature was added potassium hydroxide (60 g, 1600 mmol). After 18 hours hydrochloric acid (100 ml) was added to give a white solid. Yield 62.8 g (73%). NMR 8.38 (d, 2H), 7.21 (d, 2H), 2.70 (t, 2H), 2.52 (t, 2H); m/z 152.2.

Method 2
Ethyl 3-pyridin-4-ylpropanoate

Ethyl (E)-3-pyridin-4-ylprop-2-enoate (Method 3; 102.3 g, 576 mmol) in methanol (300 ml) was hydrogenated using palladium on carbon 5% (9.0 g) under atmospheric pressure hydrogen for 72 hours. The catalyst was filtered off through diatomaceous earth and the filtrate concentrated to give a yellow oil. Yield 103.1 g (99%). NMR (CDCl$_3$) 8.50 (d, 2H), 7.15 (d, 2H), 4.12 (q, 2H), 2.95 (t, 2H), 2.64 (t, 2H), 1.21 (t, 3H); m/z 180.4.

Method 3
Ethyl (E)-3-pyridin-4-ylprop-2-enoate

To a solution of 4-pyridinecarboxaldehyde (67 ml, 700 mmol) and triethyl phosphonacetate (152 ml, 770 mmol) in THF (200 ml) at room temperature was added lithium hydroxide (32.4 g, 770 mmol). After 18 hours ether (500 ml) was added and the solution was washed with sodium hydrogen carbonate, brine and concentrated to give a white solid. Yield 102.1 g (83%). NMR: 8.62 (d, 2H), 7.60 (d, 1H), 7.35 (d, 2H), 6.59 (d, 1H), 4.30 (q, 2H), 1.35 (t, 3H); m/z 178.3.

Method 4
1-Carboxymethyl-3-benzyl-2-pyrrolidinone

A mixture of 3-benzyl-1-(ethoxycarhonylmethyl)-2-pyrrolidinone (Method 5; 0.70 g, 2.68 mmol) and 2 M NaOH (4 ml) was stirred in ethanol (10 ml) for 24 hours. The mixture was evaporated in vacuo and the residue acidified. The product was collected by filtration and dried under high vacuum. NMR (90 MHz, CDCl$_3$) 7.9 (s, 1H), 7.2 (m, 5H), 4.1 (d, 1H), 3.3 (m, 2H), 2.25 (m, 2H), 2.3–1.6 (m, 4H).

Method 5
3-Benzyl-1-(ethoxycarbonylmethyl)-2-pyrrolidinone

NaH (50%, 0.214 g, 4.5 mmol) was added to a solution of 3-benzyl-2-pyrrolidinone (Synthesis, 1996, 8, 941–948; 0.68 g, 3.9 mmol) in THF (15 ml). The solution was stirred at room temperature for 30 minutes. Ethyl bromoacetate (0.48 ml, 4.3 mmol) was added and the mixture stirred for 12 hours. The solvent was removed in vacuo and the residue purified by chromatography eluting with 50% EtOAc in hexane to give the product as a light yellow oil. NMR (90 MHz, CDCl$_3$) 7.2 (m, 5H), 4.2 (m, 3H), 3.25 (m, 1H), 2.75 (m, 2H), 2.3–1.6 (m, 4H), 1.3 (t, 3H).

Method 6
1-(2-Carboxypropyl)-1,2,4-triazole

A mixture of 1,2,4-triazole (27.6 g) and methacrylic acid (34.4 g) in pyridine (40 ml) was heated at 140° C. for 6 hours. The precipitate was dissolved in hot hydrochloric acid (1%, 400 ml). Charcoal was added and the mixture was filtered hot. The solution was concentrated in vacuo and the colourless solid collected by filtration and washed with cold water. NMR (90 MHz): 8.48 (s, 1H), 7.98 (s, 1H), 4.32 (m, 2H), 2.94 (m, 1H), 1.01 (d, 3H).

Method 7
3-Methyl-3-pyridin4-ylpropanoic acid

Sodium hydroxide (0.19 g, 4.8 mmol) was added to a solution of ethyl 3-methyl-3-pyridin-4-ylpropanoate (Method 8; 0.501 g, 2.6 mmol) in MeOH (10 ml) and water (5 ml). The mixture was stirred at room temperature for 18 hours. The solvent was removed in vacuo and the residue shaken with 1 M hydrochloric acid (4.8 ml). The solvent was removed in vacuo to leave a colourless solid. M/z 164 (M–H)$^-$.

Method 8
Ethyl 3-methyl-3-pyridin-4-ylpropanoate

To a solution of ethyl 3-methyl-3-pyridin-4-ylprop-2-enoate (Method 9; 8.4 g, 44 mmol) in ethanol (150 ml) was added 5% palladium on charcoal. The mixture was stirred under an atmosphere of hydrogen for 18 hours. The mixture was filtered through diatomaceous earth and the filtrate evaporated to leave a colourless oil. The crude product was purified by chromatography eluting with 30–50% EtOAc in hexane to give the product as a colourless oil. M/z 194.

Method 9
Ethyl 3-methyl-3-pyridin-4-ylprop-2-enoate

4-Acetyl pyridine (9 ml, 83 mmol) was added to a cooled solution of triethylphosphonoacetate (16.5 ml, 83 mmol) and lithium bis(trimethylsilyl)amide (1 M in THF, 90 ml, 90 mmol) in THF (100 ml) at 0° C. The mixture was allowed to warm to room temperature and poured into water. The mixture was extracted with EtOAc. The organic layers were dried and evaporated in vacuo. The crude product was purified by chromatography eluting with 30–50% EtOAc in hexane to give the product as a yellow oil. M/z 192.

Method 10
2-Amino-1-methyldibenzothiophene

1-Methyl-2-nitrodibenzothiophene (Method 11; 0.855 g, 3.52 mmol) was stirred in ethanol (50 ml) and EtOAc (50 ml) under an argon atmosphere. 10% Palladium on carbon (0.09 g) was added to the solution and the reaction mixture was stirred under a hydrogen atmosphere at room temperature for 3 h. The mixture was filtered through diatomaceous earth and washed with EtOAc before the filtrate was evaporated in vacuo. The crude product was purified by flash chromatography eluting with 50% DCM/iso-hexane-DCM. Evaporation of the appropriate fractions left the product as a colourless solid. NMR: 8.39 (m, 1H), 7.92 (m, 1H), 7.50 (m, 1H), 7.42 (m, 2H), 6.92 (d, 1H), 4.98 (brs, 2H), 2.60 (s, 3H); m/z 215.

Method 11
1-Methyl-2-nitrodibenzothiophene

To a stirred suspension of 2-nitrodibenzothiophene (2.20 g, 9.61 mmol) in dry THF (100 ml) at −15° C. was slowly added methyl magnesium chloride (3 M solution in THF; 9.6 ml, 29 mmol). After stirring at this temperature for 5.5 h, 2,3-dichloro-5,6-dicyano-1,4-benzoquinone (6.98 g, 30.75 mmol) was added portion wise, keeping the temperature below −10° C. The mixture was allowed to warm to room temperature and stirred for 16 h. The reaction mixture was diluted with water and extracted into DCM. The organic layers were further washed with water, dried and purified by chromatography (eluent—50% DCM /isohexane) to give the title compound as a yellow solid. NMR: 8.52 (m, 1H), 8.12 (m, 2H), 7.94 (d, 1H), 7.61 (m, 2H), 2.92 (s, 3H).

Method 12

4-(2-cyclopropylaminoethyl)pyridine

4-Vinyl pyridine (50 mmol), glacial acetic acid (3 ml), cyclopropylamine (4.28 g, 75 mmol) and water (12.8 ml) were heated at 50° C. for 22 hours. The crude reaction products partitioning, the organic phase was washed with water, brine and dried. Filtered and solvents removed under vacuum. The residue was further distilled under vacuum (Kugelrohr) and the product amine collected. NMR (CDCl$_3$) 8.45 (m, 2H), 7.05 (m, 2H), 2.93 (m, 2H), 2.73 (m, 2H), 2.07 (m, 1H), 1.37 (m, 2H), 1.25 (m, 2H); m/z 163.17.

Method 13

N-Methyl-N-(3-mesylpropyl)amine

Ethereal HCl (22.5 ml, 1 M solution) was added to a stirred solution of N-methyl-N-(3-mesylpropyl)-N-(benzyloxycarbonyl)amine (Method 14; 5 g) in methanol (100 ml). 10% Pd/C (1.25 g) was added and the mixture was stirred under an atmosphere of hydrogen for 2 hrs. The catalyst was removed by filtration and the filtrate evaporated to dryness. Trituration with ether gave the product as a white solid. NMR (DMSO-d$_6$+d$_4$-acetic acid) 2.11 (m, 2H), 2.59 (s, 3H), 3.0 (s, 3H), 3.05 (t, 2H); m/z 152.

Method 14

N-Methyl-N-(3-mesylpropyl)-N-(benzyloxycarbonyl)amine 3-chloroperoxybenzoic acid (19.2 g) was added portion-wise to a stirred solution of N-methyl-N-(3-methylthiopropyl)-N-(benzyloxycarbonyl)amine (Method 15; 9 g) in DCM (250 ml). When the addition was completed the reaction was stirred as ambient temperature for 16 hours. The mixture was washed with sat. sodium bicarbonate solution (2×100 ml), brine, dried and evaporated to dryness. The residue was purified by flash column chromatography eluting with EtOAc/iso-hexane(1:1, 3:1) and EtOAc to give the product as a solid foam. NMR (CDCl$_3$) 2.1 (m, 2H), 2.7–3.1 (m, 8H), 3.45 (t, 2H), 5.13 (s, 2H), 7.35 (m, 5H); m/z 286.

Method 15

N-Methyl-N-(3-methylthiopropyl)-N-(benzyloxycarbonyl)amine

Sodium hydride (2.18 g, 60% in oil) was washed with iso-hexane and dried under a stream of nitrogen. DMA (50 ml) was added and the suspension was cooled to approx. 5° C. under an atmosphere of nitrogen. A solution of N-(3-methylthiopropyl)-N-(benzyloxycarbonyl)amine (Method 16; 10 g) in DMA (150 ml) was added dropwise keeping the temperature below 10° C. The reaction mixture was allowed to warm to ambient temperature, stirred for 30 mins. and then cooled to 0° C. Methyl iodide (8.9 g) was added dropwise and the reaction then stirred at ambient temperature for 16 hours. The solvent was evaporated under reduced pressure and the residue partitioned between ETOAc and sat. ammonium chloride solution. The organic layer was separated, washed with brine and dried. Evaporation under reduced pressure gave the product as a yellow oily gum. NMR (CDCl$_3$) 1.83 (m, 2H), 2.07 (brs, 3H), 2.45 (m, 2H), 2.94 (s, 3H), 3.37 (t, 2H), 5.12 (s, 2H), 7.34 (m, 5H); m/z 254.

Method 16

N-(3-Methylthiopropyl)-N-(benzyloxycarbonyl)amine

Benzyl chloroformate (17.8 g) was added dropwise to a cooled solution of 3-methyl thiopropylamine (10 g) and triethylamine (10.6 g) in DCM (250 ml). The reaction mixture was kept at 0° C. during the addition and then at ambient temperature for 16 hours. The mixture was washed with aqueous citric acid (1 M, 100 ml), brine and dried. The residue was chromatographed eluting with EtOAc/iso-hexane(7:3) to give the product as a colourless gum. NMR (CDCl$_3$) 1.8 (m, 2H), 2.08 (s, 3H), 2.52 (t, 2H), 3.3 (m, 2H), 4.9 (brs, 1H), 5.1 (s, 2H), 7.35 (m, 5H); m/z 240.

Method 17

4-Methyl-4-hydroxy-3-methylaminotetrahydropyran.

A solution 4-methyl-3,4-epoxytetrahdropyran (Method 18; 26 g) and methylamine (33%) in ethanol (250 ml) was allowed to stand at room temperature for 5 days. The mixture was evaporated and the residue recrystallized from toluene (170 ml). M/z 145 [M$^+$]; m.p. (toluene) 110–12° C.

Method 18

4-Methyl-3,4-epoxytetrahdropyran 5,6-Dihydro-4-methyl-2H-pyran (Bull. Soc. Chim. Fr., 1967, 8, 2989–96; 30 g) was dissolved in DCM (500 ml). M-chloroperoxybenzoic acid (63 g) was added over 20 minutes and the mixture was then refluxed for 4 hours. The solid was filtered and the filtrate washed with 10% sodium sulphite, 10% sodium hydroxide, brine and then the organic layer was dried and evaporated to leave the product as an oil which was used without further purification.

Method 19

1-(2,3,5,6-Tetrafluoropyridin-4-yl)piperazine hydrochloride

To an ice bath cooled, stirred solution of 1-(2,3,5,6-tetrafluoropyridin-4-yl)-4-benzylpiperazine (Method 20; 4.59 g, 14.1 mmol) in 1,2-dichloroethane (40 ml) was added chloroethyl chloroformate (1.6 ml, 14.7 mmol) over five minutes. The solution was heated to reflux and stirred for two hours and allowed to cool to ambient temperature. Volatile material was removed by evaporation. The residue was dissolved in methanol, heated to reflux and stirred for 2.5 hours, allowed to cool to ambient temperature. Volatile material was removed by evaporation. The residue was purified by chromatography eluting with 5–10% MeOH in DCM to give a solid which was triturated with ether to give the title compound (2.57 g) as a solid. NMR 3.05 (m, 4H), 3.53 (m, 4H); m/z 236.

Method 20

1-(2,3,5,6-Tetrafluoropyridin-4-yl)-4-benzylpiperazine

To a solution of pentafluoropyridine (1.76 ml, 16.0 mmol) and 1-benzylpiperazine (2.64 g, 15.0 mmol) in DMSO (20 ml) was added potassium carbonate (4.20 g, 30.4 ml). The suspension was heated to 100° C. and stirred for five hours and allowed to cool to ambient temperature, poured onto water and then extracted with DCM. The extract was washed with brine, water, and dried. Volatile material was removed by evaporation to give the title compound (4.59 g) as an oil. NMR (CDCl$_3$) 2.58 (m, 4H), 3.52 (m, 4H), 3.57 (s, 2H), 7.24–7.38 (m, 5H and CDCL$_3$); m/z 326.

Method 21

3-Cyanomethylpiperidine

1-Benzyloxycarbonyl-3-cyanomethylpiperidine (Method 22; 12.5 g) was dissolved in ethanol (20 ml) and ethereal HCl (1 ml) and 5% palladium on charcoal (2.0 g) was added. The mixture was shaken under an atmosphere of hydrogen for 2.5 hours. The catalyst was filtered and the filtrate evaporated in vacuo. The crude product was dissolved in ethanol and recrystallized from ether. M/z 124 [M$^+$].

Method 22

1-Benzyloxycarbonyl-3-cyanomethylpiperidine

1-Benzyloxycarbonyl-3-mesyloxymethylpiperidine (WO 0100207; 8.4 g) was dissolved in DMSO (100 ml) and sodium cyanide (1.6 g) was added. The mixture was heated to 100° C. and stirred continuously under an argon atmosphere for 6 hours. The mixture was cooled and poured into water (200 ml). The product was extracted with EtOAc, washed with ferrous sulphate solution (10% w/w), dried and evaporated in vacuo. TLC (40% EtOAc/petroleum ether (60/80) Rf. 0.54.

Method 23

1-(2-Methylaminoethyl)-1,2,4-triazole

To a cooled solution (ice bath) of 1-{2-[N-methyl-N-(t-butoxycarbonyl)amino]ethyl}-1,2,4-triazole (Method 24; 1.6 g, 7.2 mmol) in DCM (10 ml) was added trifluoroacetic acid (5 ml). The reaction mixture was stirred for 3 hours at 0° C. and then at room temperature for 1 hour. The reaction mixture was evaporated to dryness with toluene and the crude product was dissolved in DCM (3 ml) and concentrated HCl in ether was added dropwise under vigorous stirring to yield the title compound as a white solid M/z 126.9.

Method 24

1-{2-[N-Methyl-N-(t-butoxycarbonyl)amino]ethyl}-1,2,4-triazole

To a cooled solution (ice bath) of 2-[N-methyl-N-(t-butoxycarbonyl)amino]ethanol (J. Med. Chem., 1999, 42(11), 2007–2020; 5 g, 28 mmol), triphenyl phosphine (9.35 g, 36 mmol) and 1,2,4-triazole (1.64 g, 24 mmol) in DCM (30 ml) was added diethylazodicarboxylate (5.64 ml, 35.7 mmol) dropwise. The ice bath was removed and the reaction mixture allowed to stir at room temperature for 1 hour. The precipitate was discarded and the filtrate was concentrated and purified by flash chromatography, eluting with a 50% EtOAc/DCM and then 100% EtOAc to give a pale yellow oil which was used without further purification.

Example 194

The following illustrate representative pharmaceutical dosage forms containing the compound of formula (1), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph. Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A method of treating a disorder mediated by the neuropeptide Y5 receptor in a warm-blooded animal in need of such treatment, comprising administering to said animal a therapeutically effective amount of a compound of formula (I):

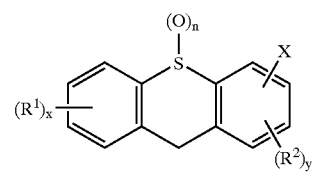

wherein:

X is a group of formula (A):

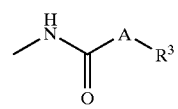

$R^1$ is cyano, halo, trifluoromethyl, trifluoromethoxy, $C_{1-4}$alkyl, $C_{1-4}$alkoxy, N-($C_{1-4}$alkyl)amino or N,N-($C_{1-4}$ alkyl)$_2$amino;

$R^2$ is halo, cyano, hydroxy, trifluoromethyl, trifluoromethoxy, $C_{1-4}$alkyl or $C_{1-4}$alkoxy;

A is —$NR^a$—, —O— or a direct bond; wherein $R^a$ is hydrogen, $C_{1-10}$alkyl, $C_{2-10}$alkenyl, $C_{2-10}$alkynyl; wherein $R^a$ may be optionally substituted by one or more $R^5$;

$R^3$ is hydrogen, $C_{1-10}$alkyl, $C_{2-10}$alkenyl or $C_{2-10}$alkynyl wherein $R^3$ may be optionally substituted by one or more $R^6$; or $R^3$ is carbocyclyl or heterocyclyl wherein $R^3$ may be optionally substituted on carbon by one or more $R^7$; and wherein if said heterocyclyl contains an —NH— moiety, that nitrogen may be optionally substituted by $R^8$;

$R^5$ and $R^6$ are independently selected from halo, hydroxy, cyano, carbamoyl, ureido, amino, nitro, carboxy, carbamoyl, mercapto, sulphamoyl, aminosulphamoyl, $C_{1-6}$alkoxy, $C_{1-6}$alkanoyl, $C_{1-6}$alkanoyloxy, $C_{1-6}$alkanoylamino, $C_{2-6}$alkenyloxycarbonyl, $C_{1-6}$alkoxycarbonyl, heterocyclyl, heterocyclyloxy, heterocyclylamino, heterocyclyl-N-($C_{1-6}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-6}$alkyl)amino, carbocyclylsulphonyl, carbocyclylcarbonyl, carbocyclylcarbonylamino, carbocyclyloxycarbonyl, N-($C_{1-6}$alkyl)amino, N,N-($C_{1-6}$alkyl)$_2$amino, $C_{1-6}$alkoxycarbonylamino, N-($C_{1-6}$alkyl)carbamoyl, N,N-($C_{1-6}$alkyl)$_2$carbamoyl, $C_{1-6}$alkylS(O)$_a$ wherein a is 0–2, N-($C_{1-6}$alkyl)sulphamoylamino, N,N-($C_{1-6}$alkyl)$_2$sulphamoylamino, $C_{1-6}$alkylsulphonylamino, ($C_{1-6}$alkyl)sulphonyl-N-($C_{1-6}$alkyl)amino, N-($C_{1-6}$alkyl)sulphamoyl and N,N-($C_{1-6}$alkyl)$_2$sulphamoyl; wherein $R^5$ and $R^6$ may be optionally substituted on carbon by one or more $R^9$; and wherein if said heterocyclyl contains an —NH— moiety, that nitrogen may be independently optionally substituted by $R^{10}$;

$R^7$ and $R^9$ are independently selected from halo, hydroxy, cyano, carbamoyl, ureido, trifluoromethyl, trifluoromethoxy, amino, nitro, carboxy, carbamoyl, mercapto, sulphamoyl, aminosulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{1-4}$alkoxycarbonylamino, $C_{2-4}$alkenyloxycarbonyl, $C_{1-4}$alkanoyl, $C_{1-4}$alkanoylamino, $C_{1-4}$alkanoyloxy, N-($C_{1-4}$alkyl)amino, N,N-($C_{1-4}$alkyl)$_2$amino, N-($C_{1-4}$alkyl)carbamoyl, N,N-($C_{1-4}$alkyl)$_2$carbamoyl, $C_{1-4}$alkylS(O)$_a$ wherein a is 0–2, N-($C_{1-4}$alkyl)sulphamoylamino, N,N-($C_{1-4}$alkyl)$_2$sulphamoylamino, ($C_{1-4}$alkyl)sulphonylamino, ($C_{1-4}$alkyl)sulphonyl-N-($C_{1-4}$alkyl)amino, N-($C_{1-4}$alkyl)sulphamoyl, N,N-($C_{1-4}$alkyl)$_2$sulphamoyl, heterocyclyl, heterocyclyloxy, heterocyclylamino, heterocyclyl-N-($C_{1-4}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-4}$alkyl)amino, carboocyclylsulphonyl, carbocyclylcarbonyl, carbocyclylcarbonylamino, and carbocyclyloxycarbonyl; wherein $R^7$ and $R^9$ may be independently optionally substituted on carbon by one or more $R^{11}$;

$R^8$ and $R^{10}$ are independently selected from $C_{1-4}$alkyl, $C_{1-4}$alkanoyl, sulphamoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)$_2$carbamoyl, N-($C_{1-4}$alkyl)sulphamoyl, N,N-($C_{1-4}$alkyl)$_2$sulphamoyl, heterocyclyl, heterocyclylcarbonyl, heterocyclyloxycarbonyl, heterocyclylsulphonyl, carbocyclyl, carbocyclylcarbonyl, carbocyclyloxycarbonyl and carbocyclylsulphonyl; wherein $R^8$ and $R^{10}$ may be independently optionally substituted on carbon by one or more $R^{12}$;

$R^{11}$ and $R^{12}$ are independently selected from halo, hydroxy, cyano, carbamoyl, ureido, amino, nitro, carboxy, carbamoyl, mercapto, sulphamoyl, methyl, ethyl, vinyl, allyl, methoxy, ethoxy, vinyloxy, allyloxy, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

x is 0–4; wherein the values of $R^1$ may be the same or different;

y is 0–3; wherein the values of $R^2$ may be the same or different;

n is 0–2;

or a pharmaceutically acceptable salt, prodrug or solvate thereof;

with the provisos when X is a group of formula (A):

1) when $R^3$ is a nitrogen linked heterocyclyl, A is a direct bond;

2) when x and y are 0 and n is 2, the group $R^3$—A—C(O)—NH— is not 2-formamido, 2-acetamido, 3-acetamido, 2-propionamido, 3-[2-(fur-2-ylcarbonylmethyl)acetamido], 2-(2-phthalimidoacetamido), 2-(3-phthalimidopropionamido), 2-(2-phthalimido-2-isopropylacetamido), 2-(2-phthalimido-2-isobutylacetamido), 2-(2-phthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(2-phthalimidoacetamido), 3-(3-phthalimidopropionamido), 3-(2-phthalimido-2-isopropylacetamido), 3-(2-phthalimido-2-isobutylacetamido), 3-(2-phthalimido-2-benzylacetamido), 3-(2-aminoacetamido), 3-(3-aminopropionamido), 3-(2-amino-2-isopropylacetamido), 3-(2-amino-2-benzylacetamido) or 2-(3,3,3-trifluoro-2-hydroxy-2-methylpropionamido);

3) when x and y are 0 and n is 1, the group $R^3$—A—C(O)—NH— is not 3-acetamido, 3-(2-phthalimidoacetamido), 3-(3-phthalimidopropionamido), 3-(2-phthalimido-2-isopropylacetamido), 3-(2-phthalimido-2-isobutylacetamido), 3-(2-phthalimido-2-benzylacetamido), 3-(2-aminoacetamido), 3-(3-aminopropionamido), 3-(2-amino-2-isopropylacetamido), 3-(2-amino-2-isobutylacetamido) or 3-(2-amino-2-benzylacetamido);

4) when x and y are 0 and n is 0, the group $R^3$—A—C(O)—NH— is not 2-benzamido, 2-acetamido, 2-benzyloxycarbonylamino, 2-(2-phthalimidoacetamido), 2-(3-phthalimidopropionamido), 2-(2-phthalimido-2-isopropylacetamido), 2-(2-phthalimido-2-isobutylacetamido), 2-(2-phthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(trifluoroacetamido), 3-benzyloxycarbonylamino or 4-t-butyloxycarbonylamino;

5) when ($R^1$) is 7-fluoro, y is 0 and n is 2, the group $R^3$—A—C(O)—NH— is not 3-acetamido;

6) when x is 0, ($R^2$)$_y$ is 1-cyano and n is 0, the group $R^3$—A—C(O)—NH— is not 2-acetamido;

7) when x is 0, ($R^2$)$_y$ is 3-bromo and n is 0, the group $R^3$—A—C(O)—NH— is not 2-acetamido or 2-benzamido;

8) when x is 0, ($R^2$)$_y$ is 1-bromo and n is 0, the group $R^3$—A—C(O)—NH— is not 2-acetamido or 2-benzamido; and

99

9) when x is 0, (R²)ᵧ is 1-chloro or 4-chloro and n is 0, the group R³—A—C(O)—NH— is not 2-acetamido.

2. The method of claim 1, wherein X is in the 2-position of the dibenzothiophene ring.

3. The method of claim 1 or claim 2, wherein R² is halo, cyano or $C_{1-4}$alkyl.

4. The method of claim 1 or claim 2, wherein A is —NRᵃ—, —O— or a direct bond; wherein Rᵃ is hydrogen, $C_{1-10}$alkyl or $C_{2-10}$alkenyl; wherein Rᵃ may be optionally substituted by one or more R⁵; wherein R³ is $C_{1-10}$alkyl or $C_{2-10}$alkenyl wherein R³ may be optionally substituted by one or more R⁶; or R³ is carbocyclyl or heterocyclyl wherein R³ may be optionally substituted on carbon by one or more R⁷; and wherein if said heterocyclyl contains an —NH— moiety, that nitrogen may be optionally substituted by R⁸;

R⁵ and R⁶ are independently selected from hydroxy, cyano, amino, $C_{1-6}$alkoxy, heterocyclyl, heterocyclyloxy, carbocyclyl, carbocyclyloxy, carbocyclyl-N-($C_{1-6}$alkyl)amino, N,N-($C_{1-6}$alkyl)₂ amino, $C_{1-6}$alkoxycarbonylamino, $C_{1-6}$alkylS(O)ₐ wherein a is 0–2, N,N-($C_{1-6}$alkyl)₂sulphamoylamino and $C_{1-6}$alkylsulphonylamino; wherein R⁵ and R⁶ may be independently optionally substituted on carbon by one or more R⁹;

R⁷ and R⁹ are independently selected from halo, hydroxy, nitro, carboxy, carbamoyl, $C_{1-4}$alkyl, $C_{1-4}$alkoxy, $C_{1-4}$alkoxycarbonyl, $C_{1-4}$alkanoyl, $C_{1-4}$alkanoylamino, N,N-($C_{1-4}$alkyl)₂amino, N,N-($C_{1-4}$alkyl)₂carbamoyl, heterocyclyl, heterocyclylcarbonyl, carbocyclyl and carbocyclylcarbonylamino; wherein R⁷ and R⁹ may be independently optionally substituted on carbon by one or more R¹¹;

R⁸ is selected from $C_{1-4}$alkyl, $C_{1-4}$alkylsulphonyl, N,N-($C_{1-4}$alkyl)₂sulphamoyl, heterocyclyl and carbocyclyl; wherein R⁸ may be optionally substituted on carbon by one or more R¹²;

R¹¹ and R¹² are independently selected from halo, hydroxy, cyano, carbamoyl, methyl, methoxy, allyloxy, heterocyclyl and carbocyclyl; or a pharmaceutically acceptable salt, prodrug or solvate thereof.

5. The method of any one of claim 1, 2, 3, or 4, wherein the group R³—A— is methyl, 2-oxo-pyrrolidin-1-ylmethyl, 1,2,4-triazol-1-ylmethyl, 1,1-dioxotetrahydrothien-3-ylmethyl, 2-oxooxazolidin-3-ylmethyl, pyrid-3-yloxymethyl, 1,1-dioxothiomorpholinomethyl, cyanomethyl, 2-oxo-1,2-dihydropyrid-1-ylmethyl, 2-oxocyclopentylmethyl, succinimidomethyl, 3-benzyl-2-oxopyrrolidin-1-ylmethyl, 3-hydroxypyridazin-6-yloxymethyl, 2-pyrid-4-ylethyl, 2-methoxyethyl, 1-phenoxyethyl, 2-(1,2,4-triazol-1-yl)ethyl, 2-imidazol-1-ylethyl, succinimidoethyl, prop-2-yl, 3,3,3-trifluoro-2-hydroxyprop-2-yl, 1-morpholinoprop-2-yl, 1-pyrid-4-ylprop-2-yl, 2-aminoprop-2-yl, 2-(t-butoxycarbonylamino) prop-2-yl, 1-(1,2,4-triazol-1-yl)prop-2-yl, 2-pyrid-4-ylpropyl, 1-butyl, 1,1,1-trifluorobut-3-yl, 1-hydroxyhex-2-yl, cyclopropyl, 3-hydroxybicyclo[2.2.1]hept-2-yl, 4-nitrophenyl, morpholino, 4-methylpiperazin-1-yl, tetrahydropyran-4-yl, 4-hydroxymethylpiperidin-1-yl, 1-methyl-2-oxopyrrolidin4-yl, 2-(pyrrolidin-1-ylmethyl) pyrrolidinyl, 3-carbamoylpiperidin-1-yl, 3-hydroxyazetidin-1-yl, 2-(allyloxymethyl)morpholino, 4-(1,4-dihydrooxazin-2-one-3-yl)piperidin-1-yl, 4-(N,N-dimethylsulphamoyl) piperazin-1-yl, 4-hydroxyethylpiperidin-1-yl, 4-(tetrahydrofur-2-ylmethyl)piperazin-1yl, 4-(3-methoxypropyl)piperazin-1-yl, 4-pyrid-4-ylpiperidin-1-yl, 4-pyrid-2-ylpiperazin-1-yl, 3-(N,N-dimethylamino) pyrrolidin-1-yl, 4-carboxypiperidin-1-yl, 1-methyl-2-oxo-5-phenyl-pyrrolidin-4-yl, 2-oxo-5,5-dimethyltetrahydrofur-4-yl, tetrahydrofur-4-yl, 2,2-dimethyltetrahydropyran-4-yl, 1-benzyl-2-oxopyrrolidin-4-yl, 2-oxo-5-phenyltetrahydrofuryl, 2-(3-hydroxypropyl)piperidin-1-yl, 4-(2-carbamoylethyl)piperazin-1-yl, 3-oxo-4-(2-methoxyethyl)piperazin-1-yl, 4-(N,N-dimethylamino)-4-carbamoylpiperidin-1-yl, 4-(2-morpholinoethyl)piperazin-1-yl, 1,4-dioxa-8-azaspiro[4.5]decan-8-yl, 1,1-dioxotetrahydrothien-3-yl, 4-ethylsulphonylpiperazin-1-yl, 4-(thieno[2,3-d]pyrimidin-4-yl)piperazin-1-yl, 4-(2-hydroxyethyl)piperazin-1-yl, 4-carbamoylpiperidin-1-yl, 3-methyl-3-phenylpiperidin-1-yl, 2-benzyloxycarbonylpiperidin-1-yl, 4-(N,N-dimethylcarbamoyl)piperidin-1-yl, 3-(pyrid-4-yl)pyrrolidin-1-yl, 3-(pyrid-3-yl)pyrrolidin-1-yl, 4,4-difluoropiperidin-1-yl, 4-(2-methylpyrimidin-4-yl)piperazin-1-yl, 4-(2,3,5,6-tetrafluoropyrid-4-yl)piperazin-1-yl 4-(pyrimidin-4-yl) piperazin-1-yl, 3-cyanomethylpiperidin-1-yl, 4-cyclohexylcarbonylaminopiperidin-1-yl, 4-acetamidopiperidin-1-yl, 4-(6-chloropyrimidin-4-yl) piperazin-1-yl, 4-(pent-3-yl)piperazin-1-yl, 1,2,5,6-tetrahydropyrid-1-yl, 1-methylpiperidin-1-yl, 2-methylpiperidin-1-yl, decahydroquinolin-1-yl, 3-ethoxycarbonyl-4-oxopiperidin-1-yl, 2-ethoxycarbonylpyrrolidin-1-yl, 4-acetylpiperidin-1-yl, 2-azabicyclo[2.2.1]hept-2-yl, 1,2,3,4,-tetrahydro-9H-pyrido[3,4-b]indol-2-yl, 4-(2,3-dihydro-2-oxobenzimidazol-1-yl) piperidin-1-yl, 4-(2-methoxyphenyl)piperazin-1-yl, 4-methylpiperidin-1-yl, 4-(3-chlorophenyl)piperazin-1-yl, 4-(3-methoxyphenyl)piperazin-1-yl, 4-(4-methoxyphenyl) piperazin-1-yl, 4-(4-chlorophenyl)piperazin-1-yl, 4-(2,3-dihydro-2-oxobenzimidazol-1-yl)-1,2,5,6-tetrahydropyrid-1-yl, 4-phenylpiperidin-1-yl, 4-(3-fur-2-ylpyrazol-5-yl) piperidin-1-yl, 2-pyrid-4-ylethylamino, 3-imidazol-1-ylpropylamino, 4-hydroxycyclohexylamino, 2-(N,N-dimethylsulphamoylamino)ethylamino, 2-(isopropylsulphonylamino)ethylamino, 2-imidazol-5-ylethylamino, 2-mesylethylamino, 2-morpholinoethylamino, 1-methoxycarbonylcyclopropylamino, 1-benzylpyrrolidin-3-ylamino, 3-(N-methylanilino)propylamino, 2-(5-methyl-2,4-dioxothiazolidin-3-yl)ethylamino, 2-(t-butoxycarbonylamino)ethylamino, N-(N-methyl-N-pyrid-3-ylmethylaminopropyl)amino, 1-cyclohexylethylamino, N-methyl-N-(2-pyrid-4-ylethyl)amino, N-methyl-N-(2-pyrid-2-ylethyl)amino, N-methyl-N-(2-cyanoethyl)amino, N-methyl-N-(pyrid-3-ylmethyl)amino, N-methyl-N-(2-N,N-dimethylaminoethyl)amino, N-methyl-N-(1-methylpiperidin-4-yl)amino, N-methyl-N-(3-mesylpropyl) amino, N-methyl-N-(4-hydroxy-4-methyltetrahydropyran-3-yl)amino, N-(pyrid-3-ylmethyl)-N-(2-cyanoethyl)amino, N-methyl-N-(2-hydroxypropyl)amino, N-methyl-N-(2,2-dimethoxyethyl)amino, N-methyl-N-phenethylamino, N-methyl-N-(tetrahydrofur-2-ylmethyl)amino, N-methyl-N-2-morpholinoethyl)amino, N-methyl-N-(6-methylpyrid-2-ylmethyl)amino, N-methyl-N-(1-methylpyrrolidin-3-yl)

amino, N-methyl-N-[2-(4-hydroxyphenyl)-2-hydroxyethyl]amino, N-methyl-N-(1-benzylpyrrolidin-3-yl)amino, N-methyl-N-[2-(1,2,4-triazol-1-yl)ethyl]amino, N-methyl-N-(fur-2-ylmethyl)amino, N-methyl-N-(benzimidazol-2-ylmethyl)amino, N-methyl-N-benzylamino, N-methyl-N-(2-chlorobenzyl)amino, N-methyl-N-(3-chlorobenzyl)amino, N-methyl-N-(4-chlorobenzyl)amino, N-methyl-N-[2-(3,4-dimethoxypyrid-4-yl)ethyl]amino, N-methyl-N-(5-phenylpyrazol-3-ylmethyl)amino, N-methyl-N-(4-fluorobenzyl)amino, N-methyl-N-(2-methoxyphenylprop-2-yl)amino, N-ethyl-N-(pyrid-4-ylmethyl)amino, N-(2-methoxyethyl)-N-(pyrid-3-ylmethyl)amino, N-ethyl-N-(2-methxoyethyl)amino, N-(2-hydroxyethyl)-N-isopropylamino, N-(2-cyanoethyl)-N-(3-morpholinopropyl)amino, N-2-cyanoethyl)-N-(thien-2-ylmethyl)amino, N-(2-cyanoethyl)-N-benzylamino, N-ethyl-N-(1-benzylpyrrolidin-3-yl)amino, N-ethyl-N-(1,1-dioxotetrahydrothien-3-yl)amino, N-(2-pyrid-4-ylethyl)-N-cyclopropylamino, N-(2-hydroxy-2-pyrid-4-ylethyl)-N-isopropylamino, N-(4-hydroxycyclohexyl)-N-isopropylamino, N-allyl-N-(1,1-dioxotetrahydrothien-3-yl)amino, diallylamino, N-allyl-N-cyclopentylamino or N-benzyl-N-propylamino.

6. The method of claim 1 or claim 2, wherein $R^4$ is $C_{1-4}$alkyl.

7. The method of claim 1, wherein x is 0.

8. The method of claim 1, wherein y is 0–1.

9. The method of claim 1, wherein n is 2.

10. The method of claim 1, wherein:

X is a group of formula (A) in the 2-position of the dibenzothiophene ring;

$R^2$ is bromo, cyano or methyl;

A is —$NR^a$—, —O— or a direct bond; wherein $R^a$ is hydrogen, methyl, ethyl, propyl, isopropyl or allyl; wherein said methyl, ethyl, propyl, isopropyl or allyl may be optionally substituted by one or more $R^5$;

$R^3$ is methyl, ethyl, propyl, butyl, hexyl or allyl wherein $R^3$ may be optionally substituted by one or more $R^6$; or $R^3$ is selected from cyclopropyl, cyclopentyl, cyclohexyl, bicyclo[2,2,1]heptyl, phenyl, tetrahydropyranyl, morpholino, 2-oxopyrrolidinyl, piperidinyl, pyrrolidinyl, azetidinyl, tetrahydrofuryl, 1,4-dioxa-8-azaspiro[4.5]decanyl, 1,1-dioxotetrahydrothienyl, 1,2,3,4,-tetrahydro-9H-pyrido[3,4-b]indole, decahydroquinolin-1-yl, 1,2,5,6-tetrahydropyridyl or piperazinyl; wherein $R^3$ may be optionally substituted on carbon by one or more $R^7$; and wherein if any heterocyclyl contains an —NH— moiety that nitrogen may be optionally substituted by $R^8$;

$R^5$ is selected from cyano, methoxy, pyridyl;

$R^6$ is selected from hydroxy, cyano, amino, methoxy, pyridyl, 2-oxopyrrolidinyl, 1,2,4-triazolyl, 1,1-dioxotetrahydrothienyl, thienyl, 2-oxooxazolidinyl, imidazolyl, 1,1-dioxothiomorpholino, 2-oxo-1,2-dihydropyridyl, benzimidazolyl, pyrazolyl, succinimido, tetrahydrofuryl, 2,4-dioxothiazolidinyl, morpholino, furyl, pyridyloxy, pyridazinyloxy, cyclopentyl, cyclohexyl, phenyl, phenoxy, N-methylanilino, N,N-dimethylamino, t-butoxycarbonylamino, mesyl, N,N-dimethylsulphamoylamino and isopropylsulphonylamino; wherein $R^6$ may be optionally substituted on carbon by one or more $R^9$;

$R^7$ is selected from fluoro, hydroxy, nitro, carboxy, carbamoyl, methyl, ethyl, propyl, methoxycarbonyl, ethoxycarbonyl, acetyl, acetamido, N,N-dimethylamino, N,N-dimethylcarbamoyl, N,N-diethylcarbamoyl, 1,4-dihydrooxazin-2-one, pyrazolyl, 2-oxo-2,3-dihydrobenzimidazolyl, pyridyl, 2,3-dihydro-2-oxobenzimidazolyl, morpholinocarbonyl, phenyl and cyclohexylcarbonylamino; wherein any $R^7$ may be optionally substituted on carbon by one or more $R^{11}$;

$R^9$ is selected from fluoro, chloro, hydroxy, methyl, methoxy, pyridyl and phenyl;

$R^8$ is selected from methyl, ethyl, propyl, pentyl, ethylsulphonyl, N,N-dimethylsulphamoyl, thieno[2,3-d]pyrimidinyl, pyrimidinyl, pyridyl and phenyl; wherein any $R^8$ may be optionally substituted on carbon by one or more $R^{12}$;

$R^{11}$ is selected from hydroxy, cyano, allyloxy, pyrrolidinyl, furyl and phenyl;

$R^{12}$ is selected from fluoro, chloro, hydroxy, carbamoyl, methyl, methoxy, tetrahydrofuryl, morpholino and phenyl;

x is 0 y is 0–1;

n is 0–2;

or a pharmaceutically acceptable salt, prodrug or solvate thereof;

with the provisos when X is a group of formula (A):
1) when $R^3$ is a nitrogen linked heterocyclyl, A is a direct bond;
2) when x and y are 0 and n is 2, the group $R^3$—A—C(O)—NH— is not 2-acetamido, 2-propionamido, 2-(2-aminoacetamido), 2-(3-aminopropionamido), 2-(2-amino-2-isopropylacetamido) or 2-(2-amino-2-benzylacetamido);
3) when x and y are 0 and n is 0, the group $R^3$—A—C(O)—NH— is not 2-benzamido, 2-acetamido, 2-benzyloxycarbonylamino, 2-(2-aminoacetamido), 2-(3-aminopropionamido), 2-(2-amino-2-isopropylacetamido) or 2-(2-amino-2-benzylacetamido);
4) when x is 0, $(R^2)_y$ is 1-cyano and n is 0, the group $R^3$—A—C(O)—NH— is not 2-acetamido;
5) when x is 0, $(R^2)_y$ is 3-bromo and n is 0, the group $R^3$—A—C(O)—NH—is not 2-acetamido or 2-benzamido; and
6) when x is 0, $(R^2)_y$ is 1-bromo and n is 0, the group $R^3$—A—C(O)—NH—is not 2-acetamido or 2-benzamido.

11. The method of claim 1 or claim 2, wherein the compound is selected from:

2-(N'-pyrid-4-ylethyl-N'-methylureido)dibenzothiophene;

5,5-dioxo-2-N'-pyrid-4-ylethyl-N'-methylureido)dibenzothiophene;

5,5-dioxo-2-[4-(pyrid-4-yl)piperidin-1-ylcarbonylamino]dibenzothiophene;

5,5-dioxo-2-[4-(pyrid-2-yl)piperidin-1-ylcarbonylamino]dibenzothiophene;

5,5-dioxo-2-(N'-phenethyl-N'-methylureido)dibenzothiophene;

5,5-dioxo-2-(4,4,4-trifluoro-2-methylbutyrylamino)dibenzothiophene;

5,5-dioxo-2-[4-(2,3,5,6-tetrafluoropyrid-4-yl)piperazin-1-ylcarbonylamino]dibenzothiophene;

or a pharmaceutically acceptable salt, prodrug or solvate thereof.

12. A process for preparing a compound of formula (I):

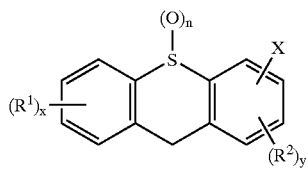

wherein:

X is a group of formula (A):

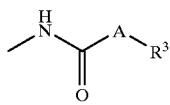

$R^1$ is cyano, halo, trifluoromethyl, trifluoromethoxy, $C_{1-4}$alkyl, $C_{1-4}$alkoxy, N-($C_{1-4}$alkyl)amino or N,N-($C_{1-4}$ alkyl)$_2$amino;

$R^2$ is halo, cyano, hydroxy, trifluoromethyl, trifluoromethoxy, $C_{1-4}$alkyl or $C_{1-4}$alkoxy;

A is —$NR^a$—, —O— or a direct bond, wherein $R^a$ is hydrogen, $C_{1-4}$alkenyl, $C_{2-10}$alkynyl; wherein $R^a$ may be optionally substituted by one or more $R^5$;

$R^3$ is hydrogen, $C_{1-10}$alkyl, $C_{2-10}$alkenyl or $C_{2-10}$alkynyl wherein $R^3$ may be optionally substituted by one or more $R^6$; or $R^3$ is carbocyclyl or heterocyclyl wherein $R^3$ may be optionally substituted on carbon by one or more $R^7$; and wherein if said heterocyclyl contains an —NH— moiety, that nitrogen may be optionally substituted by $R^8$;

$R^5$ and $R^6$ are independently selected from halo, hydroxy, cyano, carbamoyl, ureido, amino, nitro, carboxy, carbamoyl, mercapto, sulphamoyl, aminosulphamoyl, $C_{1-6}$alkoxy, $C_{1-6}$alkanoyl, $C_{1-6}$alkanoyloxy, $C_{1-6}$alkanoylamino, $C_{2-6}$alkenyloxycarbonyl, $C_{1-6}$alkoxycarbonyl, heterocyclyl, heterocyclyloxy, heterocyclylamino, heterocyclyl-N-($C_{1-6}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-6}$alkyl)amino, carbocyclylsulphonyl, carbocyclylcarbonyl, carbocyclylcarbonylamino, carbocyclyloxycarbonyl, N-($C_{1-6}$alkyl)amino, N,N-($C_{1-6}$alkyl)$_2$amino, $C_{1-6}$alkoxycarbonylamino, N-($C_{1-6}$alkyl)carbamoyl, N,N-($C_{1-6}$alkyl)$_2$carbamoyl, $C_{1-6}$alkylS(O)$_a$wherein a is 0–2, N-($C_{1-6}$alkyl)sulphamoylamino, N,N-($C_{1-6}$ alkyl)$_2$sulphamoylamino, $C_{1-6}$alkylsulphonylamino, ($C_{1-6}$alkyl)sulphonyl-N-($C_{1-6}$alkyl)amino, N-($C_{1-6}$ alkyl)sulphamoyl and N,N-($C_{1-6}$alkyl)$_2$sulphamoyl; wherein $R^5$ and $R^6$ may be optionally substituted on carbon by one or more $R^9$; and wherein if said heterocyclyl contains an —NH— moiety, that nitrogen may be independently optionally substituted by $R^{10}$;

$R^7$ and $R^9$ are independently selected from halo, hydroxy, cyano, carbamoyl, ureido, trifluoromethyl, trifluoromethoxy, amino, nitro, carboxy, carbamoyl, mercapto, sulphamoyl, aminosulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{1-4}$alkoxycarbonylamino, $C_{2-4}$alkenyloxycarbonyl, $C_{1-4}$alkanoyl, $C_{1-4}$alkanoylamino, $C_{1-4}$alkanolyoxy, N-($C_{1-4}$alkyl)amino, N,N-($C_{1-4}$alkyl)$_2$amino, N-($C_{1-4}$alkyl)carbamoyl, N,N-($C_{1-4}$alkyl)$_2$carbamoyl, $C_{1-4}$alkylS(O)$_a$ wherein a is 0–2, N-($C_{1-4}$-alkyl)sulphamoylamino, N,N-($C_{1-4}$alkyl)$_2$sulphamoylamino, ($C_{1-4}$)sulphomylamino, ($C_{1-4}$alkyl)sulphonyl-N-($C_{1-4}$ alkyl)amino, N-($C_{1-4}$alkyl)sulphamoyl, N,N-($C_{1-4}$ alkyl)$_2$sulphamoyl, heterocyclyl, heterocyclyloxy, heterocyclylamino, heterocyclyl-N-($C_{1-4}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-4}$alkyl)amino, carboocyclylsulphonyl, carbocyclylcarbonyl, carbocyclylcarbonylamino, and carbocyclyloxycarbonyl, wherein $R^7$ and $R^9$ may be independently optionally substituted on carbon by one or more $R^{11}$;

$R^8$ and $R^{10}$ are independently selected from $C_{1-4}$alkyl, $C_{1-4}$alkanoyl, sulphamoyl, $C_{1-4}$alkysulphonyl, $C_{1-4}$alkoxycarbonyl, carbamoyl, N-($C_{1-4}$alkyl)carbamoyl, N,N-($C_{1-4}$alkyl)carbamoyl, N-($C_{1-4}$alkyl)sulphamoyl, N,N-($C_{1-4}$alkyl)$_2$sulphamoyl, heterocyclyl, heterocyclylcarbonyl, heterocyclyloxycarbonyl, heterocyclylsulphonyl, carbocyclyl, carbocyclylcarbonyl, carbocyclyloxycarbonyl and carbocyclylsulphonyl; wherein $R^8$ and $R^{10}$ may be independently optionally substituted on carbon by one or more $R^{12}$;

$R^{11}$ and $R^{12}$ are independantly selected from halo, hydroxy, cyano, carbamoyl, uriedo, amino, nitro, carboxy, carbamoyl, mercapto, sulphamoyl, methyl, ethyl, vinyl, allyl, methoxy, ethoxy, vinyloxy, allyloxy, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

x is 0–4; wherein the values of $R^1$ may be the same or different;

y is 0–3; wherein the values of $R^2$ may be the same or different; and n is 0–2:

or a pharmaceutically acceptable salt, prodrug or solvate thereof;

with the provisos when X is a group of formula (A);

1) when $R^3$ is a nitrogen linked heterocyclyl, A is a direct bond;

2) when x and y are 0 and n is 2, the group $R^3$—A—C(O)—NH— is not 2-formamido, 2-acetamido, 3-acetamido, 2-propionamido, 3-[2-(fur-2-ylcarbonylmethyl)acetamido], 2-(2-phthalimidoacetamido), 2-(3-phthalimidopropionamido), 2-(2-phthalimido-2-isopropylacetamido), 2-(2-phthalimido-2-isobutylacetamido), 2-(2-phthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(2-phthalimidoacetamido), 3-(3-phthalimidopropionamido), 3-(2-phthalimido-2-isopropylacetamido), 3-(2-phthalimido-2-isobutylacetamido), 3-(2-phthalimido-2-benzylacetamido), 3-(2-aminoacetamido), 3-(3- aminopropionamido), 3-(2-amino-2-isopropylacetamido), 3-(2-amino-2-benzylacetamido) or 2-(3,3,3-trifluoro-2-hydroxy-2-methylpropionamido);

3) when x and y are 0 and n is 1, the group R³—A—C(O)—NH— is not 3-acetamido, 3-(2-phthalimidoacetamido), 3-(3-phthalimidopropionamido), 3-(2-phthalimido-2-isopropylacetamido), 3-(2-phthalimido-2-isobutylacetamido), 3-(2-phthalimido-2-benzylacetamido), 3-(2-aminoacetamido), 3-(3-aminopropionamido), 3-(2-amino-2-isopropylacetamido), 3-(2-amino-2-isobutlacetamido) or 3-(2-amino-2-benzylacetamido);

4) when x and y are 0 and n is 0, the group R³—A—C(O)—NH— is not 2-benzamido, 2-acetamido, 2-benzyloxycarbonylamino, 2-(2-phthalimidoacetamido), 2-(3-phthalimidopropionamido), 2-(2-phthalimido-2-isopropylacetamido), 2-(2-phthalimido-2-isobutylacetamido), 2-(2-phthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetanido), 3-(trifluoroacetamido), 3-benzyloxycarbonylamino or 4-t-butyloxycarbonylamino;

5) when (R¹)ₓ is 7-fluoro, y is 0 and n is 2, the group R³—A—C(O)—NH— is not 3-acetamido;

6) when x is 0, (R²)ᵧ is 1-cyano and n is 0, the group R³—A—C(O)—NH— is not 2-acetamido;

7) when x is 0, (R²)ᵧ is 3-bromo and n is 0, the group R³—A—C(O)—NH— is not 2-acetamido or 2-benzamido;

8) when x is 0, (R²)ᵧ is 1-bromo and n is 0, the group R³—A—C(O)—NH— is not 2-acetamido or 2-benzamido; and 9) when x is 0, (R²)ᵧ is 1-chloro or 4-chloro and n is 0, the group R³—A—C(O)—NH— is not 2-acetamido or a pharmaceutically acceptable salt or an in vivo hydrolysable ester thereof which process (wherein R¹, R², R³, A and n are, unless otherwise specified, as defined in formula (I)) comprises of:

*Process a)*: for compounds of formula (1) wherein A is a direct bond and X is a group of formula (A); reacting an amine of formula (II):

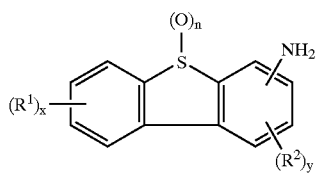

(II)

with an acid of formula (III):

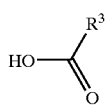

(III)

or an activated derivative thereof; or

*Process b)*: for compounds of formula (1) wherein n>0; by oxidising a compound of formula (I) where n=0;

*Process c)*: for compounds of formula (1) wherein A is —NRᵃ— and X is a group of formula (A); by reacting a compound of formula (IV);

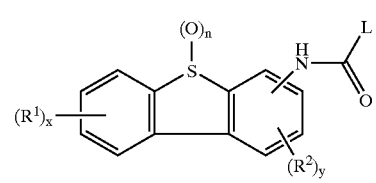

(IV)

wherein L is a displaceable group; with an amine of formula (V):

HNRᵃR³ (V)

*Process d)*: for compounds of formula (I) wherein A is —NRᵃ— or —O— and X is a group of formula (A); reacting a compound of formula (II) with a compound of formula (VI);

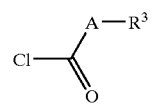

(VI)

*Process e)*: for compounds of formula (I) wherein A is —NH— and X is a group of formula (A); reacting a compound of formula (II) with an isocyanate of formula (VII):

O=N—R³ (VII)

13. A method of treating a disorder mediated by the neuropeptide Y5 receptor in a warm-blooded animal in need of such treatment, comprising administering to said animal a therapeutically effective amount of a compound of formula (IA'):

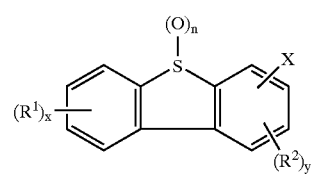

(IA')

wherein:
X is a group of formula (A):

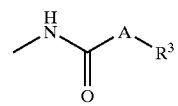

(A)

R¹ is cyano, halo, trifluoromethyl, trifluoromethoxy, $C_{1-4}$alkyl, $C_{1-4}$alkoxy, N-($C_{1-4}$alkyl)amino or N,N-($C_{1-4}$ alkyl)₂amino;

R² is halo, cyano, hydroxy, trifluoromethyl, trifluoromethoxy, $C_{1-4}$alkyl or $C_{1-4}$alkoxy;

A is —NRᵃ—, —O— or a direct bond; wherein Rᵃ is hydrogen, $C_{1-10}$alkyl, $C_{2-10}$ alkenyl, $C_{2-10}$alkynyl; wherein Rᵃ may be optionally substituted by one or more R⁵;

R³ is hydrogen, $C_{1-10}$alkyl, $C_{2-10}$alkenyl or $C_{2-10}$alkynyl wherein R³ may be optionally substituted by one or more $R^6$; or $R^3$ is carbocyclyl or heterocyclyl wherein $R^3$ may be optionally substituted on carbon by one or more $R^7$; and wherein if said heterocyclyl contains an —NH— moiety, that nitrogen may be optionally substituted by $R^8$;

$R^5$ and $R^6$ are independently selected from halo, hydroxy, cyano, carbamoyl, ureido, amino, nitro, carboxy, carbamoyl, mercapto, sulphamoyl, aminosulphamoyl, $C_{1-6}$alkoxy, $C_{1-6}$alkanoyl, $C_{1-6}$alkanoyloxy, $C_{1-6}$alkanoylamino, $C_{2-6}$alkenyloxycarbonyl, $C_{1-6}$alkoxycarbonyl, heterocyclyl, heterocyclyloxy, heterocyclylamino, heterocyclyl-N-($C_{1-6}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-6}$alkyl)amino, carbocyclylsulphonyl, carbocyclylcarbonyl, carbocyclylcarbonylamino, carbocyclyloxycarbonyl, N-($C_{1-6}$alkyl)amino, N,N-($C_{1-6}$alkyl)$_2$amino, $C_{1-6}$alkoxycarbonylamino, N-($C_{1-6}$alkyl)carbamoyl, N,N-($C_{1-6}$alkyl)$_2$carbamoyl, $C_{1-6}$alkylS(O)$_a$ wherein a is 0–2, N-($C_{1-6}$alkyl)sulphamoylamino, N,N-($C_{1-6}$alkyl)$_2$sulphamoylamino, $C_{1-6}$alkylsulphonylamino, ($C_{1-6}$alkyl)sulphonyl-N-($C_{1-6}$alkyl)amino, N-$C_{1-6}$alkyl)sulphamoyl and N,N-($C_{1-6}$alkyl)$_2$sulphamoyl; wherein $R^5$ and $R^6$ may be optionally substituted on carbon by one or more $R^9$; and wherein if said heterocyclyl contains an —NH— moiety, that nitrogen may be independently optionally substituted by $R^{10}$;

$R^7$ and $R^9$ are independently selected from halo, hydroxy, cyano, carbamoyl, ureido, trifluoromethyl, trifluoromethoxy, amino, nitro, carboxy, carbamoyl, mercapto, sulphamoyl, aminosulphamoyl, $C_{1-4}$alkyl, $C_{2-4}$alkenyl, $C_{2-4}$alkynyl, $C_{1-4}$alkoxy, $C_{1-4}$alkoxycarbonyl, $C_{1-4}$alkoxycarbonylamino, $C_{2-4}$alkenyloxycarbonyl, $C_{1-4}$alkanoyl, $C_{1-4}$alkanoylamino, $C_{1-4}$alkanoyloxy, N-($C_{1-4}$alkyl)amino, N,N-($C_{1-4}$alkyl)$_2$amino, N-($C_{1-4}$alkyl)carbamoyl, N,N-($C_{1-4}$alkyl)$_2$carbamoyl, $C_{1-4}$alkylS(O)$_a$ wherein a is 0–2, N-($C_{1-4}$alkyl)sulphamoylamino, N,N-($C_{1-4}$alkyl)$_2$sulphamoylamino, ($C_{1-4}$alkyl)sulphonylamino, ($C_{1-4}$alkyl)sulphonyl-N-($C_{1-4}$alkyl)amino, N-($C_{1-4}$alkyl)sulphamoyl, N,N-($C_{1-4}$alkyl)$_2$sulphamoyl, heterocyclyl, heterocyclyloxy, heterocyclylamino, heterocyclyl-N-($C_{1-4}$alkyl)amino, heterocyclylsulphonyl, heterocyclylcarbonyl, heterocyclylcarbonylamino, heterocyclyloxycarbonyl, carbocyclyl, carbocyclyloxy, carbocyclylamino, carbocyclyl-N-($C_{1-4}$alkyl)amino, carboocyclylsulphonyl, carbocyclylcarbonyl, carbocyclylcarbonylamino, and carbocyclyloxycarbonyl; wherein $R^7$ and $R^9$ may be independently optionally substituted on carbon by one or more $R^{11}$;

$R^8$ and $R^{10}$ are independently selected from $C_{1-4}$alkyl, $C_{1-4}$alkanoyl, sulphamoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)$_2$carbamoyl, N-($C_{1-4}$alkyl)sulphamoyl, N,N-($C_{1-4}$alkyl)$_2$sulphamoyl, heterocyclyl, heterocyclylcarbonyl, heterocyclyloxycarbonyl, heterocyclylsulphonyl, carbocyclyl, carbocyclylcarbonyl, carbocyclyloxycarbonyl and carbocyclylsulphonyl; wherein $R^8$ and $R^{10}$ may be independently optionally substituted on carbon by one or more $R^{12}$;

$R^{11}$ and $R^{12}$ are independently selected from halo, hydroxy, cyano, carbamoyl, ureido, amino, nitro, carboxy, carbamoyl, mercapto, sulphamoyl, methyl, ethyl, vinyl, allyl, methoxy, ethoxy, vinyloxy, allyloxy, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

x is 0–4; wherein the values of $R^1$ may be the same or different;

y is 0–3; wherein the values of $R^2$ may be the same or different;

n is 0–2;

or a pharmaceutically acceptable salt, prodrug or solvate thereof;

with the provisos when X is a group of formula (A):

1) when $R^3$ is a nitrogen linked heterocyclyl, A is a direct bond;

2) when x and y are 0 and n is 2, the group $R^3$—A—C(O)—NH— is not 2-formamido, 2-acetamido, 2-propionamido, 2-(2-phthalimidoacetamido), 2-(3-phthalimidopropionamido), 2-(2-phthalimido-2-isopropylacetamido), 2-(2-phthalimido-2-isobutylacetamido), 2-(2-phthalimido-2-benzylacetamido), 2-(2-aminoacetamido), 2-(3-aminopropionamido), 2-(2-amino-2-isopropylacetamido), 2-(2-amino-2-isobutylacetamido), 2-(2-amino-2-benzylacetamido), 3-(2-phthalimidoacetamido), 3-(3-phthalimidopropionanido), 3-(2-phthalimido-2-isopropylacetamido), 3-(2-phthalimido-2-isobutylacetamido), 3-(2-phthalimido-2-benzylacetamido), 3-(2-aminoacetamido), 3-(3-aminopropionamido), 3-(2-amino-2-isopropylacetamido), 3-(2-amino-2-benzylacetamido) or 2-(3,3,3-trifluoro-2-hydroxy-2-methylpropionamido);

3) when x and y are 0 and n is 1, the group $R^3$—A—C(O)NH— is not 3-(2-phthalimidoacetamido), 3-(3-phthalimidopropionamido), 3-(2-phthalimido-2-isopropylacetamido), 3-(2-phthalimido-2-isobutylacetamido), 3-(2-phthalimido-2-benzylacetamido), 3-(2-aminoacetamido), 3-(3-aminopropionamido), 3-(2-amino-2-isopropylacetamido), 3-(2-amino-2-isobutylacetamido) or 3-(2-amino-2-benzylacetamido);

4) when x and y are 0 and n is 0, the group $R^3$—A—C(O)—NH— is not 2-(2-phthalimidoacetamido), 2-(3-phthalimidopropionamido), 2-(2-phthalimido-2-isopropylacetamido), 2-(2-phthalimido-2-isobutylacetamido), 2-(2-phthalimido-2-benzylacetamido), 2-(2-aminoacetamido), 2-(3-aminopropionamido), 2-(2-amino-2-isopropylacetamido), 2-(2-amino-2-isobutylacetamido) or 2-(2-amino-2-benzylacetamido);

5) when $(R^1)_x$ is 7-fluoro, y is 0 and n is 2, the group $R^3$—A—C(O)—NH— is not 3-acetamido;

or a pharmaceutically acceptable salt, prodrug or solvate thereof, for use as a medicament.

14. A method of any one of claim 1, 2, 3, 8, 9, 12, or 13, wherein the disorder is an eating disorder.

15. A method as claimed in claim 14, wherein the eating disorder is selected from obesity and related disorders, bulimia or anorexia, wherein the related disorders are diabetes dyslipidaemia, hypertension and sleep disturbances.

16. A method as claimed in any one of claim 1, 2, 3, 8, 9, 12, or 13, wherein the method promotes weight loss.

17. A pharmaceutical composition comprising a compound, or a pharmaceutically acceptable salt, prodrug or solvate thereof, as defined in any one of claim 1, 2, 3, 8, 9, 12, or 13, in association with a pharmaceutically acceptable diluent or carrier for the treatment of disorders mediated by the neuropeptide Y5 receptor in a warm-blooded animal in need of such treatment.

18. A pharmaceutical composition comprising a compound, or a pharmaceutically acceptable salt, prodrug or solvate thereof, as defined in any one of claim 1, 2, 3, 8, 9, 12, or 13, in association with a pharmaceutically acceptable diluent or carrier for the treatment of an eating disorder in a warm-blooded animal.

19. A pharmaceutical composition comprising a compound, or a pharmaceutically acceptable salt, prodrug or solvate thereof, as defined in any one of claim 1, 2, 3, 8, 9, 12, or 13, in association with a pharmaceutically acceptable diluent or carrier for promoting weight loss in a warm-blooded animal.

* * * * *

UNITED STATES PATENT AND TRADEMARK OFFICE
CERTIFICATE OF CORRECTION

PATENT NO. : 6,967,216 B2
APPLICATION NO. : 10/275529
DATED : November 22, 2005
INVENTOR(S) : Block et al.

It is certified that error appears in the above-identified patent and that said Letters Patent is hereby corrected as shown below:

Claim 1, Col. 98, line 58, change "$(R^1)$" to --$(R^1)_x$--;

Claim 3, Col. 99, line 5, delete "or claim 2";

Claim 4, Col. 99, line 7, delete "or claim 2";

Claim 5, Col. 99, line 44, change "claim" to --claims--;

Claim 5, Col. 99, line 64, change "1-methyl-2-oxopyrrolidin4-yl" to --1-methyl-2-oxopyrrolidin-4-yl--

Claim 5, Col. 100, line 66, change "N-2-morpholinoethyl)amino" to --N-(2-morpholinoethyl)amino--

Claim 10, Col. 102, line 25, after "0-1;" insert --and--

Claim 12, Col. 103, line 27, change "hydrogen, $C_{1-4}$alkenyl,$C_{2-10}$alkynyl" to --hydrogen, $C_{1-10}$alkyl, $C_{2-10}$alkenyl, $C_{2-10}$alkynyl--

Claim 13, Col. 108, line 29, change "3-(3-phthalimidopropionanido)" to --3-(3-phthalimidopropionamido)--

Signed and Sealed this

Fifth Day of September, 2006

JON W. DUDAS
*Director of the United States Patent and Trademark Office*